US011160825B2

(12) United States Patent
Stefano et al.

(10) Patent No.: US 11,160,825 B2
(45) Date of Patent: Nov. 2, 2021

(54) METHODS AND MATERIALS FOR TREATING DIABETES OR LIVER STEATOSIS

(71) Applicant: The Research Foundation for The State University of New York, Albany, NY (US)

(72) Inventors: George B. Stefano, Melville, NY (US); Richard Kream, Huntington, NY (US); Kirk J Mantione, Patchogue, NY (US)

(73) Assignee: Research Foundation of the State University of New York, Albany, NY (US)

( * ) Notice: Subject to any disclaimer, the term of this patent is extended or adjusted under 35 U.S.C. 154(b) by 1021 days.

(21) Appl. No.: 15/023,069

(22) PCT Filed: Aug. 29, 2014

(86) PCT No.: PCT/US2014/053443
§ 371 (c)(1),
(2) Date: Mar. 18, 2016

(87) PCT Pub. No.: WO2015/041837
PCT Pub. Date: Mar. 26, 2015

(65) Prior Publication Data
US 2016/0243152 A1 Aug. 25, 2016

Related U.S. Application Data
(60) Provisional application No. 61/879,992, filed on Sep. 19, 2013.

(51) Int. Cl.
| *A61K 31/716* | (2006.01) |
| *A61K 36/81* | (2006.01) |
| *A61K 31/355* | (2006.01) |
| *A61K 31/385* | (2006.01) |
| *A61K 36/39* | (2006.01) |
| *A61K 9/20* | (2006.01) |

(52) U.S. Cl.
CPC .............. *A61K 31/716* (2013.01); *A61K 9/20* (2013.01); *A61K 31/355* (2013.01); *A61K 31/385* (2013.01); *A61K 36/39* (2013.01); *A61K 36/81* (2013.01)

(58) Field of Classification Search
CPC .. A61K 36/81; A61K 2300/00; A61K 31/355; A61K 31/385; A61K 31/716; A61K 36/39; A61K 9/20; A61P 1/16; A61P 3/06; A61P 3/10; A61P 43/00
USPC ....................................................... 424/773
See application file for complete search history.

(56) References Cited

U.S. PATENT DOCUMENTS

| 2,134,714 A | 11/1938 | Glassman |
| 3,622,677 A | 11/1971 | Short |
| 7,041,730 B2 | 5/2006 | Rogers et al. |
| 7,098,239 B2 | 8/2006 | Edmondson et al. |
| 7,590,493 B2 | 9/2009 | Menderick et al. |
| 7,893,252 B2 | 2/2011 | Platt et al. |
| 2003/0159178 A1 | 8/2003 | Ulvskov et al. |
| 2003/0187058 A1 | 10/2003 | Hasselwander et al. |
| 2004/0038933 A1 | 2/2004 | Kaneko et al. |
| 2005/0031651 A1 | 2/2005 | Gervais et al. |
| 2005/0085498 A1 | 4/2005 | Byrd |
| 2005/0180962 A1 | 8/2005 | Raz et al. |
| 2005/0214413 A1 | 9/2005 | McNalley et al. |
| 2006/0264383 A1 | 11/2006 | Kingston |
| 2008/0213400 A1 | 9/2008 | Fine et al. |
| 2008/0279984 A1 | 11/2008 | Kalum et al. |
| 2010/0129333 A1* | 5/2010 | Kawakami ............ A61K 35/74 424/93.45 |
| 2010/0143513 A1 | 6/2010 | Lee et al. |
| 2011/0077217 A1 | 3/2011 | Platt et al. |
| 2011/0081475 A1 | 4/2011 | Huber et al. |
| 2013/0259870 A1* | 10/2013 | Traber ................. A61K 31/732 424/141.1 |
| 2013/0309355 A1 | 11/2013 | Wong et al. |
| 2013/0315826 A1 | 11/2013 | Mukherjee et al. |
| 2014/0024602 A1 | 1/2014 | Sundaram et al. |
| 2015/0065451 A1 | 3/2015 | Stefano |
| 2017/0232033 A1 | 8/2017 | Stefano et al. |
| 2018/0078575 A1 | 3/2018 | Stefano et al. |
| 2018/0078599 A1 | 3/2018 | Stefano et al. |

FOREIGN PATENT DOCUMENTS

| CN | 103110657 | 5/2013 |
| JP | 2001/511153 | 8/2001 |
| JP | 2004-508399 | 3/2004 |

(Continued)

OTHER PUBLICATIONS

Katimbwa DA, et al "Potato Extract Inhibits Lipase Activity and Ameliorates Gut Microbiome Dysbiosis and Weight Gain in Mice Fed a High-Fat Diet" Appl Biol Chem, Feb. 9, 2021 ,64(17),14 page; doi: 10.1186/s13765-021-00590-w. (Year: 2021).*
Benz et al., "Tonal nitric oxide and health—a free radical and a scavenger of free radicals," *Med Sci. Monit.*, 8(1):RA1-4, Jan. 2002.
Brand and Wheeler, "KRAS mutant colorectal tumors: past and present," *Small GTPases.*, 3(1):34-39, Jan.-Mar. 2012.
Carley and Severson, "Fatty acid metabolism is enhanced in type 2 diabetic hearts," *Biochim. Biophys Acta.*, 1734(2):112-126, Epub Apr. 9, 2005.
Chetty and Govender, "Gene of the month: KRAS," *J Clin Pathol.*, 66(7):548-550, Epub Apr. 27, 2013.

(Continued)

*Primary Examiner* — Aaron J Kosar
(74) *Attorney, Agent, or Firm* — Fish & Richardson P.C.

(57) ABSTRACT

This document provides methods and materials for treating diabetes and/or liver steatosis. For example, methods for using compositions containing a potato polysaccharide preparation to reduce one or more symptoms of diabetes or liver steatosis are provided. In some cases, a composition containing a potato polysaccharide preparation provided herein can be used to treat fatty liver disease.

16 Claims, 49 Drawing Sheets

(56) References Cited

FOREIGN PATENT DOCUMENTS

| | | |
|---|---|---|
| JP | 2006/321784 | 11/2006 |
| JP | 2007/024871 | 2/2007 |
| JP | 2007/509178 | 4/2007 |
| JP | 2009/007309 | 1/2009 |
| JP | 2012-149004 | 8/2012 |
| JP | 2014-532712 | 12/2014 |
| KR | 101093413 | 12/2011 |
| WO | WO 1998/033494 | 8/1998 |
| WO | WO 2002/22111 | 3/2002 |
| WO | WO 2005/039539 | 5/2005 |
| WO | WO 2006114019 | 11/2006 |
| WO | WO 2011069781 | 6/2011 |
| WO | WO 2012016050 | 2/2012 |
| WO | WO 2013/040316 | 3/2013 |
| WO | WO 2013040316 | 3/2013 |
| WO | WO 2013/148282 | 10/2013 |
| WO | WO 2013148282 | 10/2013 |
| WO | WO 2014/051076 | 4/2014 |
| WO | WO 2014/200969 | 12/2014 |
| WO | WO 2017160678 | 9/2017 |

OTHER PUBLICATIONS

Congiu et al., "Expression of common housekeeping genes is affected by disease in human hepatitis C virus-infected liver," *Liver Int.*, 31(3):386-390, Epub Nov. 15, 2010.

Constantin-Teodosiu et al., "The role of FOXO and PPAR transcription factors in diet-mediated inhibition of PDC activation and carbohydrate oxidation during exercise in humans and the role of pharmacological activation of PDC in overriding these changes," *Diabetes*, 61(5):1017-1024, Epub Feb. 7, 2012.

Cooper et al., "Molecular biology of lung cancer," *J Thorac Dis.*, 5 Suppl 5:S479-S490, Oct. 2013.

De la Torre and Stefano, "Evidence that Alzheimer's disease is a microvascular disorder: the role of constitutive nitric oxide," *Brain Res Brain Res Rev.*, 34(3):119-136, Dec. 2000.

De la Torre, "Alzheimer's disease is a vasocognopathy: a new term to describe its nature," *Neurol Res.*, 26(5):517-524, Jul. 2004.

De la Torre, "Is Alzheimer's disease a neurodegenerative or a vascular disorder? Data, dogma, and dialectics," *Lancet Neurol.*, 3(3):184-190, Mar. 2004.

Deane et al., "Clearance of amyloid-beta peptide across the blood-brain barrier: implication for therapies in Alzheimer's disease," *CNS Neurol Disord Drug Targets*, 8(1):16-30, Mar. 2009.

Di Magliano and Logsdon, "Roles for KRAS in pancreatic tumor development and progression," *Gastroenterology*, 144(6):1220-1229, Jun. 2013.

Ekstrand et al., "Mitochondrial transcription factor A regulates mtDNA copy number in mammals," *Hum Mol Genet.*, 13(9):935-944, Epub Mar. 11, 2004.

Franks et al., "Viral p21 Ki-RAS protein: a potent intracellular mitogen that stimulates adenylate cyclase activity in early G1 phase of cultured rat cells," *J Cell Biochem.*, 33(2):87-94, Feb. 1987.

Freude et al., "Neuronal IGF-1 resistance reduces Abeta accumulation and protects against premature death in a model of Alzheimer's disease," *Faseb J.*, 23(10):3315-3324, Epub Jun. 1, 2009.

Friedman, "Analysis of biologically active compounds in potatoes (*Solanum tuberosum*), tomatoes (*Lycopersicon esculentum*), and jimson weed (*Datum stramonium*) seeds," *J Chromatogr A.*, 1054(1-2):143-155, Oct. 29, 2004.

Friedman, "Potato glycoalkaloids and metabolites: roles in the plant and in the diet," *J Agric Food. Chem.*, 54(23):8655-8681, Nov. 15, 2006.

Galperin et al., "Shoc2 is targeted to late endosomes and required for Erk1/2 activation in EGF-stimulated cells," *PLoS One*, 7(5):e36469, Epub May 14, 2012.

Gao et al., "Effect of solanine on the membrane potential of mitochondria in HepG2 cells and [Ca2+]i in the cells," *World J Gastroenterol.*, 12(21):3359-3367, Jun. 7, 2006.

GenBank® Accession No. AAA52712.1 (GI No. 184556) "insulin-degrading enzyme [*Homo sapiens*]" Nov. 8, 1994, 2 pages.

GenBank® Accession No. AAD13528.1 (GI No. 4240387) "PTEN [*Homo sapiens*]" 1 page, Feb. 8, 1999.

GenBank® Accession No. AAD24775.1 (GI No. 4581877) "proline dehydrogenase [*Homo sapiens*]" 1 page, Apr. 13, 1999.

GenBank® Accession No. AAH00408.1 (GI No. 12653279) "ACAT2 protein [*Homo sapiens*]" 2 pages, Jun. 9, 2008.

GenBank® Accession No. AAH00484.1 (GI No. 12653427) "UQCRC2 protein [*Homo sapiens*]" 2 pages, Aug. 3, 2004.

GenBank® Accession No. AAH00583.2 (GI No. 38014202) "THOP1 protein, partial [*Homo sapiens*]" 2 pages, Nov. 4, 2003.

GenBank® Accession No. AAH04243.2 (GI No. 48257075) "BCAT2 protein, partial [*Homo sapiens*]" 2 pages, Jun. 4, 2004.

GenBank® Accession No. AAH04905.2 (GI No. 33872889) "MRPS2 protein [*Homo sapiens*]" 2 pages, Sep. 16, 2003.

GenBank® Accession No. AAH08028.2 (GI No. 34782901) "ATP5A1 protein, partial [*Homo sapiens*]" 2 pages, Jan. 19, 2006.

GenBank® Accession No. AAH10704.1 (GI No. 14715079) "SH2B1 protein [*Homo sapiens*]" 2 pages, Jul. 24, 2006.

GenBank® Accession No. AAH13410.1 (GI No. 38196950) "AGPAT4 protein, partial [*Homo sapiens*]" 2 pages, Jul. 28, 2005.

GenBank® Accession No. AAH16934.1 (GI No. 16877367) "SOD2 protein [*Homo sapiens*]" 2 pages, Oct. 7, 2003.

GenBank® Accession No. AAH20695.1 (GI No. 116283350) "CPS1 protein, partial [*Homo sapiens*]" 2 pages, Sep. 11, 2007.

GenBank® Accession No. AAH22071.1 (GI No. 34784795) "Glutathione peroxidase 4 (phospholipid hydroperoxidase) [*Homo sapiens*]" Jul. 17, 2006, 2 pages.

GenBank® Accession No. AAH31485.1 (GI No. 32425437) "ACACA protein, partial [*Homo sapiens*]" 2 pages, Jan. 6, 2005.

GenBank® Accession No. AAH33692.1 (GI No. 21707182) "HMGCR protein [*Homo sapiens*]" 2 pages, Sep. 1, 2006.

GenBank® Accession No. AAH40239.1 (GI No. 25955471) "PDK4 protein [*Homo sapiens*]" 2 pages, Jun. 19, 2006.

GenBank® Accession No. AAH41143.1 (GI No. 26996542) "ACBD4 protein [*Homo sapiens*]" 2 pages, Nov. 19, 2003.

GenBank® Accession No. AAH47528.1 (GI No. 28839408) "TOMM40 protein [*Homo sapiens*]" 2 pages, Jul. 28, 2005.

GenBank® Accession No. AAH47784.1 (GI No. 29126836) "MRPS9 protein, partial [*Homo sapiens*]" 2 pages, Sep. 16, 2003.

GenBank® Accession No. AAH68050.1 (GI No. 45751586) "CASP8 protein [*Homo sapiens*]" 2 pages, Sep. 9, 2005.

GenBank® Accession No. AAH70041.1 (GI No. 47124456) "Lipase, hormone-sensitive [*Homo sapiens*]" 2 pages, Jul. 17, 2006.

GenBank® Accession No. AAH94760.1 (GI No. 66267554) "PDHA2 protein, partial [*Homo sapiens*]" 2 pages, May 27, 2005.

GenBank® Accession No. AAI30284.1 (GI No. 120660146) "Nitric oxide synthase 2, inducible [*Homo sapiens*]" Mar. 18, 2009, 3 pages.

GenBank® Accession No. AAI44252.1 (GI No. 219518198) "PPARGC1B protein [*Homo sapiens*]" 2 pages, Mar. 18, 2009.

GenBank® Accession No. ABD77240.1 (GI No. 89574029) "mitochondrial ATP synthase, H+ transporting F1 complex beta subunit, partial [*Homo sapiens*]" 1 page, Jul. 18, 2006.

GenBank® Accession No. ABQ58815.1 (GI No. 148300624) "PDHA1 partial [*Homo sapiens*]" 1 page, May 30, 2007.

GenBank® Accession No. ACN89883.1 (GI No. 225421341) "mitochondrial aldehyde dehydrogenase 4 family member A1 transcript variant ALDH4A1_v6 [*Homo sapiens*]" 1 page, Jan. 1, 2010.

GenBank® Accession No. AFL91689.1 (GI No. 390432195) "fatty acid desaturase 1, partial [*Homo sapiens*]" 1 page, Aug. 28, 2012.

GenBank® Accession No. AK314199.1 (GI No. 164697148) "*Homo sapiens* cDNA, FLJ94925, Homo sapiens fatty acid desaturase 1 (FADS1), mRNA" 2 pages, May 24, 2008.

GenBank® Accession No. BAD13700.1 (GI No. 46091143) "MRPS18B protein [*Homo sapiens*]" 1 page, Sep. 13, 2006.

GenBank® Accession No. CAB94757.1 (GI No. 8574070) "NFKB1 [*Homo sapiens*]" 2 pages, Nov. 14, 2006.

GenBank® Accession No. CAG28581.1 (GI No. 47115243) "TFAM, partial [*Homo sapiens*]" 2 pages, Oct. 16, 2008.

GenBank® Accession No. CAG28601.1 (GI No. 47115283) "ILK, partial [*Homo sapiens*]," May 10, 2014, 2 pages.

(56) References Cited

OTHER PUBLICATIONS

GenBank® Accession No. CAG32985.1 (GI No. 48145525) "NR4A1 [*Homo sapiens*]" 2 pages, Oct. 16, 2008.
GenBank® Accession No. CAG33001.1 (GI No. 48145557) "MRPL3 [*Homo sapiens*]" 2 pages, Oct. 16, 2008.
GenBank® Accession No. CAG33165.1 (GI No. 48145885) "HMGCL [*Homo sapiens*]" 2 pages, Oct. 16, 2008.
GenBank® Accession No. CAG33194.1 (GI No. 48145943) "PCK2 [*Homo sapiens*]" 2 pages, Oct. 16, 2008.
GenBank® Accession No. CAG33335.1 (GI No. 4814622) "LPL [*Homo sapiens*]" 2 pages, Oct. 16, 2008.
GenBank® Accession No. CAG33384.1 (GI No. 48146323) "LYPLA1 [*Homo sapiens*]" 2 pages, Oct. 16, 2008.
GenBank® Accession No. CAG33458.1 (GI No. 48146471) "MRPL17 [*Homo sapiens*]" 2 pages, Oct. 16, 2008.
GenBank® Accession No. CAG38562.1 (GI No. 49065488) "MRPL15 [*Homo sapiens*]" 2 pages, Oct. 16, 2008.
GenBank® Accession No. CAG38785.1 (GI No. 49168580) "MDH2 [*Homo sapiens*]" 2 pages, Oct. 16, 2008.
GenBank® Accession No. CR457103.1 (GI No. 48146322) "*Homo sapiens* full open reading frame cDNA clone RZPDo834G067D for gene LYPLA1, lysophospholipase I; complete cds, incl. stopcodon" 2 pages, Oct. 16, 2008.
GenBank® Accession No. CR536548.1 (GI No. 49168579) "*Homo sapiens* full open reading frame cDNA clone RZPDo834E0920D for gene MDH2, malate dehydrogenase 2, NAD (mitochondrial); complete cds, incl. stopcodon" 2 pages, Oct. 16, 2008.
GenBank® Accession No. FJ462711.1 (GI No. 225421340) "*Homo sapiens* mitochondrial aldehyde dehydrogenase 4 family member A1 transcript variant ALDH4A1_v6 (ALDH4A1) mRNA, complete cds; nuclear gene for mitochondrial product," 2 pages, Jan. 1, 2010.
GenBank® Accession No. NC_000005.10 (GI No. 568815593) "*Homo sapiens* chromosome 5, GRCh38 Primary Assembly" Feb. 3, 2014, 2 pages.
GenBank® Accession No. NC_000012.12 (GI No. 568815586) "*Homo sapiens* chromosome 12, GRCh38 Primary Assembly," Feb. 3, 2014, 3 pages.
GenBank® Accession No. NC_000019.10 (GI No. 568815579) "*Homo sapiens* chromosome 19, GRCh38 Primary Assembly," Feb. 3, 2014, 2 pages.
GenBank® Accession No. NG_011470.1 (GI No. 22480926) "*Homo sapiens* nitric oxide synthase 2, inducible (NOS2), RefSeqGene on chromosome 17," Mar. 24, 2014, 15 pages.
GenBank® Accession No. NG_013012.1 (GI No. 260593646) "*Homo sapiens* insulin-degrading enzyme (IDE), RefSeqGene on chromosome 10," Mar. 13, 2014, 32 pages.
GenBank® Accession No. NG_016444 (GI No. 284813599) "*Homo sapiens* low density lipoprotein receptor-related protein 1 (LRP1), RefSeqGene on chromosome 12" Feb. 23, 2014, 32 pages.
GenBank® Accession No. NG_029469 (GI No. 340523104) "*Homo sapiens* heat shock 70kDa protein 9 (mortalin) (HSPA9), RefSeqGene on chromosome 5," Feb. 18, 2014, 10 pages.
GenBank® Accession No. NG_029615.1 (GI No. 342349296) "*Homo sapiens* amyloid beta (A4) precursor protein-binding, family B, member 1 (Fe65) (APBB1), RefSeqGene on chromosome 11," Feb. 18, 2014, 11 pages.
GenBank® Accession No. NM_000098.2 (GI No. 169790951) "*Homo sapiens* carnitine palmitoyltransferase 2 (CPT2), mRNA" 4 pages, May 3, 2014.
GenBank® Accession No. NM_000191.2 (GI No. 62198231) "*Homo sapiens* 3-hydroxymethyl-3-methylglutaryl-CoA lyase (HMGCL), transcript variant 1, mRNA" 4 pages, May 10, 2014.
GenBank® Accession No. NM_000237.1 (GI No. 145275217) "*Homo sapiens* lipoprotein lipase (LPL), mRNA" 4 pages, Apr. 1, 2007.
GenBank® Accession No. NM_000314.2 (GI No. 110224474) "*Homo sapiens* phosphatase and tensin homolog (mutated in multiple advanced cancers 1) (PTEN), mRNA" 24 pages, Aug. 8, 2005.
GenBank® Accession No. NM_000636.1 (GI No. 67782304) "*Homo sapiens* superoxide dismutase 2, mitochondrial (SOD2), mRNA" 10 pages, May 16, 2005.
GenBank® Accession No. NM_000859.2 (GI No. 196049378) "*Homo sapiens* 3-hydroxy-3-methylglutaryl-CoA reductase (HMGCR), transcript variant 1, mRNA" 7 pages, May 25, 2014.
GenBank® Accession No. NM_001001937.1 (GI No. 50345983) "*Homo sapiens* ATP synthase, H+ transporting, mitochondrial F1 complex, alpha subunit 1, cardiac muscle (ATP5A1), nuclear gene encoding mitochondrial protein, transcript variant 1, mRNA" 6 pages, Mar. 11, 2011.
GenBank® Accession No. NM_001014794.2 (GI No. 510785737) "*Homo sapiens* integrin-linked kinase (ILK), transcript variant 2, mRNA," 5 pages.
GenBank® Accession No. NM_001122633.2 (GI No. 327532712) "*Homo sapiens* carbamoyl-phosphate synthase 1, mitochondrial (CPS1), nuclear gene encoding mitochondrial protein, transcript variant 1, mRNA" 7 pages, Mar. 20, 2011.
GenBank® Accession No. NM_001126121.1 (GI No. 186928857) "*Homo sapiens* solute carrier family 25 (mitochondrial thiamine pyrophosphate carrier), member 19 (SLC25A19), nuclear gene encoding mitochondrial protein, transcript variant 1, mRNA" 5 pages, Mar. 11, 2011.
GenBank® Accession No. NM_001128916.1 (GI No. 193083119) "*Homo sapiens* translocase of outer mitochondrial membrane 40 homolog (yeast) (TOMM40), nuclear gene encoding mitochondrial protein, transcript variant 2, mRNA" 4 pages, Mar. 11, 2011.
GenBank® Accession No. NM_001130996.1 (GI No. 196049379) "*Homo sapiens* 3-hydroxy-3-methylglutaryl-CoA reductase (HMGCR), transcript variant 2, mRNA" 6 pages, Mar. 20, 2011.
GenBank® Accession No. NM_001135704.1 (GI No. 209364588) "*Homo sapiens* acyl-CoA binding domain containing 4 (ACBD4), transcript variant 1, mRNA" 4 pages, May 15, 2011.
GenBank® Accession No. NM_001145797.1 (GI No. 224926829) "*Homo sapiens* SH2B adaptor protein 1 (SH2B1), transcript variant 5, mRNA" 7 pages, Mar. 12, 2011.
GenBank® Accession No. NM_001165412.1 (GI No. 25955301) "*Homo sapiens* nuclear factor of kappa light polypeptide gene enhancer in B-cells 1 (NFKB1), transcript variant 2, mRNA" 7 pages, May 22, 2011.
GenBank® Accession No. NM_001173454.1 (GI No. 291084741) "*Homo sapiens* pyruvate dehydrogenase (lipoamide) alpha 1 (PDHA1), nuclear gene encoding mitochondrial protein, transcript variant 2, mRNA" Mar. 11, 2011, 5 pages.
GenBank® Accession No. NM_001190.1 (GI No. 258614013) "*Homo sapiens* branched chain aminotransferase 2, mitochondrial (BCAT2), mRNA" 3 pages, Dec. 23, 2003.
GenBank® Accession No. NM_001191060.1 (GI No. 300796969) "*Homo sapiens* solute carrier family 25 (mitochondrial carrier: glutamate), member 22 (SLC25A22), nuclear gene encoding mitochondrial protein, transcript variant 1, mRNA" 4 pages, Mar. 11, 2011.
GenBank® Accession No. NM_001228.4 (GI No. 122056470) "*Homo sapiens* caspase 8, apoptosis-related cysteine peptidase (CASP8), transcript variant A, mRNA" 5 pages, Mar. 19, 2011.
GenBank® Accession No. NM_001269039.1 (GI No. 392841223) "*Homo sapiens* soc-2 suppressor of clear homolog (C. elegans) (SHOC2), transcript variant 2, mRNA," Mar. 16, 2014, 5 pages.
GenBank® Accession No. NM_001686.3 (GI No. 50345985) "*Homo sapiens* ATP synthase, H+ transporting, mitochondrial F1 complex, beta polypeptide (ATP5B), mRNA" 4 pages, Feb. 27, 2011.
GenBank® Accession No. NM_002015.3 (GI No. 133930787) "*Homo sapiens* forkhead box O1 (FOXO1), mRNA" 5 pages, Mar. 13, 2011.
GenBank® Accession No. NM_002543.2 (GI No. 119392084) "*Homo sapiens* oxidised low density lipoprotein (lectin-like) receptor 1 (OLR1), mRNA" 4 pages, Nov. 17, 2006.
GenBank® Accession No. NM_002611.4 (GI No. 315630394) "*Homo sapiens* pyruvate dehydrogenase kinase, isozyme 2 (PDK2), nuclear gene encoding mitochondrial protein, transcript variant 1, mRNA" 4 pages, Mar. 11, 2011.

(56) References Cited

OTHER PUBLICATIONS

GenBank® Accession No. NM_002612.2 (GI No. 94421466) "*Homo sapiens* pyruvate dehydrogenase kinase, isozyme 4 (PDK4), mRNA" 4 pages, Apr. 16, 2011.
GenBank® Accession No. NM_003201.1 (GI No. 4507400) "*Homo sapiens* transcription factor A, mitochondrial (TFAM), nuclear gene encoding mitochondrial protein, mRNA" 4 pages, Mar. 11, 2011.
GenBank® Accession No. NM_003249.3 (GI No. 34222291) "*Homo sapiens* thimet oligopeptidase 1 (THOP1), mRNA" 4 pages, Mar. 13, 2011.
GenBank® Accession No. NM_003366.2 (GI No. 50592987) "*Homo sapiens* ubiquinol-cytochrome c reductase core protein II (UQCRC2), nuclear gene encoding mitochondrial protein, mRNA" 4 pages, Mar. 10, 2011.
GenBank® Accession No. NM_004563.1 (GI No. 66346720) "*Homo sapiens* phosphoenolpyruvate carboxykinase 2 (mitochondrial) (PCK2), mRNA" 3 pages, Apr. 22, 2005.
GenBank® Accession No. NM_004976.2 (GI No. 15718761) "GTPase KRas isoform b [*Homo sapiens*]," Mar. 16, 2014, 3 pages.
GenBank® Accession No. NM_004985.3 (GI No. 34485723) "*Homo sapiens* Kirsten rat sarcoma viral oncogene homolog (KRAS), transcript variant b, mRNA," Jan. 19, 2014, 6 pages.
GenBank® Accession No. NM_005357.2 (GI No. 21328445) "*Homo sapiens* lipase, hormone-sensitive (LIPE), mRNA" 5 pages, Mar. 12, 2011.
GenBank® Accession No. NM_005390.4 (GI No. 134031963) "*Homo sapiens* pyruvate dehydrogenase (lipoamide) alpha 2 (PDHA2), mRNA" 3 pages, Mar. 12, 2011.
GenBank® Accession No. NM_005891.1 (GI No. 148539871) "*Homo sapiens* acetyl-Coenzyme A acetyltransferase 2 (acetoacetyl Coenzyme A thiolase) (ACAT2), mRNA" 3 pages, Apr. 15, 2007.
GenBank® Accession No. NM_005984.3 (GI No. 374713106) "*Homo sapiens* solute carrier family 25 (mitochondrial carrier; citrate transporter), member 1 (SLC25A1), nuclear gene encoding mitochondrial protein, transcript variant 1, mRNA" 5 pages, Mar. 13, 2011.
GenBank® Accession No. NM_006411.3 (GI No. 301336168) "*Homo sapiens* 1-acylglycerol-3-phosphate O-acyltransferase 1 (lysophosphatidic acid acyltransferase, alpha) (AGPAT1), transcript variant 1, mRNA" 5 pages, Mar. 13, 2011.
GenBank® Accession No. NM_006567.3 (GI No. 126513133) "*Homo sapiens* phenylalanyl-tRNA synthetase 2, mitochondrial (FARS2), nuclear gene encoding mitochondrial protein, mRNA" 5 pages, Mar. 10, 2011.
GenBank® Accession No. NM_007189.2 (GI No. 525345247) "*Homo sapiens* ATP-binding cassette, sub-family F (GCN20), member 2 (ABCF2), nuclear gene encoding mitochondrial protein, transcript variant 1, mRNA" 5 pages, Mar. 12, 2011.
GenBank® Accession No. NM_013261.2 (GI No. 116284374) "*Homo sapiens* peroxisome proliferative activated receptor, gamma, coactivator 1, alpha (PPARGC1A), mRNA" 14 pages, Sep. 24, 2006.
GenBank® Accession No. NM_014046.3 (GI No. 186928836) "*Homo sapiens* mitochondrial ribosomal protein S18B (MRPS18B), nuclear gene encoding mitochondrial protein, mRNA" 4 pages, Mar. 13, 2011.
GenBank® Accession No. NM_014236.3 (GI No. 170650722) "*Homo sapiens* glyceronephosphate O-acyltransferase (GNPAT), mRNA" 4 pages, Mar. 11, 2011.
GenBank® Accession No. NM_016034.4 (GI No. 389565494) "*Homo sapiens* mitochondrial ribosomal protein S2 (MRPS2), nuclear gene encoding mitochondrial protein, mRNA" 3 pages, Mar. 10, 2011.
GenBank® Accession No. NM_016070.3 (GI No. 312222785) "*Homo sapiens* mitochondrial ribosomal protein S23 (MRPS23), nuclear gene encoding mitochondrial protein, mRNA" 3 pages, Mar. 13, 2011.
GenBank® Accession No. NM_016335.4 (GI No. 304766735) "*Homo sapiens* proline dehydrogenase (oxidase) 1 (PRODH), nuclear gene encoding mitochondrial protein, transcript variant 1, mRNA" 5 pages, Mar. 11, 2011.
GenBank® Accession No. NM_022061.3 (GI No. 169403966) "*Homo sapiens* mitochondrial ribosomal protein L17 (MRPL17), nuclear gene encoding mitochondrial protein, mRNA" 4 pages, Mar. 12, 2011.
GenBank® Accession No. NM_058165.1 (GI No. 148746190) "*Homo sapiens* monoacylglycerol O-acyltransferase 1 (MOGAT1), mRNA" 2 pages, Jun. 3, 2007.
GenBank® Accession No. NM_133263.2 (GI No. 289577087) "*Homo sapiens* peroxisome proliferator-activated receptor gamma, coactivator 1 beta (PPARGC1B), mRNA" 4 pages, Feb. 14, 2010.
GenBank® Accession No. NM_173158.1 (GI No. 320202954) "*Homo sapiens* nuclear receptor subfamily 4, group A, member 1 (NR4A1), transcript variant 3, mRNA" 3 pages, Feb. 18, 2007.
GenBank® Accession No. NM_182640.2 (GI No. 186910309) "*Homo sapiens* mitochondrial ribosomal protein S9 (MRPS9), nuclear gene encoding mitochondrial protein, mRNA" 4 pages, Mar. 12, 2011.
GenBank® Accession No. NP_000089.1 (GI No. 4503023) "carnitine O-palmitoyltransferase 2, mitochondrial precursor [*Homo sapiens*]" 3 pages, Mar. 12, 2011.
GenBank® Accession No. NP_001104753.1 (GI No. 163659899) "insulin-like growth factor I isoform 1 preproprotein [*Homo sapiens*]" Mar. 23, 2014, 3 pages.
GenBank® Accession No. NP_001119594.1 (GI No. 186928860) "mitochondrial thiamine pyrophosphate carrier [*Homo sapiens*]" 3 pages, Mar. 12, 2011.
GenBank® Accession No. NP_001177990.1 (GI No. 300796991) "mitochondrial glutamate carrier 1 [*Homo sapiens*]" 2 pages, Mar. 11, 2011.
GenBank® Accession No. NP_002006.2 (GI No. 9257222) "forkhead box protein O1 [*Homo sapiens*]" 3 pages, Mar. 13, 2011.
GenBank® Accession No. NP_002075.2 (GI No. 6006001) "glutathione peroxidase 3 precursor [*Homo sapiens*]" Mar. 16, 2014, 3 pages.
GenBank® Accession No. NP_002323.2 (GI No. 126012562) "prolow-density lipoprotein receptor-related protein 1 precursor [*Homo sapiens*]" Feb. 22, 2014, 7 pages.
GenBank® Accession No. NP_002534.1 (GI No. 4505501) "oxidized low-density lipoprotein receptor 1 isoform 1 [*Homo sapiens*]" 3 pages, Mar. 20, 2011.
GenBank® Accession No. NP_002602.2 (GI No. 19923736) "pyruvate dehydrogenase kinase, isozyme 2 isoform 1 precursor [*Homo sapiens*]" 3 pages, Mar. 11, 2011.
GenBank® Accession No. NP_004125.3 (GI No. 24234688) "stress-70 protein, mitochondrial precursor [*Homo sapiens*]" Feb. 27, 2014, 4 pages.
GenBank® Accession No. NP_005975.1 (GI No. 21389315) "tricarboxylate transport protein, mitochondrial precursor [*Homo sapiens*]" 3 pages, Mar. 13, 2011.
GenBank® Accession No. NP_006558.1 (GI No. 5729820) "phenylalanyl-tRNA synthetase, mitochondrial precursor [*Homo sapiens*]" 3 pages, Mar. 10, 2011.
GenBank® Accession No. NP_009120.1 (GI No. 27881506) "ATP-binding cassette sub-family F member 2 isoform a [*Homo sapiens*]" 3 pages, Mar. 12, 2011.
GenBank® Accession No. NP_031399.2 (GI No. 41281398) "leucine-rich repeat protein SHOC-2 isoform 1 [*Homo sapiens*]," Mar. 2, 2014, 5 pages.
GenBank® Accession No. NP_033360.2 (GI No. 34485724) "*Homo sapiens* Kirsten rat sarcoma viral oncogene homolog (KRAS), transcript variant a, mRNA," Jan. 11, 2014, 7 pages.
GenBank® Accession No. NP_037393.1 (GI No. 7019499) "peroxisome proliferator-activated receptor gamma coactivator 1-alpha [*Homo sapiens*]" 3 pages, Mar. 25, 2011.
GenBank® Accession No. NP_055051.1 (GI No. 7657134) "dihydroxyacetone phosphate acyltransferase [*Homo sapiens*]" 3 pages, Mar. 11, 2011.
GenBank® Accession No. NP_057154.2 (GI No. 16554604) "28S ribosomal protein S23, mitochondrial [*Homo sapiens*]" 2 pages, Mar. 13, 2011.

(56) References Cited

OTHER PUBLICATIONS

GenBank® Accession No. NP_116130.2 (GI No. 15100175) "1-acyl-sn-glycerol-3-phosphate acyltransferase alpha [*Homo sapiens*]" 3 pages, Mar. 11, 2011.
GenBank® Accession No. NP_203524.1 (GI No. 15718763) "GTPase KRas isoform a [*Homo sapiens*]," Mar. 16, 2014, 4 pages.
GenBank® Accession No. NP_477513.2 (GI No. 148746191) "2-acylglycerol O-acyltransferase 1 [*Homo sapiens*]" 2 pages, Dec. 26, 2010.
GenBank® Accession No. XM_005253365.1 (GI No. 530399132) "Predicted: *Homo sapiens* Kirsten rat sarcoma viral oncogene homolog (KRAS), transcript variant X1, mRNA" Aug. 13, 2013, 2 pages.
GenBank® Accession No. XM_005257266.1 (GI No. 530412017) "Predicted: *Homo sapiens* acetyl-CoA carboxylase alpha (ACACA), transcript variant X1, mRNA" 4 pages, Aug. 13, 2013.
GenBank® Accession No. XM_005263503.1 (GI No. 530360654) "Predicted: *Homo sapiens* solute carrier family 25 (pyrimidine nucleotide carrier), member 33 (SLC25A33), transcript variant X1, mRNA" 2 pages, Aug. 13, 2013.
GenBank® Accession No. XM_005267052.1 (GI No. 530383869) "Predicted: *Homo sapiens* 1-acylglycerol-3-phosphate O-acyltransferase 4 (AGPAT4), transcript variant X1, mRNA" 3 pages, Aug. 13, 2013.
GenBank® Accession No. XP_005253422.1 (GI No. 530399133) "Predicted: GTPase KRas isoform X1 [*Homo sapiens*]" Aug. 13, 2013, 2 pages.
GenBank® Accession No. XP_005263560.1 (GI No. 530360655) "Predicted: solute carrier family 25 member 33 isoform X1 [*Homo sapiens*]" 1 page, Aug. 13, 2013.
Goffin and Zbuk, "Epidermal growth factor receptor: pathway, therapies, and pipeline," *Clin Ther.*, 35(9):1282-1303, Sep. 2013.
Gutscher et al., "Proximity-based protein thiol oxidation by H2O2-scavenging peroxidases," *J Biol. Chem.*, 284(46):31532-31540, Epub Sep. 15, 2009.
Hatzivassiliou et al., "Mechanism of MEK inhibition determines efficacy in mutant KRAS-versus BRAF-driven cancers," *Nature*, 501(7466):232-236, Epub Aug. 11, 2013.
Huang et al., "Pleurotus tuber-regium Polysaccharides Attenuate Hyperglycemia and Oxidative Stress in Experimental Diabetic Rats," *Evid Based Complement Alternat Med.*, 2012:856381, Epub. Aug. 30, 2012.
Iablokov et al., "Naturally occurring glycoalkaloids in potatoes aggravate intestinal inflammation in two mouse models of inflammatory bowel disease," *Dig Dis Sci.*, 55(11):3078-3085, Epub Mar. 3, 2010.
Ikeuchi et al., Overexpression of mitochondrial transcription factor a ameliorates mitochondrial deficiencies and cardiac failure after myocardial infarction, *Circulation*, 112(5):683-690, Epub Jul.25, 2005.
Jaeger and Pietrzik, "Functional role of lipoprotein receptors in Alzheimer's disease," *Curr. Alzheimer Res.*, 5(1):15-25, Feb. 2008.
Jongmans et al., "Noonan syndrome, the SOS1 gene and embryonal rhabdomyosarcoma," *Genes Chromosomes Cancer*, 49(7):635-641, Jul. 2010.
Ju et al., "Anti-obesity and antioxidative effects of purple sweet potato extract in 3T3-L1 adipocytes in vitro," *J Med Food.*, 14(10):1097-106, Epub Aug. 23, 2011.
Kakimoto et al., "Automated recognition and quantification of pancreatic islets in Zucker diabetic fatty rats treated with exendin-4," *J Endocrinol.*, 216(1):13-20, Jan. 2, 2013.
Kang et al., "Mitochondrial transcription factor A (TFAM): roles in maintenance of mtDNA and cellular functions," *Mitochondrion*, 7(1-2):39-44, Epub Dec. 8, 2006.
Kodamatani et al., "Simple and sensitive method for determination of glycoalkaloids in potato tubers by high-performance liquid chromatography with chemiluminescence detection," *J Chromatogr A.*, 1100(1):26-31, Epub Sep. 27, 2005.
Köhler and Schuler, "Afatinib, erlotinib and gefitinib in the first-line therapy of EGFR mutation-positive lung adenocarcinoma: a review," *Onkologie*, 36(9):510-518, Epub Aug. 19, 2013.

Kovalevich and Langford, "Considerations for the use of SH-SY5Y neuroblastoma cells in neurobiology," *Methods Mol Biol.*, 1078:9-21, 2013.
Kummer et al., "Nitric oxide decreases the enzymatic activity of insulin degrading enzyme in APP/PS1 mice," *J Neuroimmune Pharmacol.*, 7(1):165-172, Epub Jan. 8, 2012.
Kusano and Abe, "Antidiabetic activity of white skinned sweet potato (*Ipomoea batatas* L.) in obese Zucker fatty rats," *Biol Pharm Bull.*, 23(1):23-26, Jan. 2000.
Langkilde et al., "A 28-day repeat dose toxicity study of steroidal glycoalkaloids, alpha-solanine and alpha-chaconine in the Syrian Golden hamster," *Food Chem Toxicol.*, 47(6):1099-1108, Epub Feb. 13, 2009.
Lee et al., "Dysregulation of adipose glutathione peroxidase 3 in obesity contributes to local and systemic oxidative stress," *Mol Endocrinol.*, 22(9):2176-2189, Epub Jun. 18, 2008.
Li et al., "Insulin and insulin-like growth factor-I receptors differentially mediate insulin-stimulated adhesion molecule production by endothelial cells," *Endocrinology*, 150(8):3475-3482, Epub May 7, 2009.
Love et al., "The relationship between human skeletal muscle pyruvate dehydrogenase phosphatase activity and muscle aerobic capacity," *J Appl Physiol (1985)*, 111(2):427-434, Epub May 19, 2011.
Lu et al., "α-Solanine inhibits human melanoma cell migration and invasion by reducing matrix metalloproteinase-2/9 activities," *Biol Pharm Bull.*, 33(10):1685-1691, 2010.
Ludvik et al., "Efficacy of Ipomoea batatas (Caiapo) on diabetes control in type 2 diabetic subjects treated with diet," *Diabetes Care*, 27(2):436-440, Feb. 2004.
Mandimika et al., "Differential gene expression in intestinal epithelial cells induced by single and mixtures of potato glycoalkaloids," *J Agric Food Chem.*, 28;55(24):10055-10066, Epub Nov. 1, 2007.
Mantione et al., "Endogenous morphine signaling via nitric oxide regulates the expression of CYP2D6 and COMT: autocrine/paracrine feedback inhibition," *Addict Biol.*, 13(1):118-123, Epub. Jun 16, 2007.
Mantione et al., "Identification of a μ opiate receptor signaling mechanism in human placenta," *Med. Sci Monit.*, 16(11):BR347-BR352, Nov. 2010.
Martin et al., "KRAS mutations as prognostic and predictive markers in non-small cell lung cancer," *J Thorac Oncol.*, 8(5):530-542, May 2013.
Matsuda et al., "Determination of potato glycoalkaloids using high-pressure liquid chromatography-electrospray ionisation/mass spectrometry," *Phytochem Anal.*, 15(2):121-124, Mar.-Apr. 2004.
McGehee et al., "Cholinesterase inhibition by potato glycoalkaloids slows mivacurium metabolism," *Anesthesiology.*, 93(2):510-519, Aug. 2000.
McLoughlin and Miller, "The FE65 proteins and Alzheimer's disease," *J Neurosci Res.*, 86(4):744-754, Mar. 2008.
Miners et al., "Aβ-degrading enzymes: potential for treatment of Alzheimer disease," *J Neuropathol Exp Neurol.*, 70(11):944-959, Nov. 2011.
Minuti et al., "Targeted therapy for NSCLC with driver mutations," *Expert Opin Biol Ther.*, 13(10):1401-1412, Oct. 2013.
Murray, Encyclopedia of Nutritional Supplements, pp. 44-53 and pp. 343-346, 1996.
Nakajima et al., "Potato extract (Potein) suppresses food intake in rats through inhibition of luminal trypsin activity and direct stimulation of cholecystokinin secretion from enteroendocrine cells," *J. Agric Food Chem.*, 59(17):9491-9496, Epub Aug. 16, 2011.
Neant-Fery et al., "Molecular basis for the thiol sensitivity of insulin-degrading enzyme," *Proc Natl Acad Sci U S A.*, 105(28):9582-9587, Epub Jul. 8, 2008.
Otto et al., "Longitudinal study of painful diabetic neuropathy in the Zucker diabetic fatty rat model of type 2 diabetes: impaired basal G-protein activity appears to underpin marked morphine hyposensitivity at 6 months," *Pain Med.*, 12(3):437-50. Epub Feb. 18, 2011.
Pandini et al., "Insulin has multiple antiamyloidogenic effects on human neuronal cells," *Endocrinology*, 154(1):375-387, Epub Dec. 13, 2012.

(56) References Cited

OTHER PUBLICATIONS

Pollio et al., "Increased expression of the oligopeptidase THOP1 is a neuroprotective response to Abeta toxicity," *Neurobiol Dis.*, 31(1):145-158, Epub Apr. 29, 2008.

Robertson et al., "The frequency of KRAS and BRAF mutations in intrahepatic cholangiocarcinomas and their correlation with clinical outcome," *Hum Pathol.*, 44(12):2768-2773, Epub Oct. 15, 2013.

Rolyan et al., "Amyloid-β protein modulates the perivascular clearance of neuronal apolipoprotein E in mouse models of Alzheimer's disease," *J Neural Transm.*, 118(5):699-712, Epub Jan. 6, 2011.

Ruprich et al., "Probabilistic modelling of exposure doses and implications for health risk characterization: glycoalkaloids from potatoes," *Food Chem Toxicol.*, 47(12):2899-2905, Epub Mar. 13, 2009.

Sagare et al., "Low-density lipoprotein receptor-related protein 1: a physiological Aβ homeostatic mechanism with multiple therapeutic opportunities," *Pharmacol Ther.*, 136(1):94-105, Epub Jul. 20, 2012.

Schiepers et al., "APOE E4 status predicts age-related cognitive decline in the ninth decade: longitudinal follow-up of the Lothian Birth Cohort 1921," *Mol Psychiatry*, 17(3):315-324, Epub Jan. 25, 2011.

Shibue et al., "An integrin-linked machinery of cytoskeletal regulation that enables experimental tumor initiation and metastatic colonization," *Cancer Cell.*, 24(4):481-498, Epub Sep. 12, 2013.

Singh et al., "Protective effect of potato peel powder in ameliorating oxidative stress in streptozotocin diabetic rats," *Plant Foods Hum Nutr.*, 60(2):49-54, Jun. 2005.

Stentz and Kitabchi, "Transcriptome and proteome expression in activated human CD4 and CD8 T-lymphocytes," *Biochem Biophys Res Commun.*, 324(2):692-696, Nov. 12, 2004.

Stöhr and Federici, "Insulin resistance and atherosclerosis: convergence between metabolic pathways and inflammatory nodes," *Biochem J.*, 454(1):1-11, Aug. 15, 2013.

Stöhr et al., "Insulin receptor signaling mediates APP processing and β-amyloid accumulation without altering survival in a transgenic mouse model of Alzheimer's disease," *Age (Dordr).*, 35(1):83-101, Epub Nov. 6, 2011.

Sugden and Holness, "Therapeutic potential of the mammalian pyruvate dehydrogenase kinases in the prevention of hyperglycaemia," *Curr Drug Targets Immune Endocr Metabol Disord.*, 2(2):151-165, Jul. 2002.

Talaei et al., "Increased protein aggregation in Zucker diabetic fatty rat brain: identification of key mechanistic targets and the therapeutic application of hydrogen sulfide," *BMC Cell Biol.*, 15:1, 17 pages, Jan. 6, 2014.

Tan et al., "Regulation of mammalian pyruvate dehydrogenase alpha subunit gene expression by glucose in HepG2 cells," *Biochem J.*, 336 ( Pt 1):49-56, Nov. 15, 1998.

UniProtKB/Swiss-Prot: O00213.2 (GI No. 12229629) "RecName: Full=Amyloid beta A4 precursor protein-binding family B member 1; AltName: Full=Protein Fe65," Mar. 19, 2014, 12 pages.

Watt et al., "Bioenergetic cost of making an adenosine triphosphate molecule in animal mitochondria," *Proc Natl Acad Sci U S A.*, 107(39):16823-16827, Epub Sep. 16, 2010.

Welters et al., "NF-kappaB, nitric oxide and opiate signaling," *Med Hypotheses.*, 54(2):263-268, Feb. 2000.

Yamatoya et al., "Hypolipidemic effects of hydrolyzed xyloglucan," *Macromolecular Symposia*, 120(1): 231-236, Jul. 1997.

Zanchi et al., "Renal expression of FGF23 in progressive renal disease of diabetes and the effect of ACE inhibitor," *PLoS One.*, 8(8):e70775, Aug. 14, 2013.

Zhu et al., "Cholinergic regulation of morphine release from human white blood cells: evidence for a novel nicotinic receptor via pharmacological and microarray analysis," *Int J Immunopathol Pharmacol.*, 20(2):229-237, Apr.-Jun. 2007.

Zywicki et al., "Comparison of rapid liquid chromatography-electrospray ionization-tandem mass spectrometry methods for determination of glycoalkaloids in transgenic field-grown potatoes," *Anal. Biochem.*, 336(2):178-186, Jan. 15, 2005.

International Search Report and Written Opinion for PCT/US2014/053443, dated Dec. 18, 2014, 14 pages.

Japanese Office Action in Application No. JP2016-544345, dated Jul. 5, 2018, 6 pages (with English Translation).

Kumar et al., "Dietary roles of non-starch polysachharides in human nutrition: A Review," *Crit Rev. Food Sci Nutr.*, 52(10/11):899-935, 2012.

Ohtani and Misaki., "An in vitro study of the effects of cell wall polysaccharides of potatoes on digestibilities of their starched," *Journal of the Japan Society of Nutrition and Food Science.*, 38(5):363-370, 1985.

Ohtani., "Structure of non-starchy polysaccharides of potatoes (*Solanum tuberosum*) having different cooking properties (Part 1)," *Journal of Home Economics of Japan.*, 40(7):593-601, 1989.

Ohtani., "Structure of non-starchy polysaccharides of potatoes (*Solanum tuberosum*) having different cooking properties (Part 2)," *Journal of Home Economics of Japan.*, 42(4):313-320, 1991.

Ohtani., "Structure of non-starchy polysaccharides of potatoes (*Solanum tuberosum*) having different cooking properties (Part 3)," *Journal of Home Economics of Japan.*, 42(4):321-325, 1991.

Proceedings of the 60th commemoration meeting of the Japanese Society for Food Science and Technology, Aug. 29, 2013, 124 (reference showing well-known technique).

European Search Report for Application. No. 14846523.2 dated Feb. 17, 2017, 12 pages.

Ludvik et al., "Node of action of ipomoea batatas (caiapo) in type 2 diabetic patients," Metabolism XX US., 52(7):875-880, Jul. 1, 2003.

McClelland et al., "Bio-medical effect of Sweet Potato in People with Diabetes," J Am Dietetic Association., 107(8): A104, Jul. 24, 2007.

Oki et al., "The effects of an arabinogalactan-protein from the white-skinned sweet potato (*Ipomoea batatas* L.) on blood glucose in spontaneous diabetic mice," Biosci Biotechnol Biochem., 75(3):596-598, Epub Mar. 7, 2011.

Fry, "The Structure and Functions of Xyloglucan," Journal of Experimental Botany, 1989, 40(210):1-11.

Li et al., "Effect of the Lycium barbarum polysaccharides on age-related oxidative stress in aged mice," Journal of Ethnopharmacology, 2007, 111(28):504-511.

Li et al., "Lycium Barbarum Polysaccharides Reduce Neuronal Damage, Blood-Retinal Barrier Disruption and Oxidative Stress in Retinal Ischemia/Reperfusion Injury," PLoS ONE, 2011, 6(1):e16380, 14 pages.

Smith, J.G., Organic Chemistry, 3rd ed, McGaw Hill, 2009, p. 241.

Weksler et al., "The immune system, amyloid-b peptide, and Alzheimer's disease," Immunological Reviews, 2005, 205:244-256.

International Search Report and Written Opinion for PCT/US2016/024283, dated Jun. 30, 2016, 10 pages.

International Search Report and Written Opinion for PCT/US2016/024295, dated Jun. 27, 2016, 11 pages.

International Preliminary Report on Patentability for PCT/US2014/053443, dated Mar. 31, 2016, 10 pages.

European Office Action in European Application No. 13769274.5, dated Jun. 25, 2019, 12 pages.

Galactomannan, Wikipedia, [retrieved from internet on Apr. 29, 2019]<URL: https://en.wikipedia.org/wiki/Galactomannan> published on Apr. 26, 2013 as per Wayback Machine.

Jancik et al., "Clinical Relevance of KRAS in Human Cancers," J. Bionnedi. and Biotech., 2010:13, 2010.

Jarvis et al., "The polysaccharide structure of potato cell walls: chemical fractionation," Planta, 152(2):93-100, Jun. 1981.

Alikhani et al., "Mitochondria and Alzheimer's disease: amyloid-beta peptide uptake and degradation by the presequence protease, hPreP," J. Bioenerg. Bionnennbr., 41(5):447-451, 2009.

Ludvik et al, "Mode of action of ipomoea batatas (Caiapo) in type 2 diabetic patients," Metabolism, Jul. 2003, 52(7):875-80.

Nelson et al., "Neurologic effects of exogenous saccharides: a review of controlled human, animal, and in vitro studies," Nutr. Neurosci., 15(4):149-62, Jul. 2012.

Vincken et al, "Potato xyloglucan is built from XXGG-type subunits," Carbohydrate Research, Jul. 19, 1996, 288:219-232.

Yaoi., J Applied Glycoscience., 2(3):185-190, 2012.

(56) References Cited

OTHER PUBLICATIONS

Zykwinska et al., "Evidence for in vitro binding of pectin side chains to cellulose1," Plant Physiology., 139:397-407, Sep. 2005.

Ikeda, "Metabolic Turn Over of Amyloid Fibrils and Post-Treatment Regression of Amyloid Deposits in Systemic Amyloidosis With Polyneuropathy," Rinsho Shinkeigaku, 51(11):1143-5, Nov. 2011, (English abstract at the end of document).

Olmstead et al., "A summary of molecular systematic research in Solanaceae: 1982-2006," InVI International Solanaceae Conference: Genomics Meets Biodiversity 745, (pp. 255-268), Jul. 2006.

Sekijima et al., "Epidemiological and clinical aspects of non-hereditary systemic amyloidosis," Rinsho shinkeigaku=Clinical neurology, 51(11):1130-3, Nov. 2011, (English abstract at the end of document).

Takuma, "Mitochondrial Dysfunction and Apoptosis in Neurodegenerative Diseases," The Japanese Pharmocological Society, 127(5):349-54, May 2006 (Partial English translation).

Xiaoli et al., "Effect of polysaccharide in purple sweet potato on the antitumor activity of cancer bearing mice," Journal of Southwest China Normal University, 30(2):333-336, 2005 (English Abstract).

Zhao et al., "[Anti-tumor Activity of Components Isolated From Purple Sweet Potato Polysaccharides]," Zhejiang Da Xue Xue Bao Yi Xue Ban., 40(4):365-373, Jul. 2011 (English Abstract).

\* cited by examiner

Head to Tail MF=771 RMF=829

(mainlib) 1,2,3,4,5-Penta-O-acetyl-D-xylitol (Text File) Scan 5126 (33.206 min): NeuroDeriv2ndS1.D\data.ms Head to Tail MF=881 RMF=901

(mainlib) Galactitol, hexaacetate (Text File) Scan 5340 (34.483 min): NeuroDeriv2ndS1.D\data.ms Head to Tail MF=847 RMF=868

(replib) Myo-inositol, hexaacetate

METHODS AND MATERIALS FOR TREATING DIABETES OR LIVER STEATOSIS

BACKGROUND

1. Technical Field

This document relates to methods and materials for treating diabetes and/or liver steatosis. For example, this document relates to using compositions containing a potato polysaccharide preparation to reduce one or more symptoms of diabetes or liver steatosis. In some cases, this document relates to using compositions containing a potato polysaccharide preparation to reduce triglyceride levels, to reduce serum glucose levels, to reduce water consumption, to reduce urine production, to reduce kidney weight, to reduce liver weight, and/or to increase abdominal fat.

2. Background Information

Potatoes are starchy, edible tubers obtained from potato plants and form an integral part of much of the world's food supply. In fact, potatoes are the fourth largest food crop in the world. The main potato species worldwide is *Solanum tuberosum*.

SUMMARY

This document provides methods and materials for treating diabetes and/or liver steatosis. For example, this document provides methods for using compositions containing a potato polysaccharide preparation to reduce one or more symptoms of diabetes or liver steatosis. In some cases, a composition containing a potato polysaccharide preparation provided herein can be used to reduce triglyceride levels, to reduce serum glucose levels, to reduce water consumption, to reduce urine production, to reduce kidney weight, to reduce liver weight, and/or to increase abdominal fat. In some cases, a composition containing a potato polysaccharide preparation provided herein can be used to treat fatty liver disease.

Having the ability to use a composition containing a potato polysaccharide preparation described herein to reduce one or more symptoms of diabetes or liver steatosis can provide clinicians and patients with an effective treatment regime for these conditions.

This document also provides compositions (e.g., nutritional supplement compositions) that contain a potato polysaccharide preparation. For example, this document provides nutritional supplement compositions containing a potato polysaccharide preparation, methods for obtaining potato polysaccharide preparations, methods for making nutritional supplement compositions containing a potato polysaccharide preparation, and methods for increasing or decreasing expression of polypeptides involved with mitochondria activity or function.

In some cases, the compositions provided herein (e.g., nutritional supplement compositions and potato polysaccharide preparations provided herein) can be used to increase or decrease expression of polypeptides involved with mitochondria activity or function. For example, a composition containing a potato polysaccharide preparation provided herein or a potato polysaccharide preparation provided herein can be used to increase expression of a transcription factor A, mitochondrial polypeptide (a TFAM polypeptide), an ATP synthase, H$^+$ transporting, mitochondrial F1 complex, alpha subunit 1 polypeptide (an ATP5A1 polypeptide), a pyruvate dehydrogenase (lipoamide) alpha 1 polypeptide (a PDHA1 polypeptide), a pyruvate dehydrogenase (lipoamide) alpha 2 polypeptide (a PDHA2 polypeptide), a thimet oligopeptidase 1 polypeptide (a THOP1 polypeptide), or a combination thereof. In some cases, a composition containing a potato polysaccharide preparation provided herein or a potato polysaccharide preparation provided herein can be used to decrease expression of a forkhead box 01 polypeptide (a FOX01A polypeptide), a nuclear factor of kappa light polypeptide gene enhancer in B-cells 1 polypeptide (a NFKB1 polypeptide), a pyruvate dehydrogenase kinase, isozyme 2 polypeptide (a PDK2 polypeptide), a pyruvate dehydrogenase kinase, isozyme 4 polypeptide (a PDK4 polypeptide), a 3-hydroxy-3-methylglutaryl-CoA reductase polypeptide (a HMGCR polypeptide), or a combination thereof. In some case, a composition containing a potato polysaccharide preparation provided herein or a potato polysaccharide preparation provided herein can be used to increase one or more polypeptides (e.g., one or more of a TFAM polypeptide, an ATP5A1 polypeptide, a PDHA1 polypeptide, a PDHA2 polypeptide, or a THOP1 polypeptide) and decrease one or more polypeptides (e.g., one or more of a FOX01A polypeptide, a NFKB1 polypeptide, a PDK2 polypeptide, a PDK4 polypeptide, or a HMGCR polypeptide).

In some cases, a composition provided herein (e.g., a nutritional supplement composition or potato polysaccharide preparation provided herein) can be used to increase or decrease expression of polypeptides involved with diabetes or liver steatosis. For example, a composition provided herein (e.g., a nutritional supplement composition containing a potato polysaccharide preparation provided herein or a potato polysaccharide preparation provided herein) can be used to increase expression of a lipase, hormone-sensitive polypeptide (an LIPE polypeptide) in adipocytes, to increase expression of a phosphoenolpyruvate carboxykinase 2 (mitochondrial) polypeptide (a PCK2 polypeptide), to increase expression of a monoacylglycerol O-acyltransferase 1 polypeptide (an MOGAT1 polypeptide), to increase expression of a peroxisome proliferator-activated receptor gamma, coactivator 1 alpha polypeptide (a PPARGC1a polypeptide), to increase expression of a peroxisome proliferator-activated receptor gamma, coactivator 1 beta polypeptide (a PPARGC1b polypeptide), to increase expression of a superoxide dismutase 2, mitochondrial polypeptide (an SOD2 polypeptide), to increase expression of a nuclear receptor subfamily 4, group A, member 1 polypeptide (an NR4A1 polypeptide) in adipocytes, to increase expression of an acetyl-CoA acetyltransferase 2 polypeptide (an ACAT2 polypeptide), to increase expression of a 3-hydroxy-3-methylglutaryl-CoA reductase polypeptide (an HMGCR polypeptide) in muscle cells, or a combination thereof. In some cases, a composition provided herein (e.g., a nutritional supplement composition or potato polysaccharide preparation provided herein) can be used to decrease expression of a 1-acylglycerol-3-phosphate O-acyltransferase 1 polypeptide (an AGPAT1 polypeptide), to decrease expression of an oxidized low density lipoprotein (lectin-like) receptor 1 polypeptide (an OLR1 polypeptide), to decrease expression of a branched chain amino-acid transaminase 2, mitochondrial polypeptide (a BCAT2 polypeptide), to decrease expression of a nuclear factor of kappa light polypeptide gene enhancer in B-cells 1 polypeptide (an NFKB1 polypeptide), to decrease expression of a SH2B adaptor protein 1 polypeptide (an SH2B1 polypeptide), to decrease expression of a lipoprotein lipase polypeptide (an LPL polypeptide), to decrease expression of a 3-hydroxy-3-methylglutaryl-CoA reductase polypeptide (an HMGCR polypeptide) in adipocytes, to decrease expression of a lipase, hormone-sensitive polypeptide (an LIPE polypeptide) in muscle cells, to decrease expression of a nuclear receptor subfamily 4, group A, member 1 polypeptide (an NR4A1 polypeptide) in muscle cells, to decrease expression of a phosphatase and tensin homolog polypeptide (a PTEN polypeptide), to decrease expression of a caspase 8, apoptosis-related cysteine peptidase polypeptide (a CASP8 polypeptide), or a combination thereof.

In some cases, a composition provided herein (e.g., a nutritional supplement composition or potato polysaccharide preparation provided herein) can be used to increase one or more polypeptides (e.g., one or more of an LIPE polypeptide (in adipocytes), a PCK2 polypeptide, an MOGAT1 polypeptide, a PPARGC1a polypeptide, a PPARGC1b polypeptide, an SOD2 polypeptide, an NR4A1 polypeptide (in adipocytes), an ACAT2 polypeptide, or an HMGCR polypeptide (in muscle cells)) and decrease one or more polypeptides (e.g., one or more of an AGPAT1 polypeptide, an OLR1 polypeptide, a BCAT2 polypeptide, an NFKB1 polypeptide, an SH2B1 polypeptide, an LPL polypeptide, an HMGCR polypeptide (in adipocytes), an LIPE polypeptide (in muscle cells), an NR4A1 polypeptide (in muscle cells), a PTEN polypeptide, or a CASP8 polypeptide).

In general, one aspect of this document features a method for treating diabetes. The method comprises, or consists essentially of, (a) identifying a mammal with diabetes, and (b) administering to the mammal a composition comprising a potato polysaccharide preparation obtained from raw potatoes, wherein the severity of a symptom of the diabetes is reduced. The composition can comprise the potato polysaccharide preparation in an amount that results in between 0.05 mg and 50 mg of the potato polysaccharide component of the potato polysaccharide preparation being administered to the mammal per kg of body weight of the mammal. The composition can comprise between 1 mg and 100 mg of the potato polysaccharide preparation. The composition can comprise between 6 mg and 20 mg of the potato polysaccharide preparation. The composition can comprise between 1 mg and 100 mg of the potato polysaccharide component of the potato polysaccharide preparation. The composition can comprise between 6 mg and 20 mg of the potato polysaccharide component of the potato polysaccharide preparation. The composition can be in the form of a tablet. The composition can comprise alpha lipoic acid. The composition can comprise alpha tocopherol. The potato polysaccharide preparation can be in an amount that results in between 0.075 mg and 0.5 mg of the potato polysaccharide component of the potato polysaccharide preparation being administered to the mammal per kg of body weight of the mammal. At least about 80 percent of the potato polysaccharide preparation can be potato polysaccharide. At least about 90 percent of the potato polysaccharide preparation can be potato polysaccharide. At least about 95 percent of the potato polysaccharide preparation can be potato polysaccharide. The mammal can be a human.

In another aspect, this document features a method for treating a fatty liver disease. The method comprises, or consists essentially of, (a) identifying a mammal with a fatty liver disease, and (b) administering to the mammal a composition comprising a potato polysaccharide preparation obtained from raw potatoes, wherein the severity of a symptom of the fatty liver disease is reduced. The composition can comprise the potato polysaccharide preparation in an amount that results in between 0.05 mg and 50 mg of the potato polysaccharide component of the potato polysaccharide preparation being administered to the mammal per kg of body weight of the mammal. The composition can comprise between 1 mg and 100 mg of the potato polysaccharide preparation. The composition can comprise between 6 mg and 20 mg of the potato polysaccharide preparation. The composition can comprise between 1 mg and 100 mg of the potato polysaccharide component of the potato polysaccharide preparation. The composition can comprise between 6 mg and 20 mg of the potato polysaccharide component of the potato polysaccharide preparation. The composition can be in the form of a tablet. The composition can comprise alpha lipoic acid. The composition can comprise alpha tocopherol. The potato polysaccharide preparation can be in an amount that results in between 0.075 mg and 0.5 mg of the potato polysaccharide component of the potato polysaccharide preparation being administered to the mammal per kg of body weight of the mammal. At least about 80 percent of the potato polysaccharide preparation can be potato polysaccharide. At least about 90 percent of the potato polysaccharide preparation can be potato polysaccharide. At least about 95 percent of the potato polysaccharide preparation can be potato polysaccharide. The mammal can be a human.

Unless otherwise defined, all technical and scientific terms used herein have the same meaning as commonly understood by one of ordinary skill in the art to which this invention pertains. Although methods and materials similar or equivalent to those described herein can be used in the practice or testing of the present invention, suitable methods and materials are described below. All publications, patent applications, patents, and other references mentioned herein are incorporated by reference in their entirety. In case of conflict, the present specification, including definitions, will control. In addition, the materials, methods, and examples are illustrative only and not intended to be limiting.

Other features and advantages of the invention will be apparent from the following detailed description, and from the claims.

DETAILED DESCRIPTION

Figure 1:
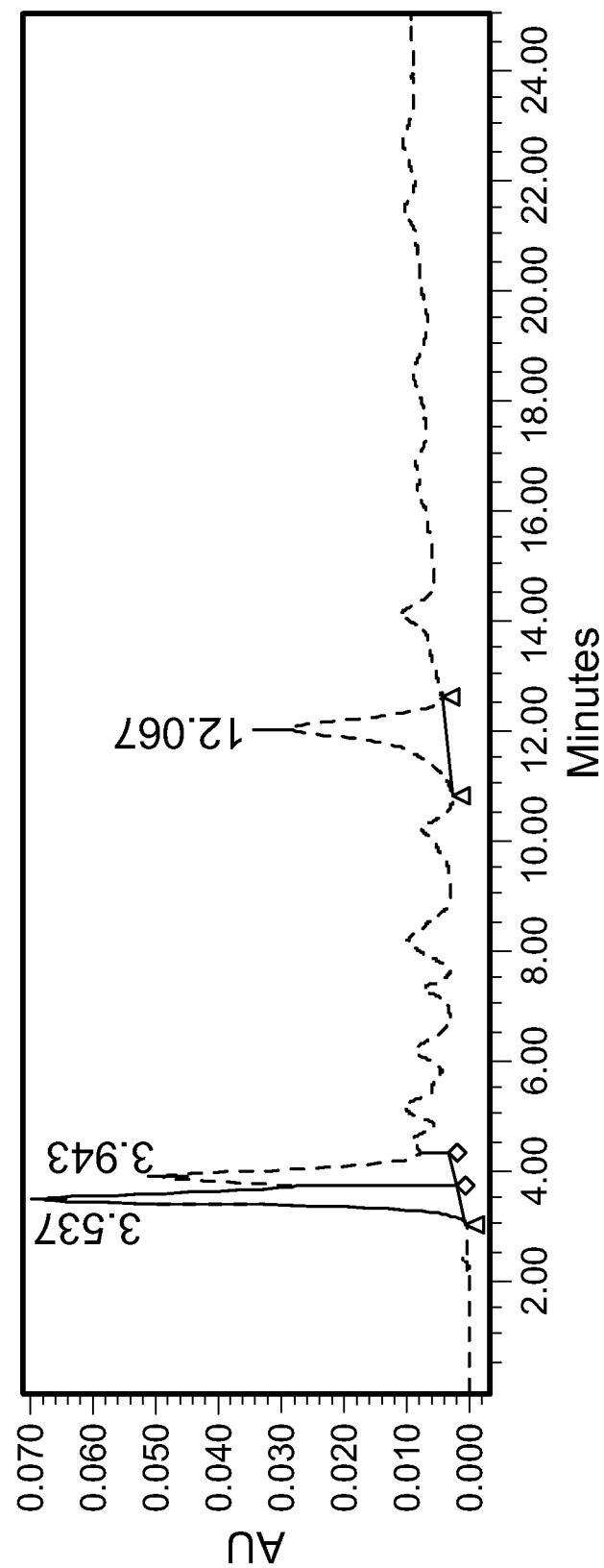
FIG. 1 is an HPLC chromatogram of a 10% ACN extract of raw potato (Russet Burbank).

This document provides methods and materials for treating diabetes and/or liver steatosis. For example, this document provides methods for using compositions containing a potato polysaccharide preparation to reduce one or more symptoms of diabetes or liver steatosis. In some cases, a composition containing a potato polysaccharide preparation provided herein can be used to reduce triglyceride levels, to reduce serum glucose levels, to reduce water consumption, to reduce urine production, to reduce kidney weight, to reduce liver weight, and/or to increase abdominal fat. In some cases, a composition containing a potato polysaccharide preparation provided herein can be used to treat fatty liver disease.

As described herein, a composition containing a potato polysaccharide preparation provided herein (e.g., a nutritional supplement composition provided herein) can be administered to any appropriate mammal to reduce one or more symptoms of diabetes, liver steatosis, and/or fatty liver disease. For example, a composition containing a potato polysaccharide preparation provided herein can be administered to a rat, mouse, dog, cat, horse, cow, goat, pig, chicken, duck, rabbit, sheep, monkey, or human to reduce one or more symptoms of diabetes and/or liver steatosis. Examples of diabetes symptoms include, without limitation, excessive fluid intake, frequent urination, elevated blood glucose, elevated urinary glucose, ketosis, and vascular degeneration. Examples of liver steatosis symptoms include, without limitation, hepatomegaly (enlarged liver), steatohepatitis, and malnutrition. Examples of fatty liver disease symptoms include, without limitation, cirrhosis, jaundice, and esophageal bleeding.

Any appropriate route of administration (e.g., oral or parenteral administration) can be used to administer a composition containing a potato polysaccharide preparation provided herein (e.g., a nutritional supplement composition provided herein) to a mammal. For example, a composition containing a potato polysaccharide preparation provided herein can be administered orally.

A composition provided herein (e.g., a nutritional supplement composition) can include one or more potato polysaccharide preparations. A potato polysaccharide preparation can be a preparation that is obtained from a water extract of potato and that contains polysaccharide material having the ability to be eluted from a C18 cartridge (e.g., a Sep-Pak Plus C-18 cartridge) with 10% acetonitrile. In some cases, a potato polysaccharide preparation can be a preparation that is obtained from potato and that contains polysaccharide material having HPLC characteristics of that of the peak eluted at 3.5 minutes as described in Example 1 (see, also, FIGS. 1, 2, and 28-34). In some cases, a polysaccharide of a potato polysaccharide preparation provided herein can be a polar, water-soluble polysaccharide. In some cases, a polysaccharide of a potato polysaccharide preparation provided herein can be a highly substituted complex xyloglucan material.

In some cases, a potato polysaccharide preparation can be a preparation that is obtained from potato and that contains polysaccharide material that, when derivatized, results in at least the following acylated carbohydrates as assessed using GC/MS: (a) myo-inositol (set to 1× to serve as an internal standard), (b) glucose at about 40× to about 60× the myo-inositol content (e.g., glucose at about 50× the myo-inositol content), (c) xylose at about 10× to about 20× the myo-inositol content (e.g., xylose at about 15× the myo-inositol content), (d) mannose at about 5× to about 15× the myo-inositol content (e.g., mannose at about 10× the myo-inositol content), and (e) galactose at about 3× to about 7× the myo-inositol content (e.g., galactose at about 5× the myo-inositol content). The derivatization procedure can include forming a dry residue of the polysaccharide material that is then hydrolyzed using trifluoroacetic acid. The resulting material is then reduced using sodium borohydride, and after borate removal, the end product is acylated using acetic anhydride and pyridine. The end products of the reaction are then injected directly on GC/MS to identify the acylated carbohydrates.

Figure 7:
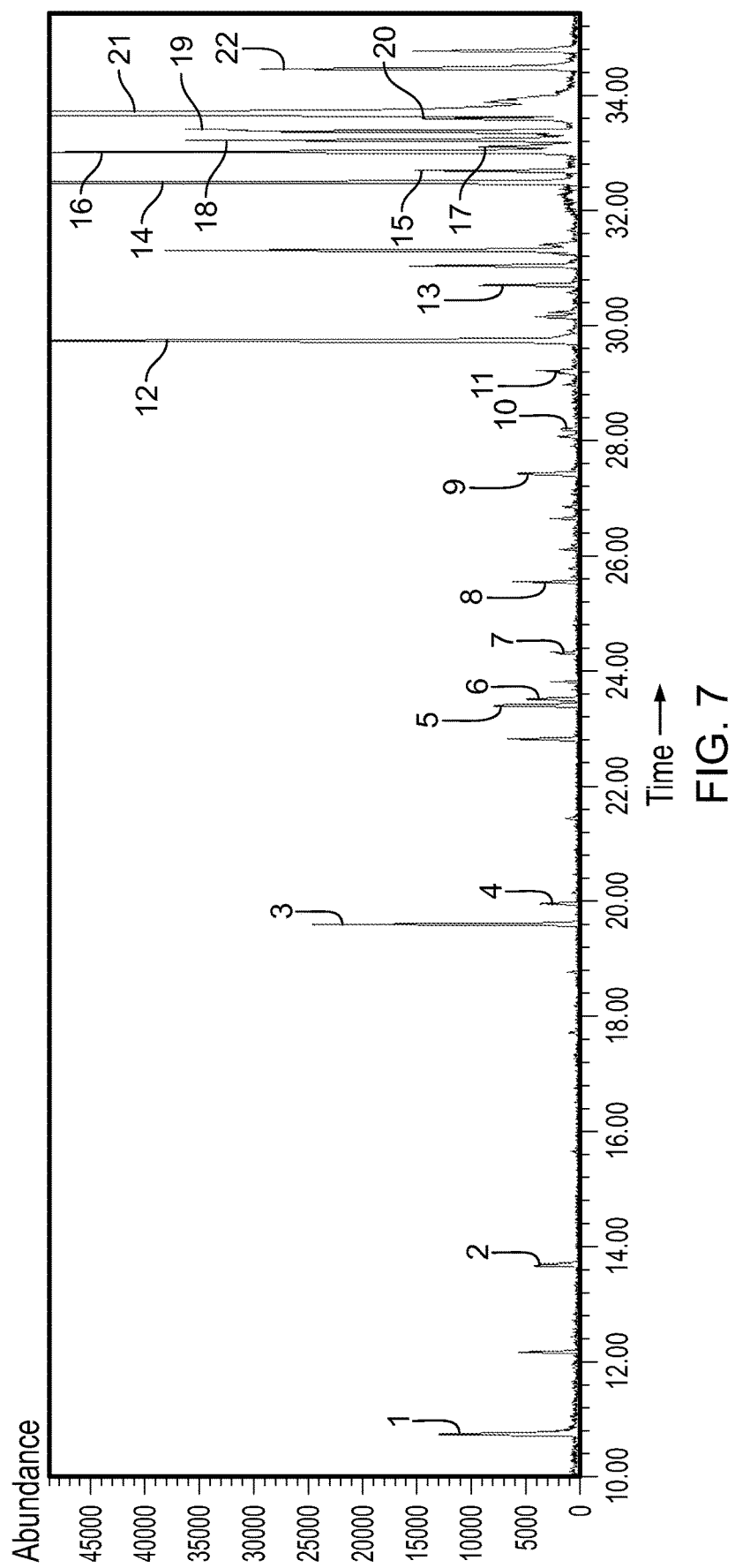
FIG. 7 is a total ion chromatogram of derivatized carbohydrate fragments of 3.5 minute HPLC peak material obtained from raw potato Russet Burbank).
Figure 8:
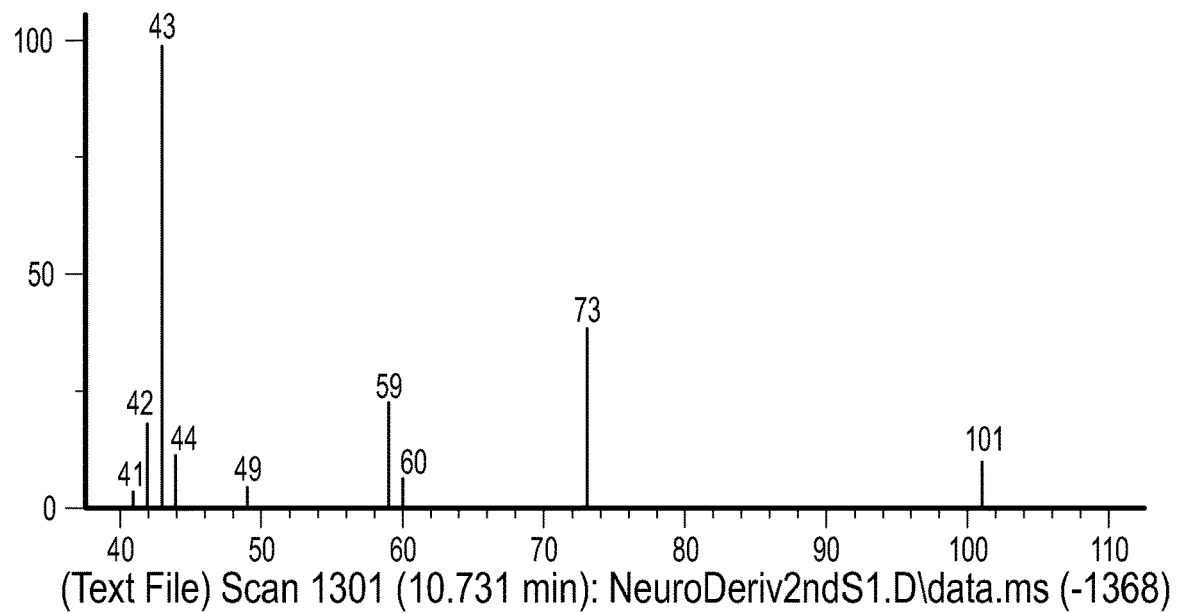
FIG. 8 is a fragmentation pattern of diacetamide. The peak fragmentation pattern is in the top panel, the compound library fragmentation match is in the bottom panel, and an overlay of the two is in the center panel.
Figure 8:
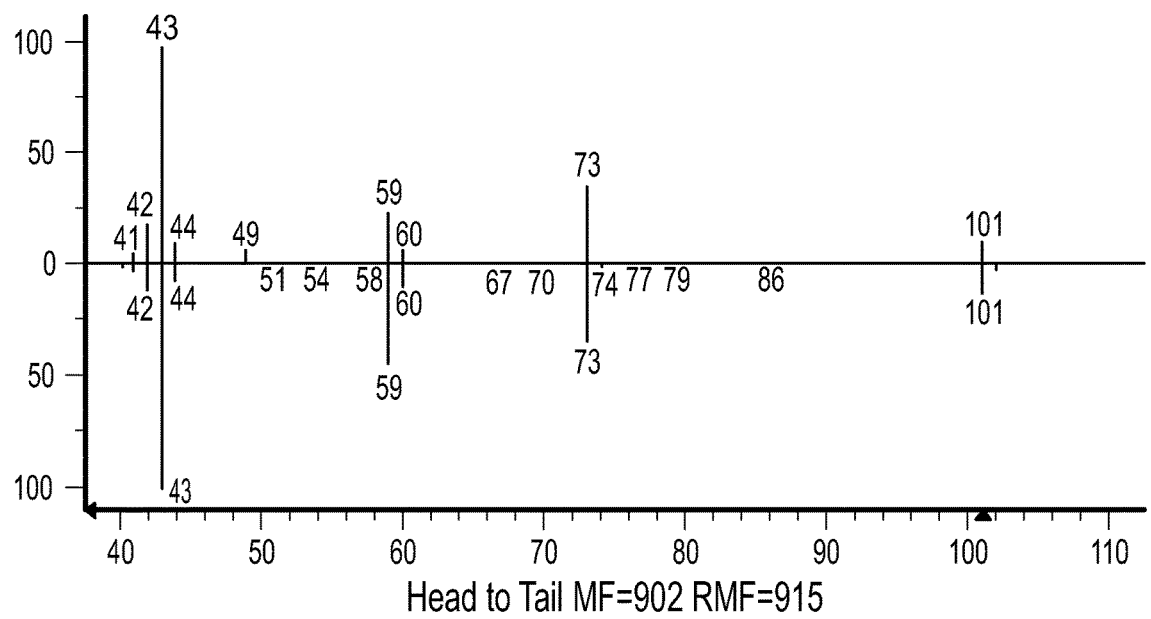
Figure 8:
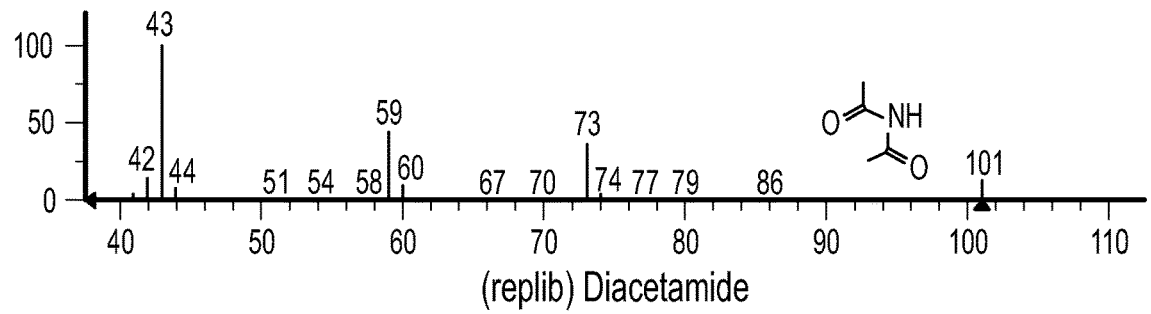
Figure 9:
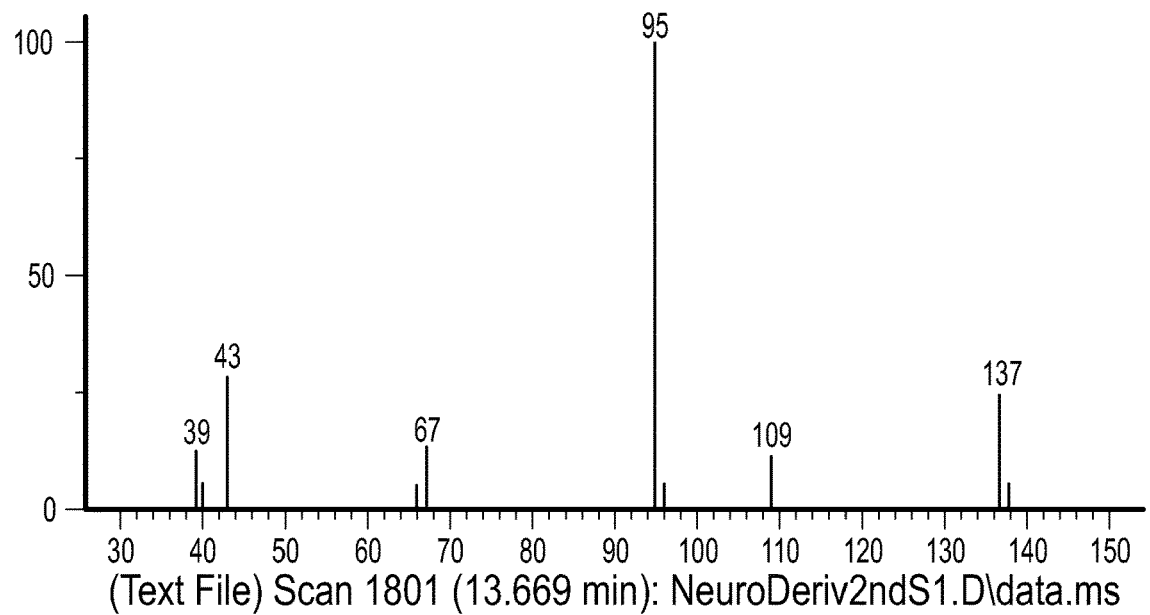
FIG. 9 is a fragmentation pattern of 3-acetoxy pyridine. The peak fragmentation pattern is in the top panel, the compound library fragmentation match is in the bottom panel, and an overlay of the two is in the center panel.
Figure 9:
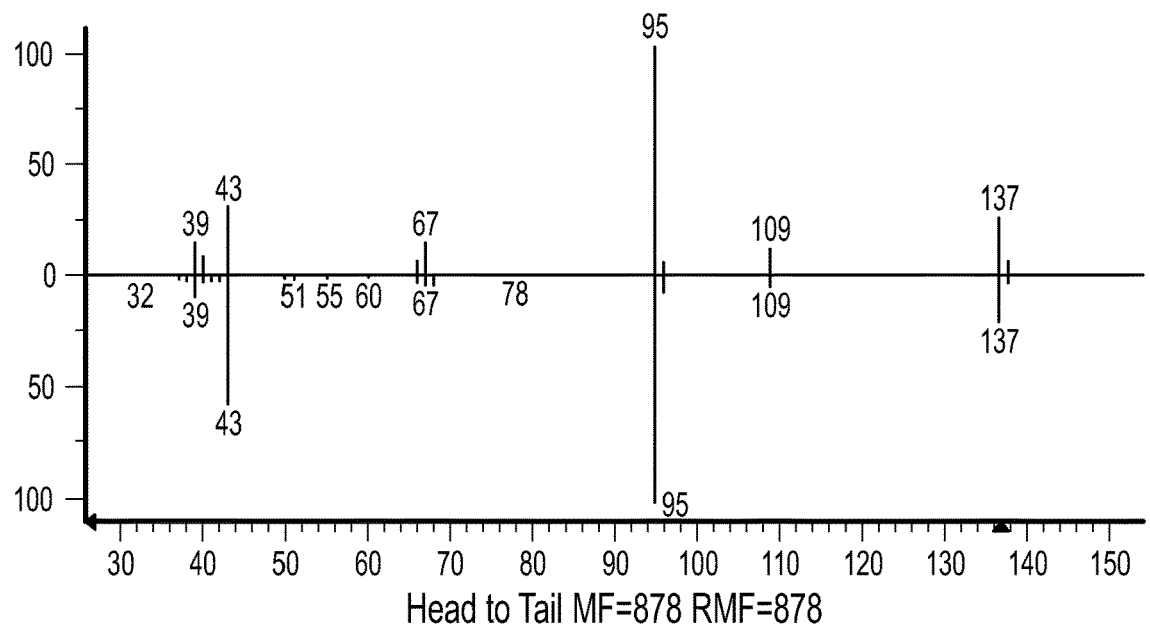
Figure 9:
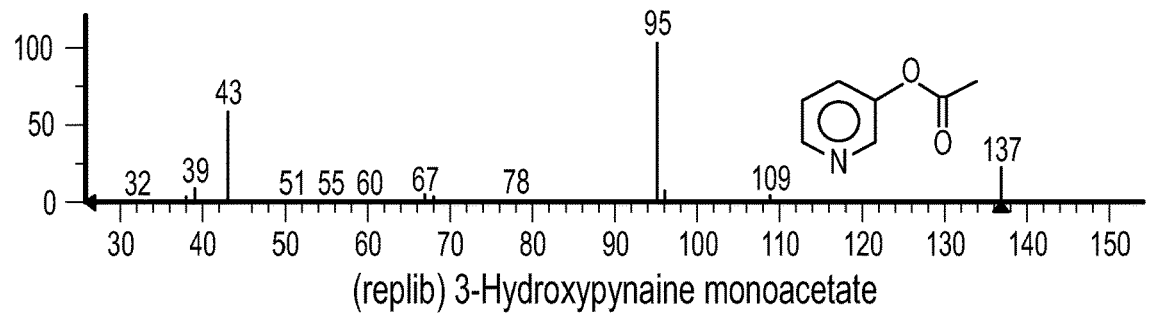
Figure 10:
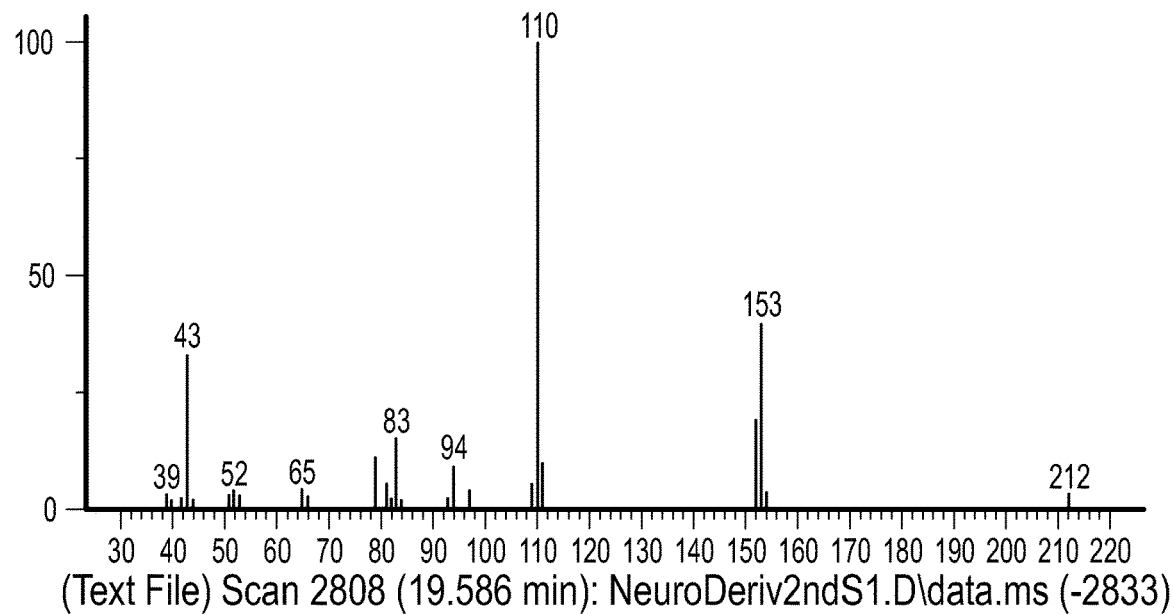
FIG. 10 is a fragmentation pattern of 3,4-furan dimethanol, diacetate. The peak fragmentation pattern is in the top panel, the compound library fragmentation match is in the bottom panel, and an overlay of the two is in the center panel.
Figure 10:
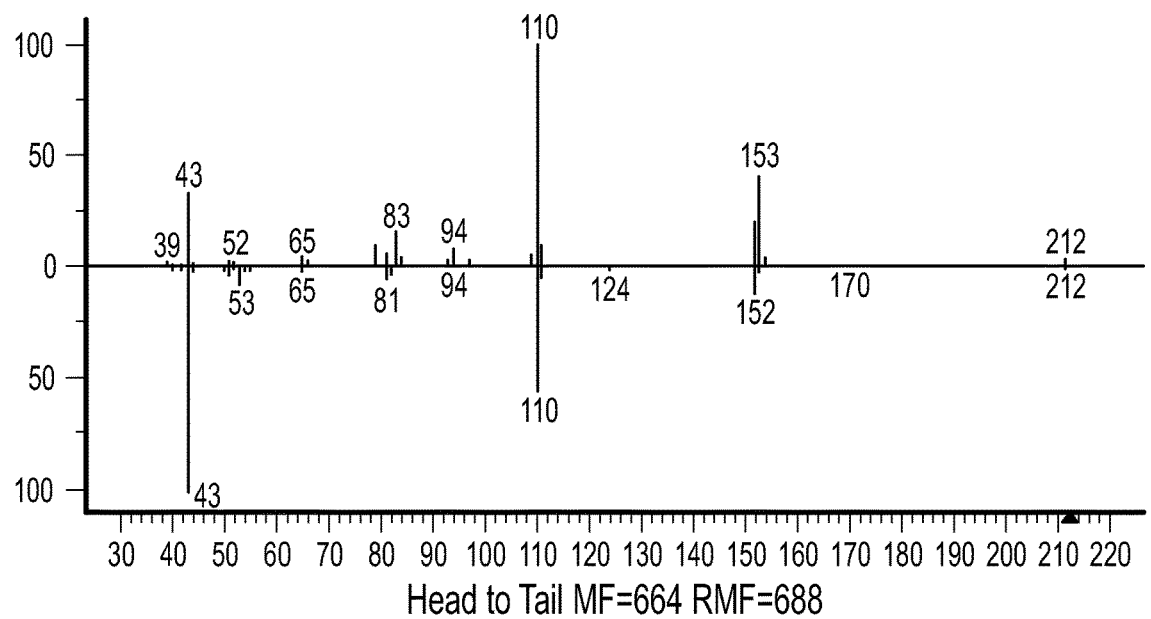
Figure 10:
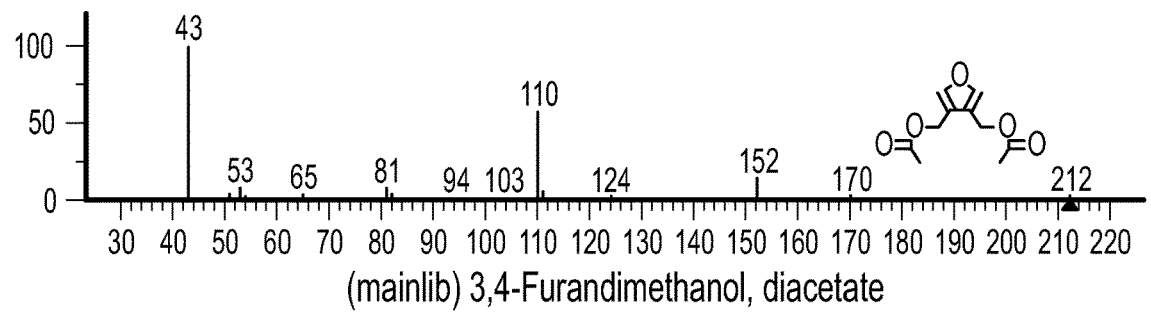
Figure 11:
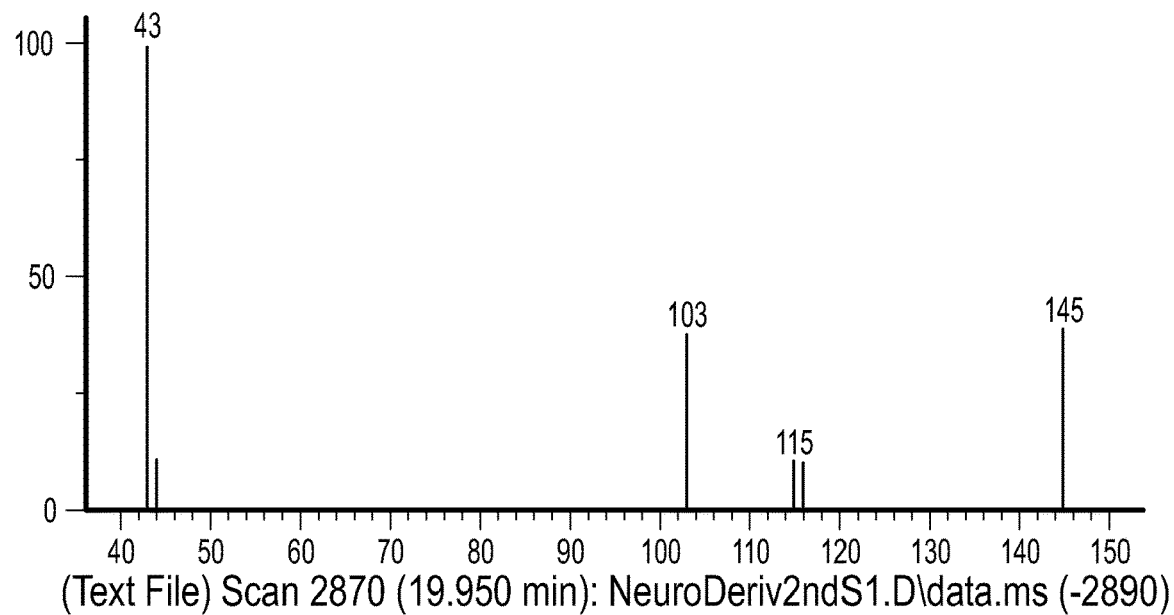
FIG. 11 is a fragmentation pattern of 1,2,3-propanetriol diacetate. The peak fragmentation pattern is in the top panel, the compound library fragmentation match is in the bottom panel, and an overlay of the two is in the center panel.
Figure 11:
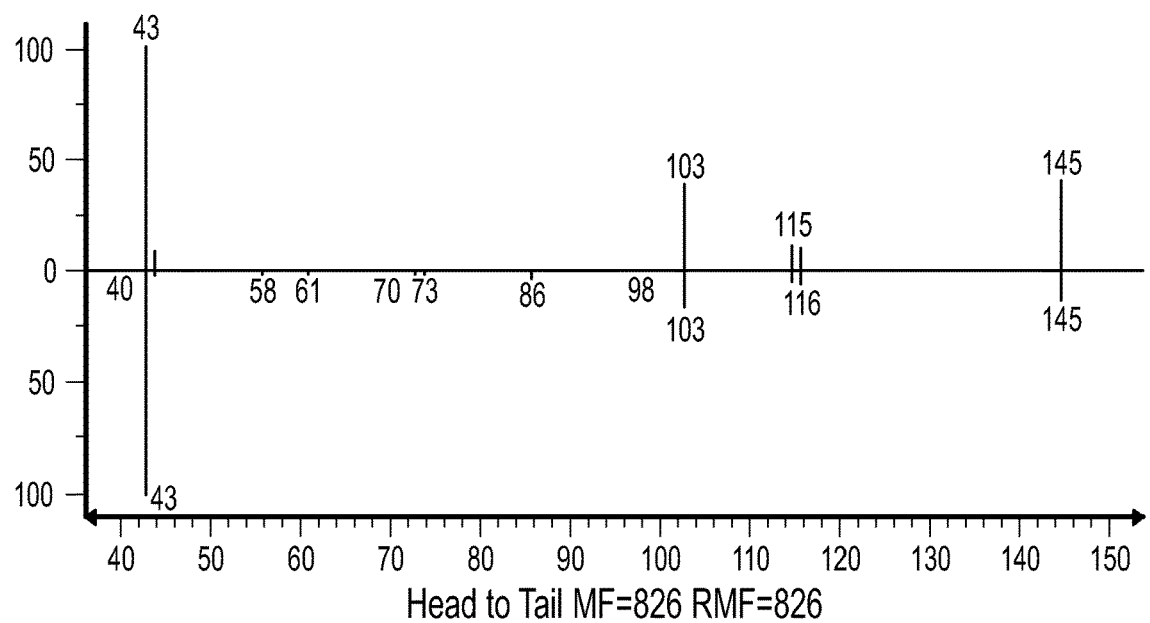
Figure 11:
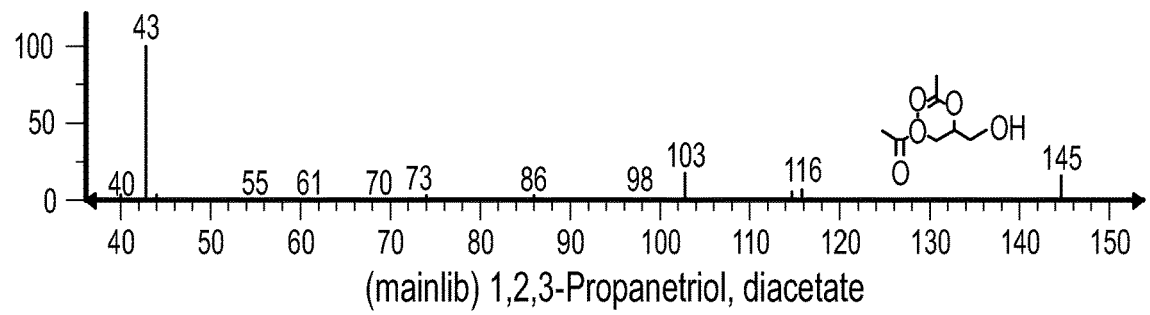
Figure 12:
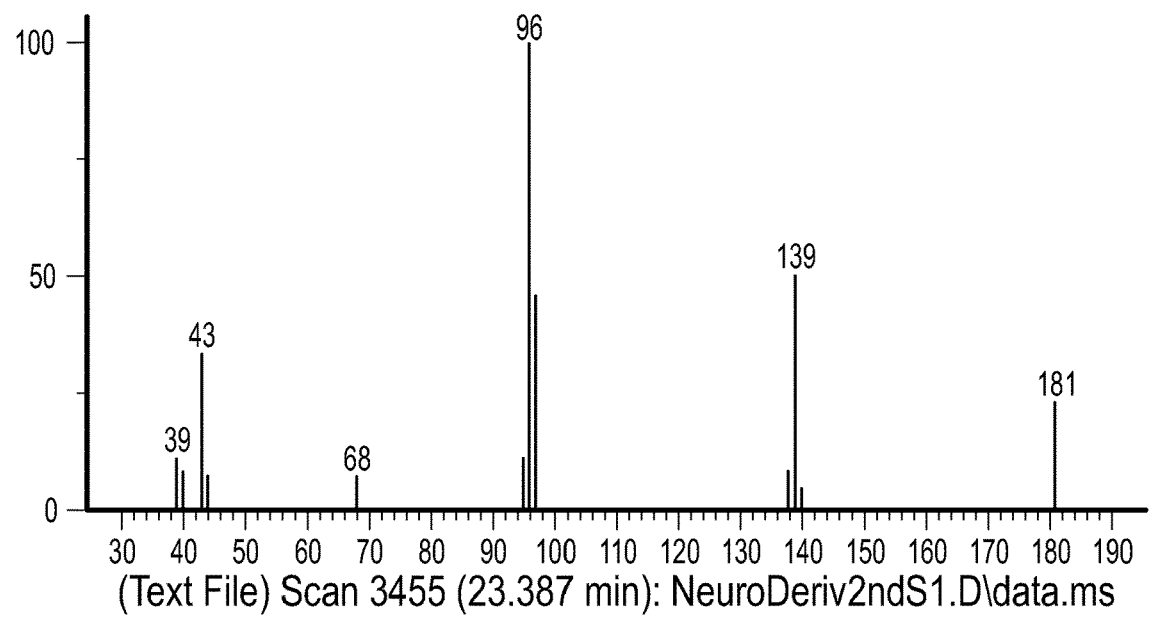
FIG. 12 is a fragmentation pattern of imidazole, 2-acetamino-5-methyl. The peak fragmentation pattern is in the top panel, the compound library fragmentation match is in the bottom panel, and an overlay of the two is in the center panel.
Figure 12:
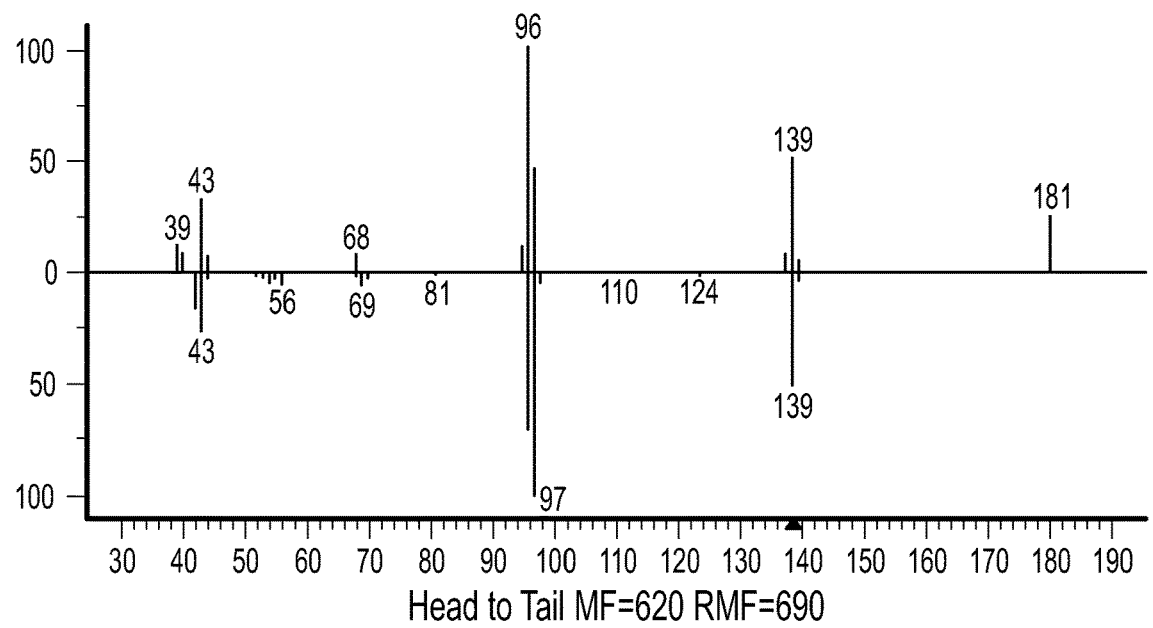
Figure 12:
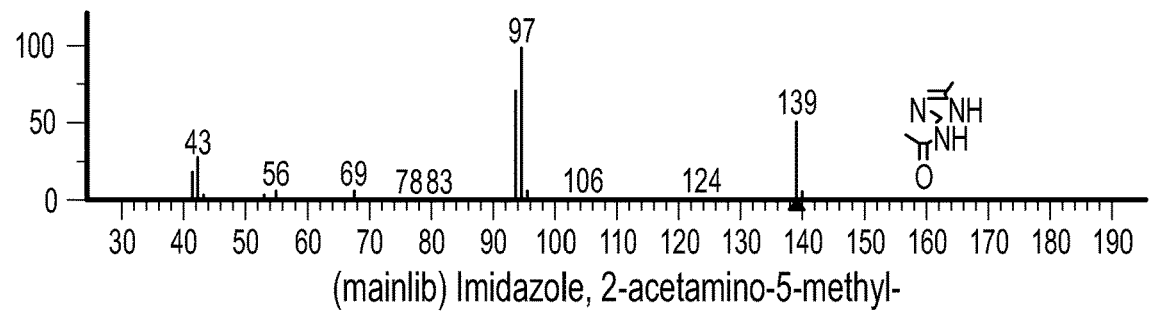
Figure 13:
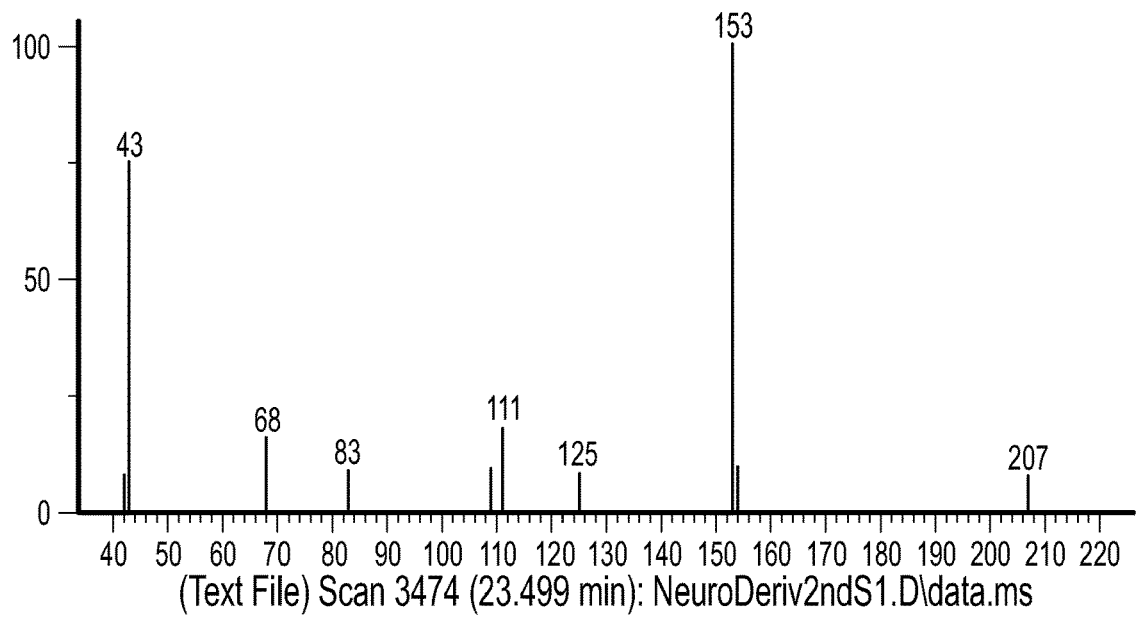
FIG. 13 is a fragmentation pattern of 6,7-dihydro-5H-pyrrol[2,1,c][1,2,4]triazole-3-carboxylic acid. The peak fragmentation pattern is in the top panel, the compound library fragmentation match is in the bottom panel, and an overlay of the two is in the center panel.
Figure 13:
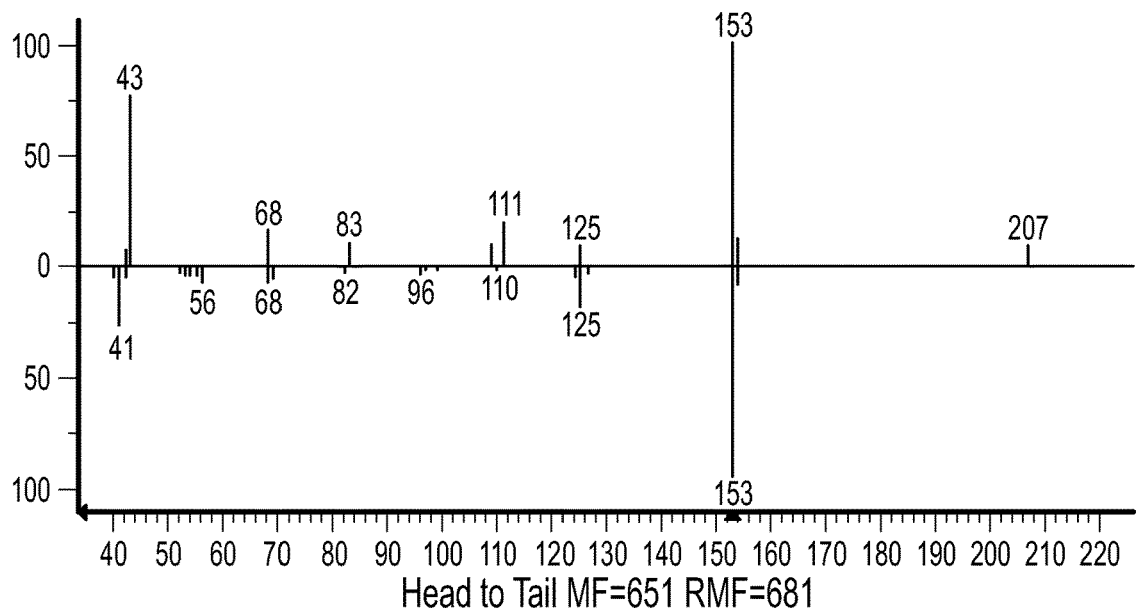
Figure 13:
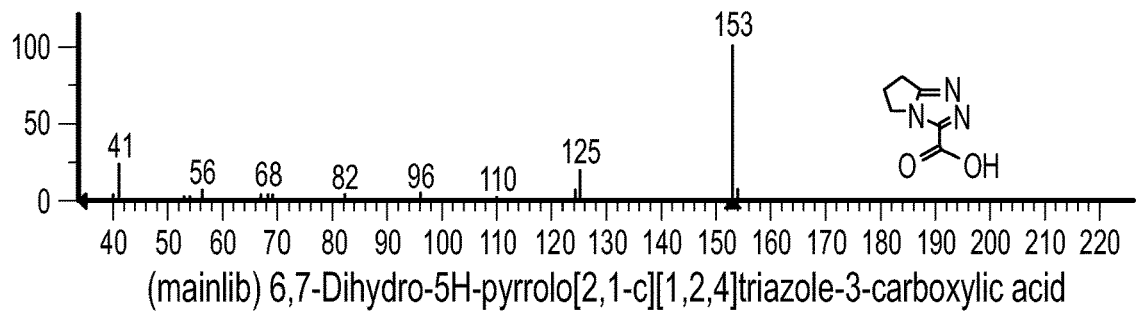
Figure 14:
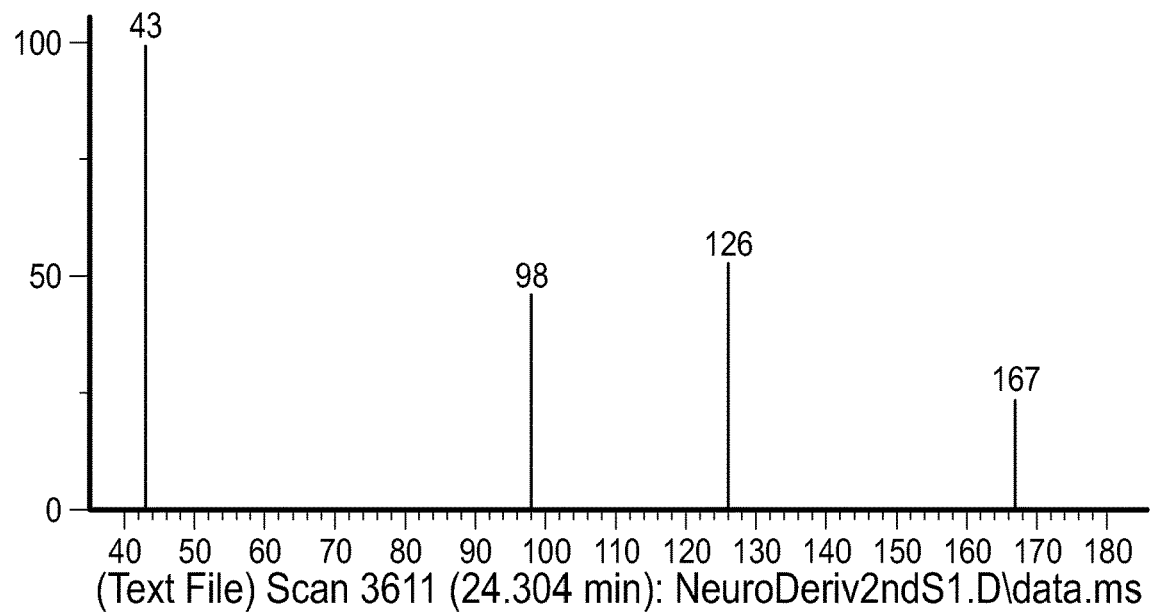
FIG. 14 is a fragmentation pattern of acetic acid, 1-(2-methyltetrazol-5-yl) ethenyl ester. The peak fragmentation pattern is in the top panel, the compound library fragmentation match is in the bottom panel, and an overlay of the two is in the center panel.
Figure 14:
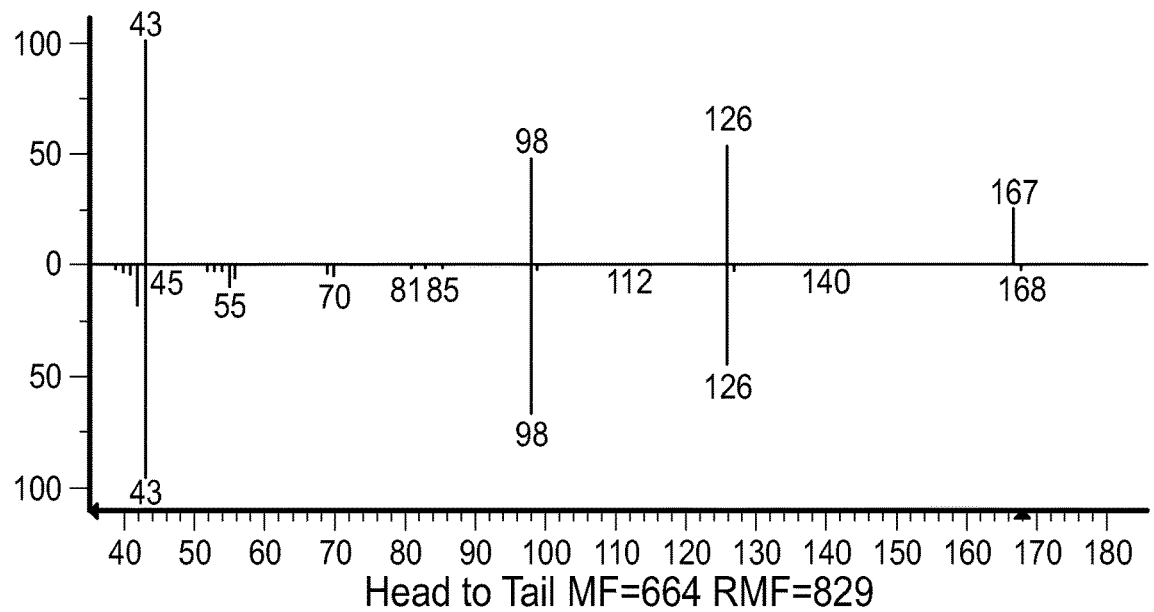
Figure 14:
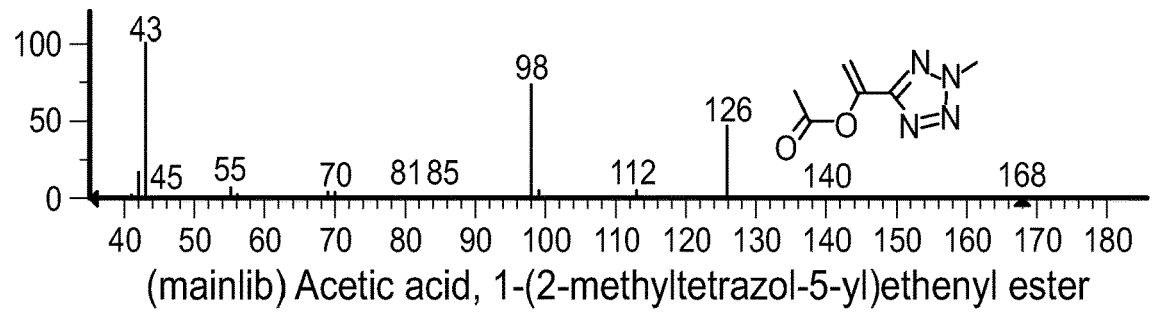
Figure 15:
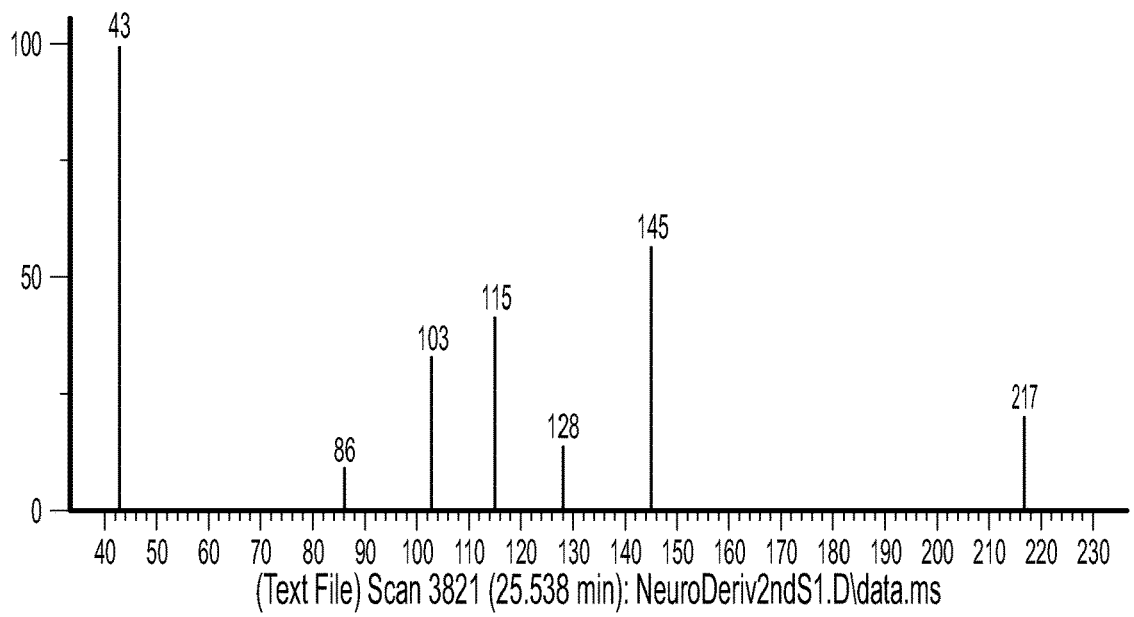
FIG. 15 is a fragmentation pattern of 1,2,3,4-butanetriol, tetraacetate (isomer 1). The peak fragmentation pattern is in the top panel, the compound library fragmentation match is in the bottom panel, and an overlay of the two is in the center panel.
Figure 15:
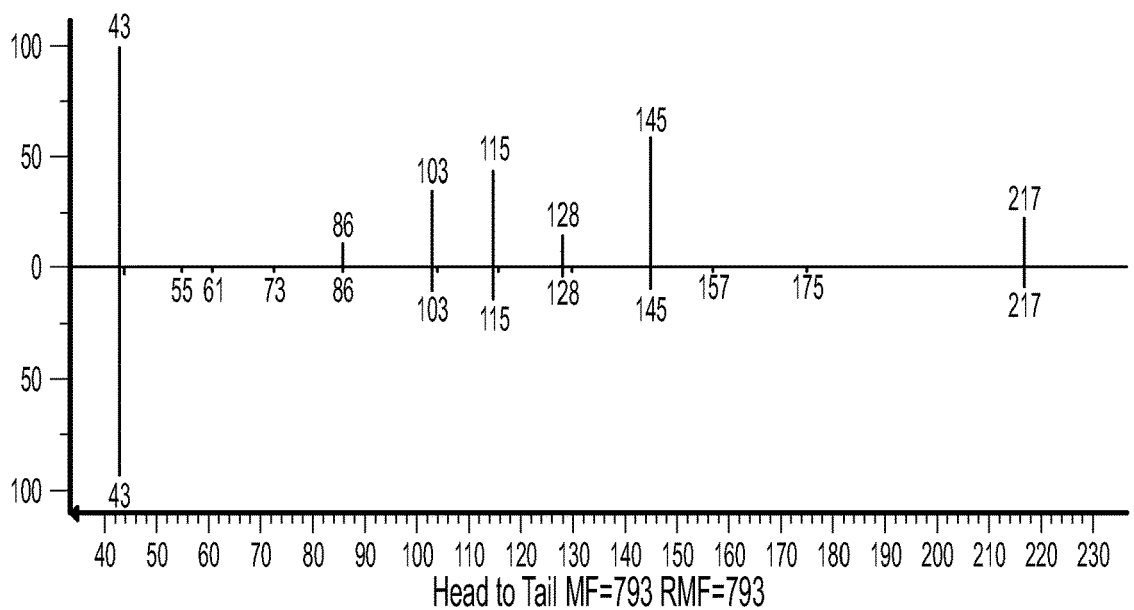
Figure 15:
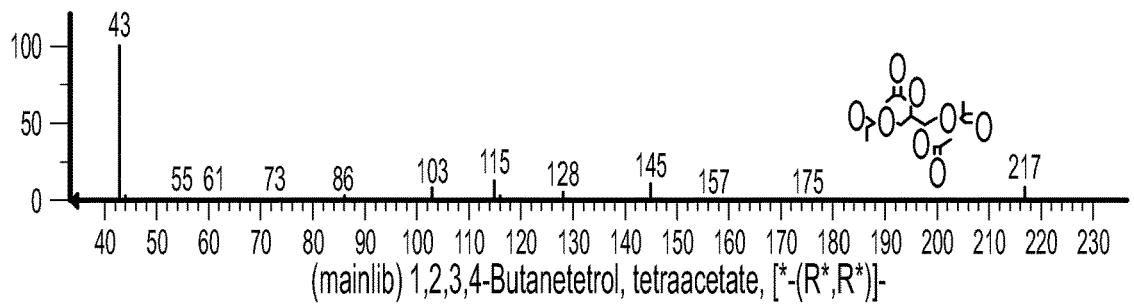
Figure 16:
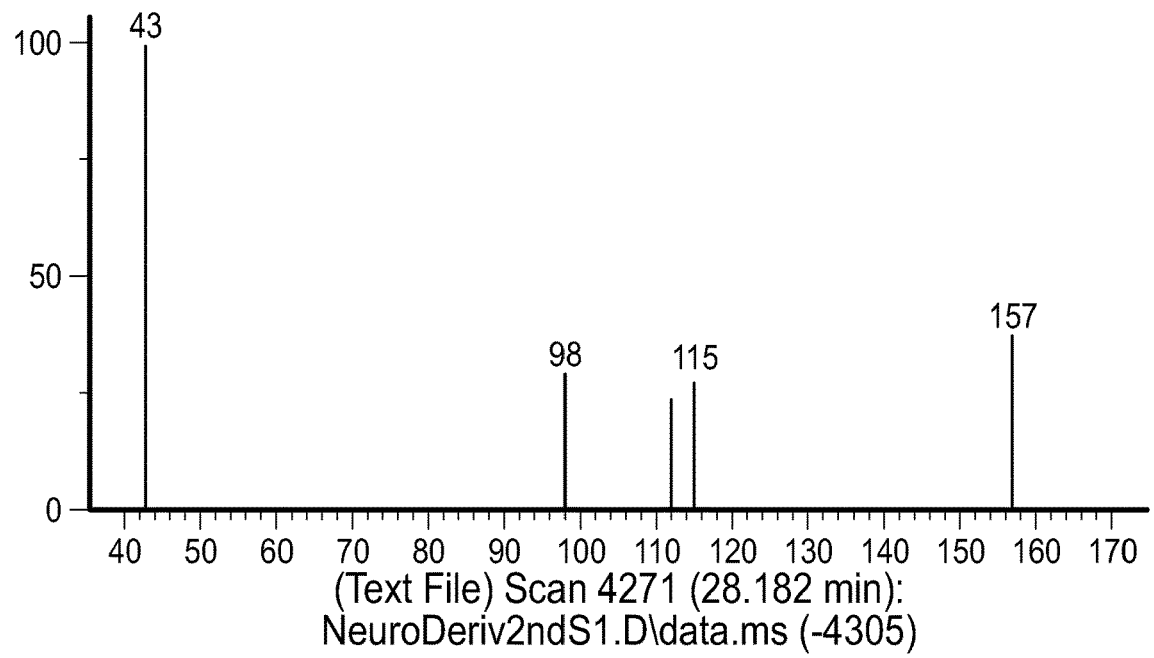
FIG. 16 is a fragmentation pattern of 1,2,3,4-butanetriol, tetraacetate (isomer 2). The peak fragmentation pattern is in the top panel, the compound library fragmentation match is in the bottom panel, and an overlay of the two is in the center panel.
Figure 16:
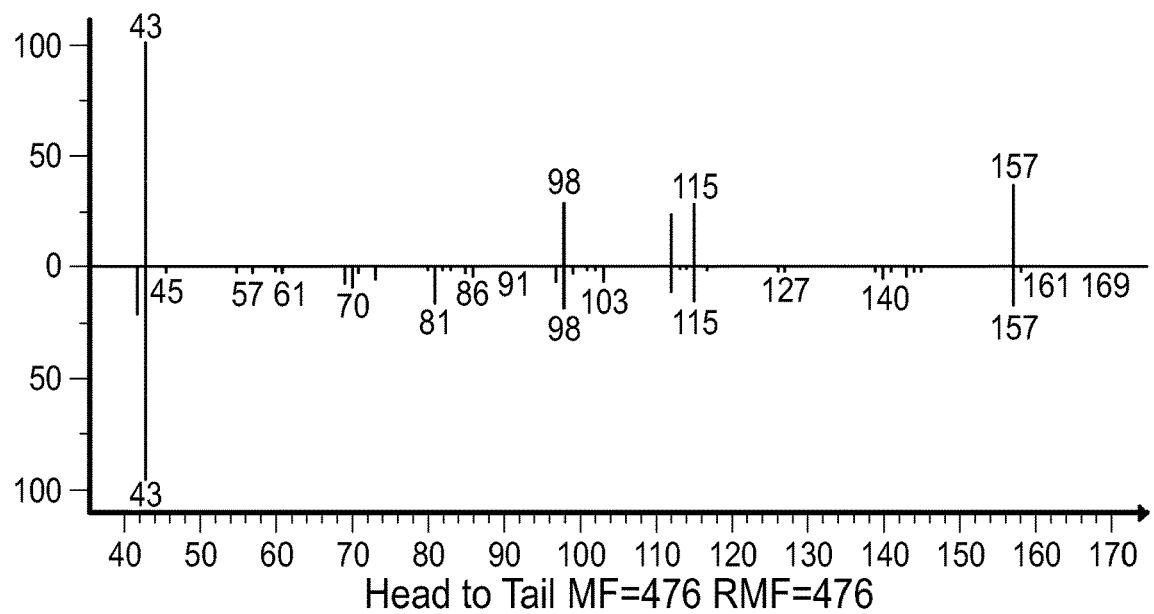
Figure 16:
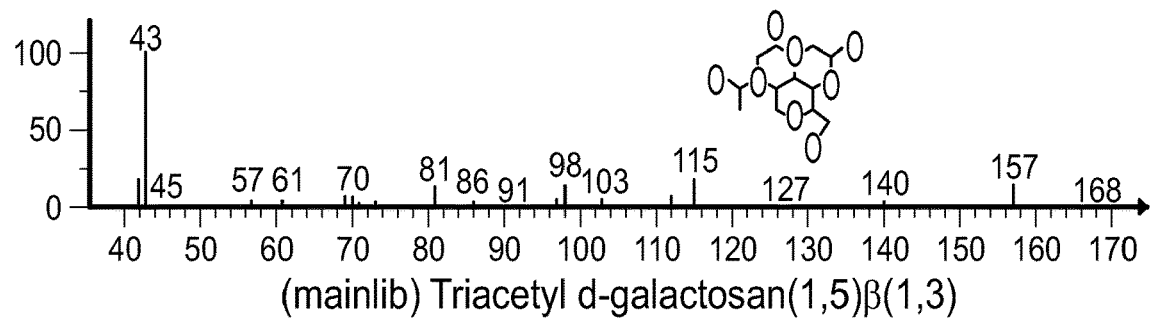
Figure 17:
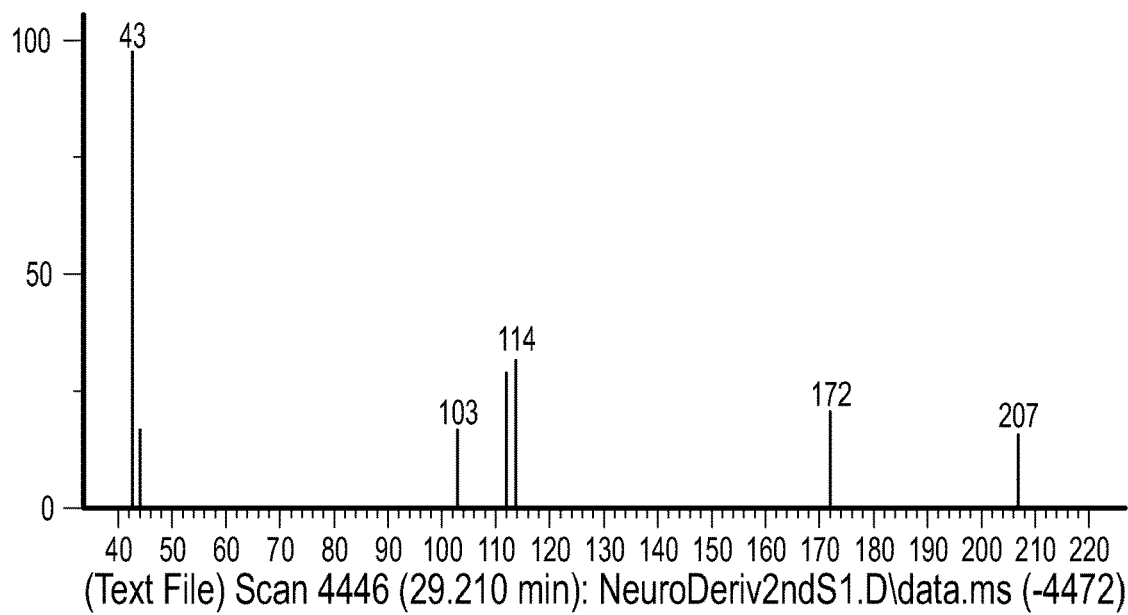
FIG. 17 is a fragmentation pattern of pentaerythritol tetraacetate. The peak fragmentation pattern is in the top panel, the compound library fragmentation match is in the bottom panel, and an overlay of the two is in the center panel.
Figure 17:
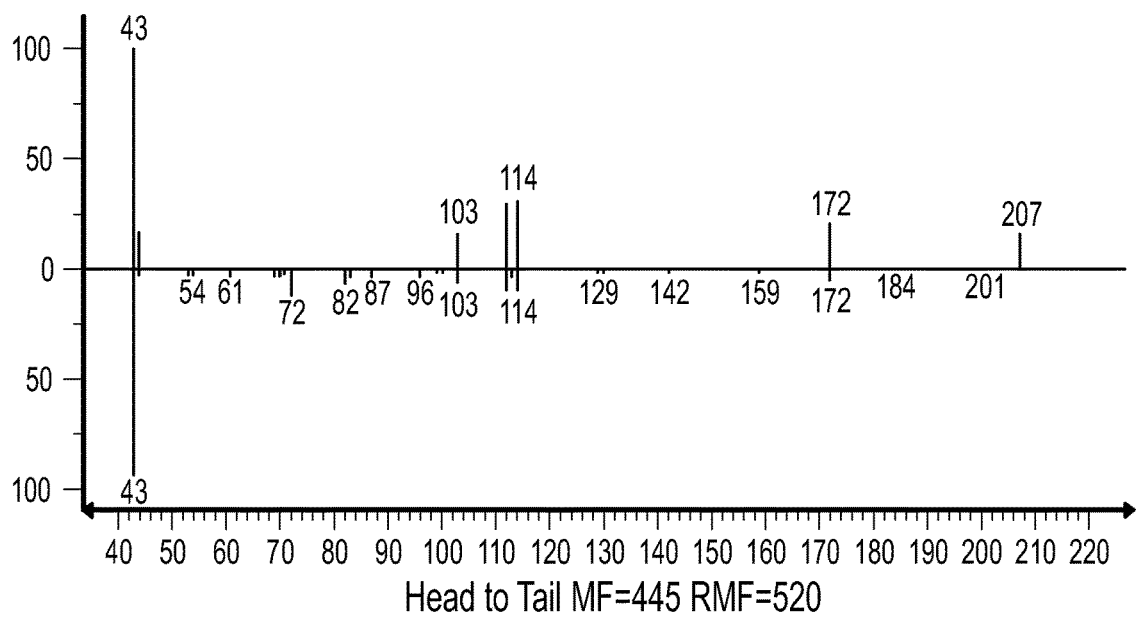
Figure 17:
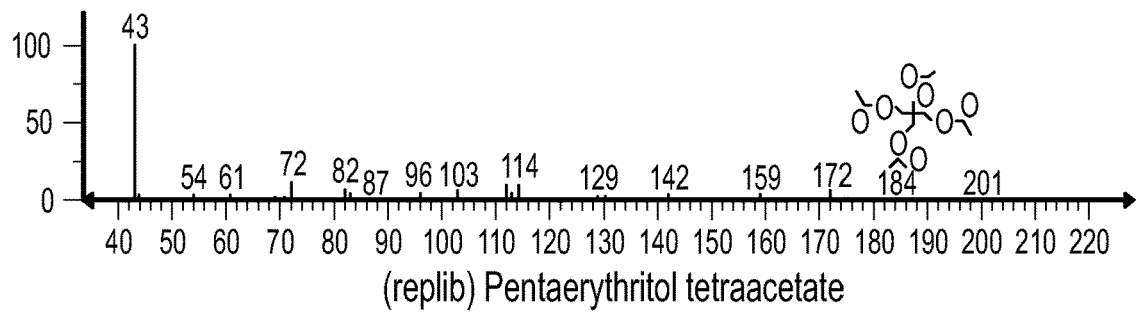
Figure 18:
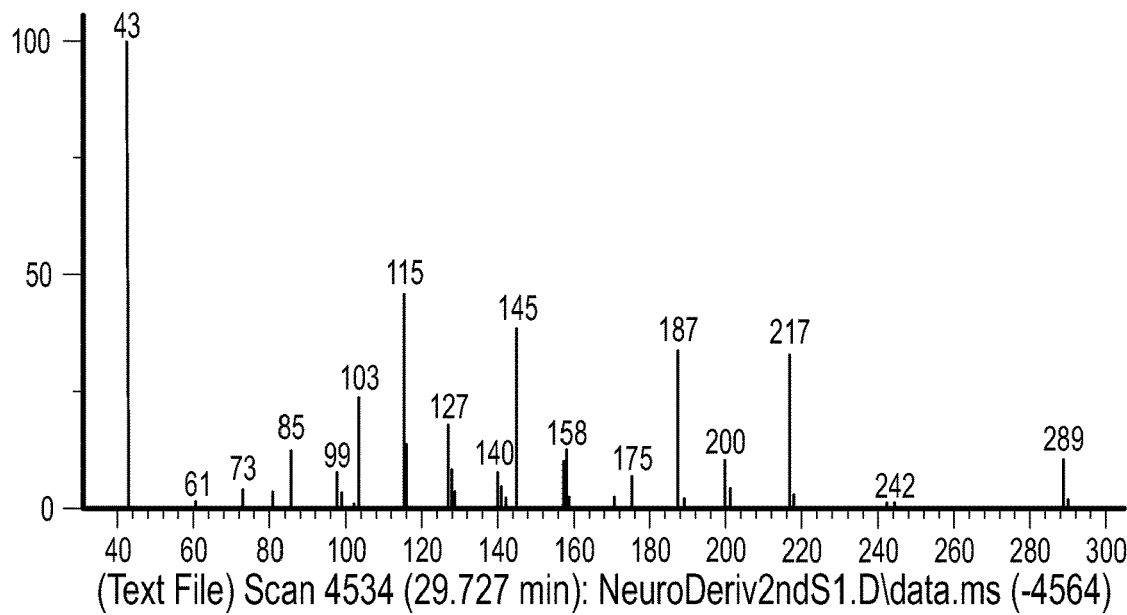
FIG. 18 is a fragmentation pattern of 1,2,3,4,5-penta-o-acetyl-D-xylitol (isomer 1). The peak fragmentation pattern is in the top panel, the compound library fragmentation match is in the bottom panel, and an overlay of the two is in the center panel.
Figure 18:
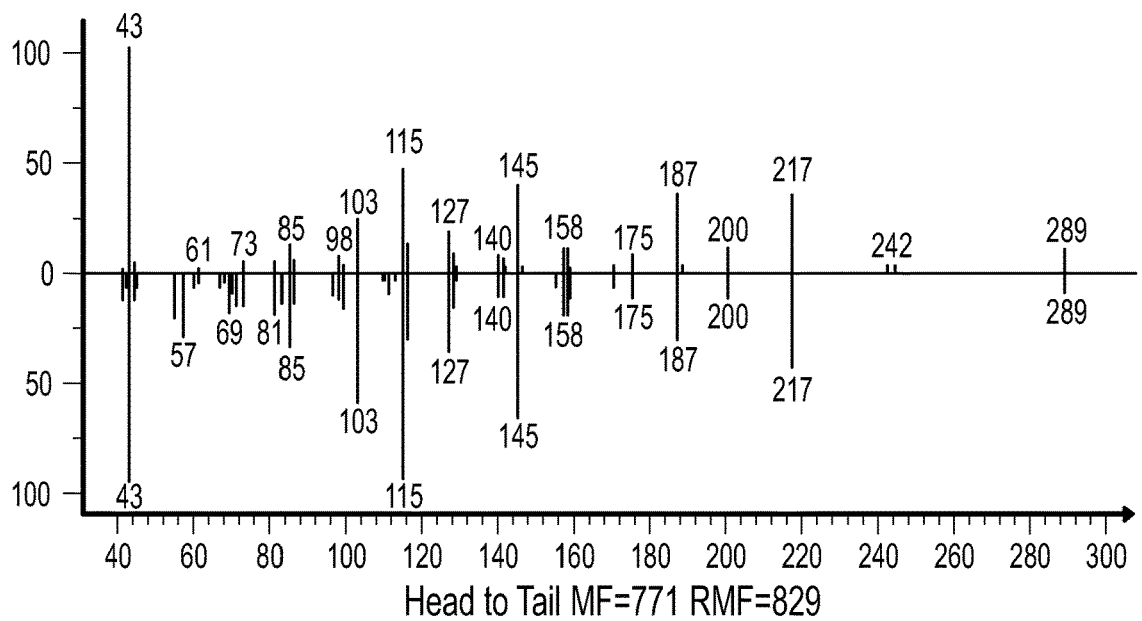
Figure 18:
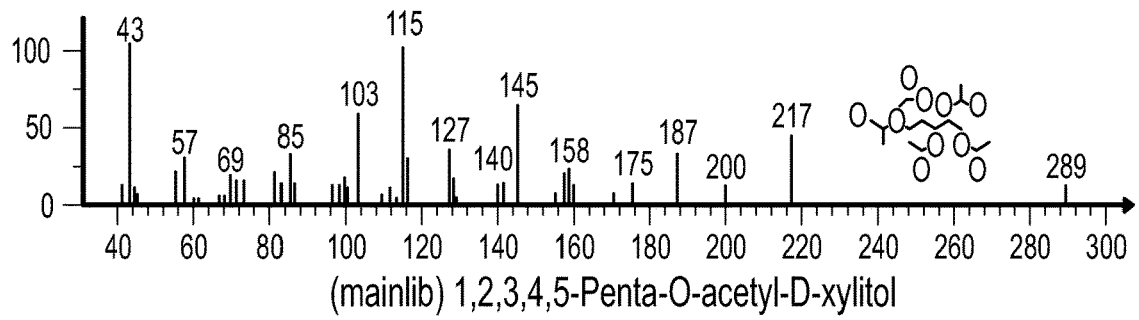
Figure 19:
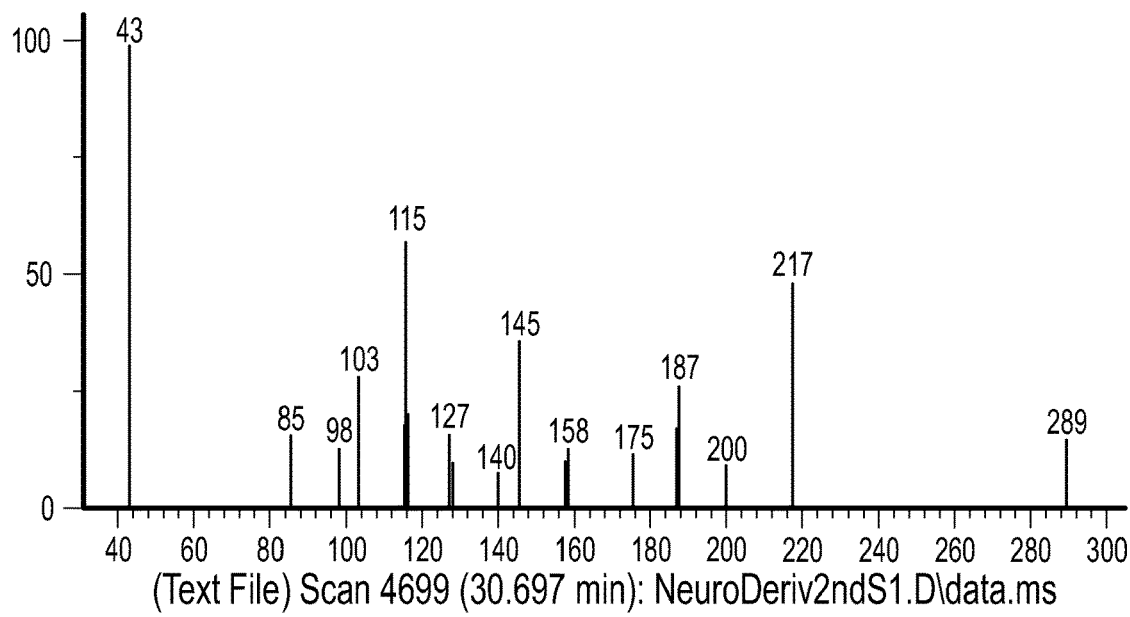
FIG. 19 is a fragmentation pattern of 1,2,3,4,5-penta-o-acetyl-D-xylitol (isomer 2). The peak fragmentation pattern is in the top panel, the compound library fragmentation match is in the bottom panel, and an overlay of the two is in the center panel.
Figure 19:
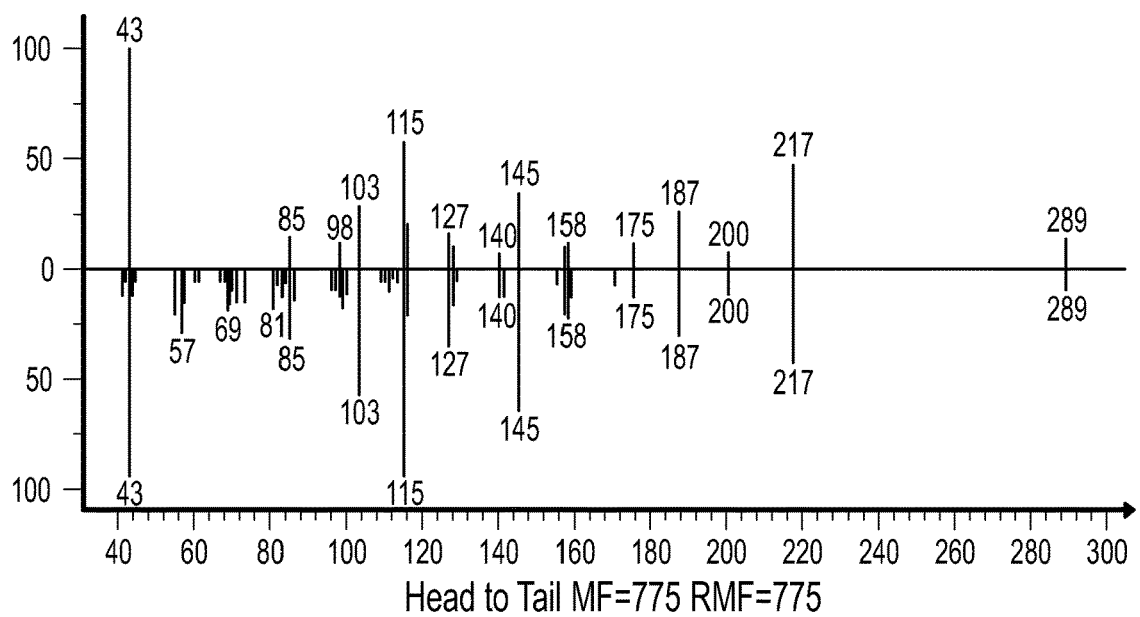
Figure 19:
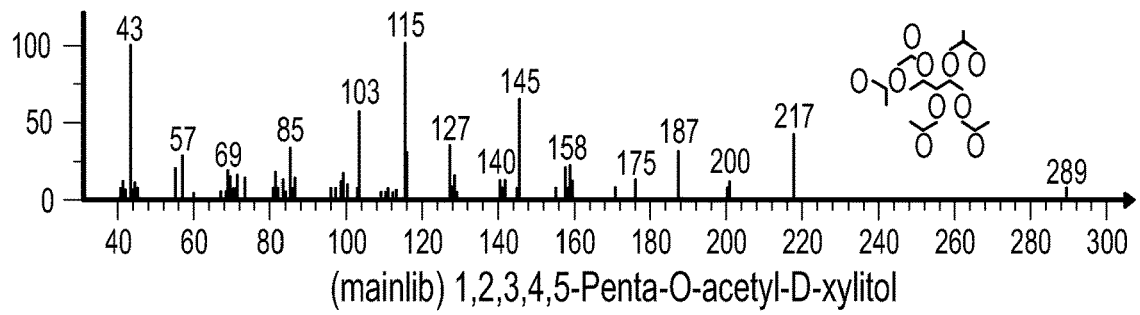
Figure 20:
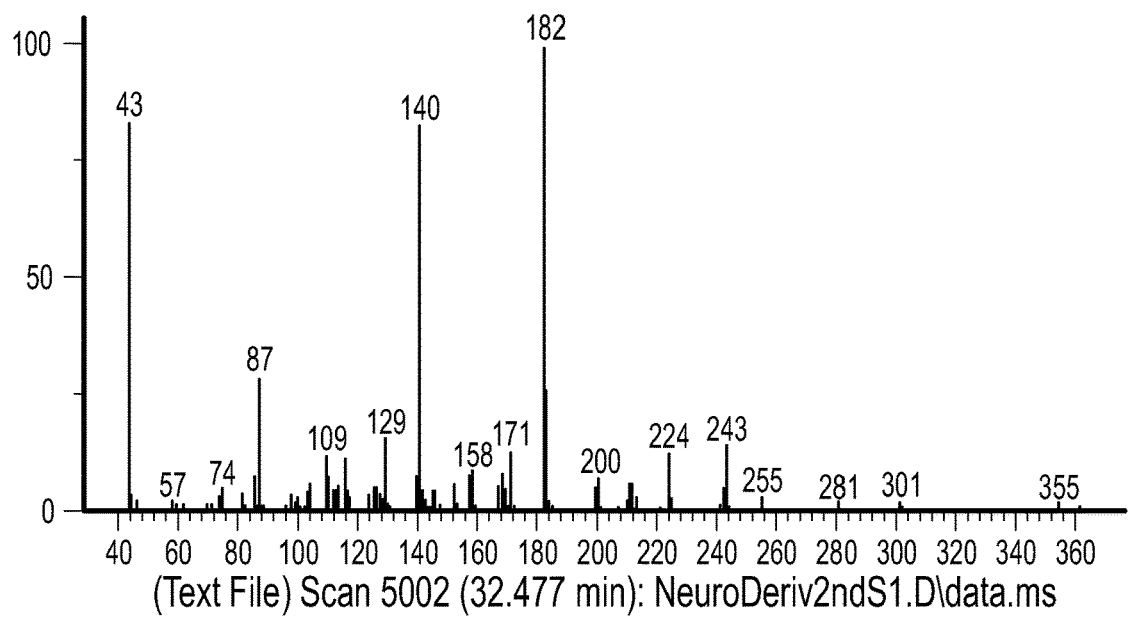
FIG. 20 is a fragmentation pattern of 3,5-diacetoxy benzyl alcohol. The peak fragmentation pattern is in the top panel, the compound library fragmentation match is in the bottom panel, and an overlay of the two is in the center panel.
Figure 20:
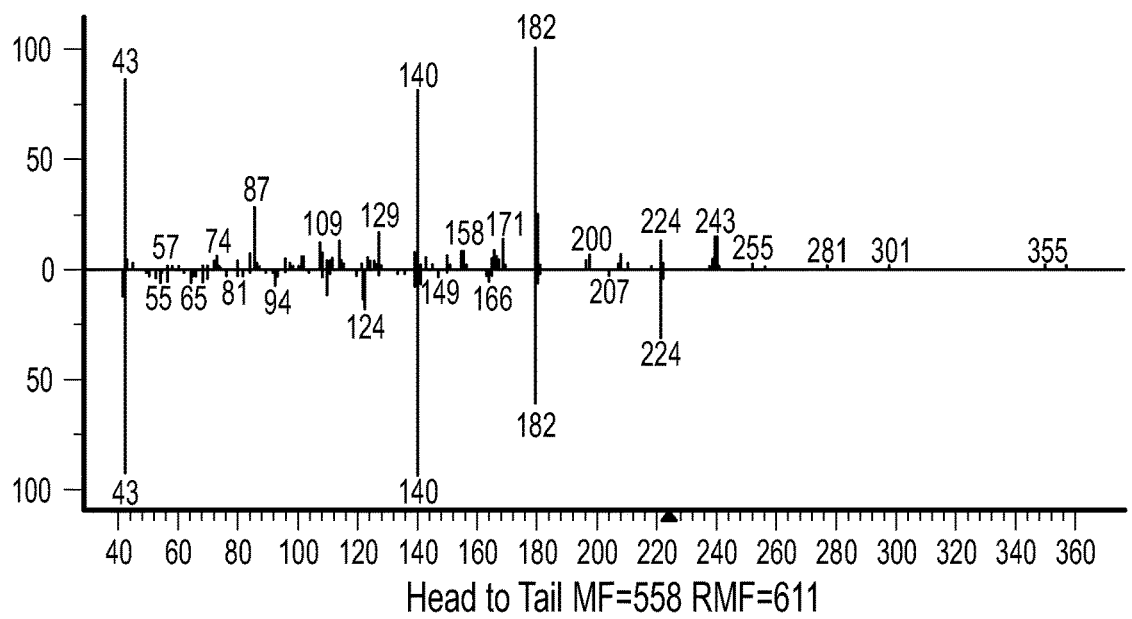
Figure 20:
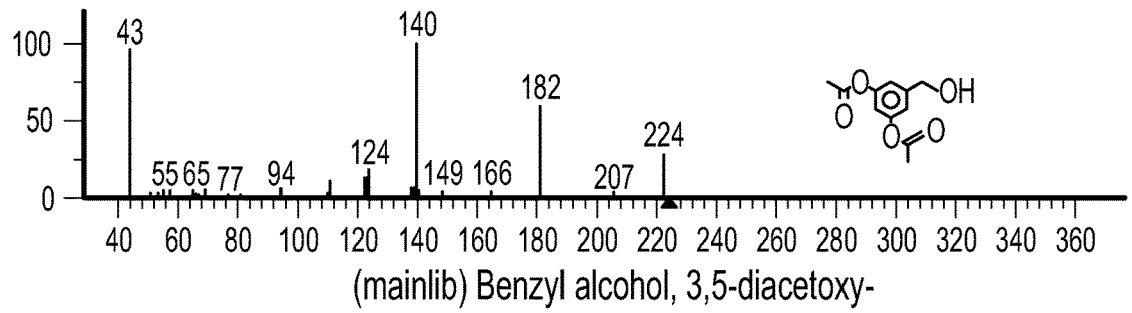
Figure 21:
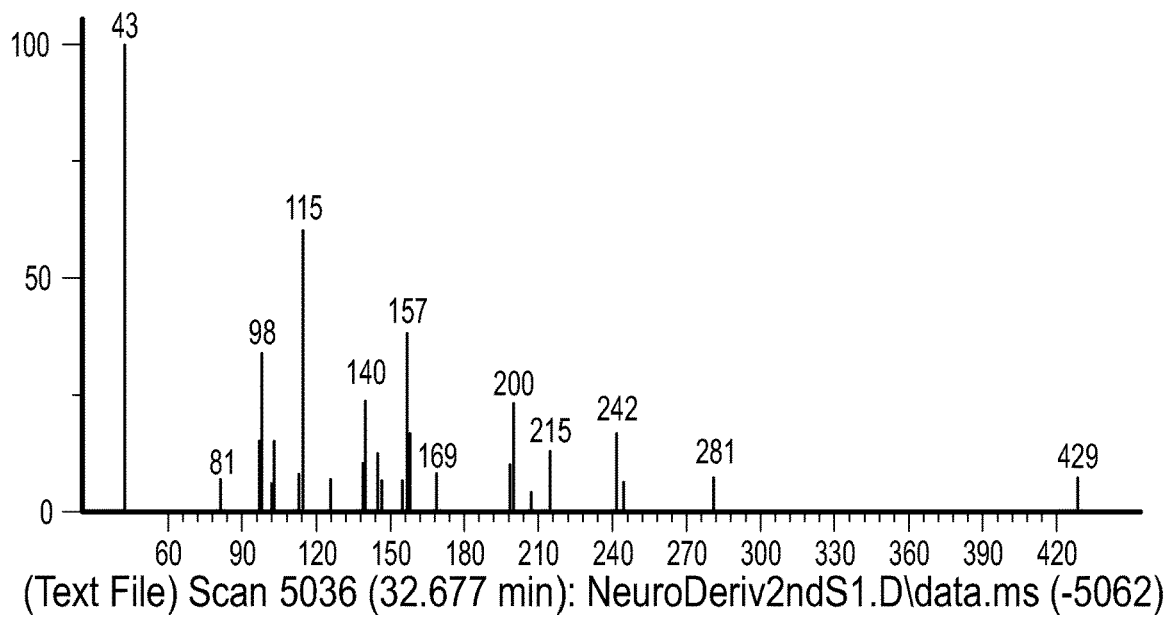
FIG. 21 is a fragmentation pattern of β-D-galactopyranose, pentaacetate. The peak fragmentation pattern is in the top panel, the compound library fragmentation match is in the bottom panel, and an overlay of the two is in the center panel.
Figure 21:
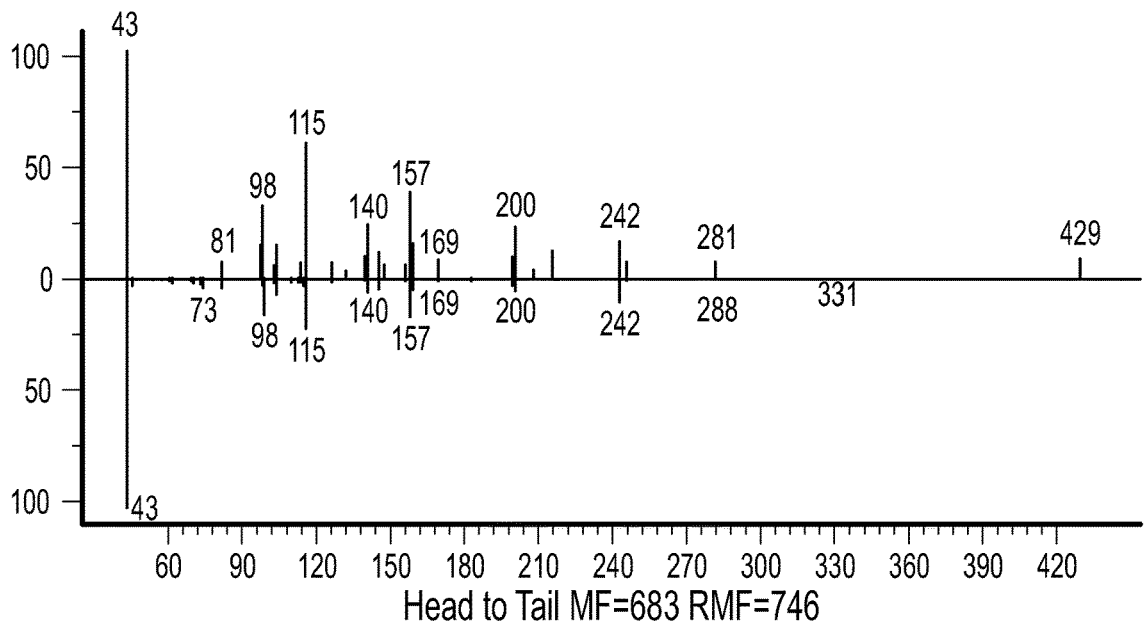
Figure 21:
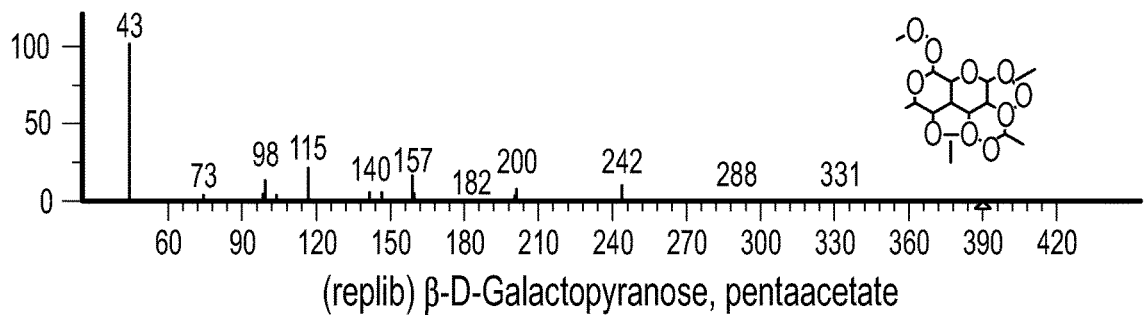
Figure 22:
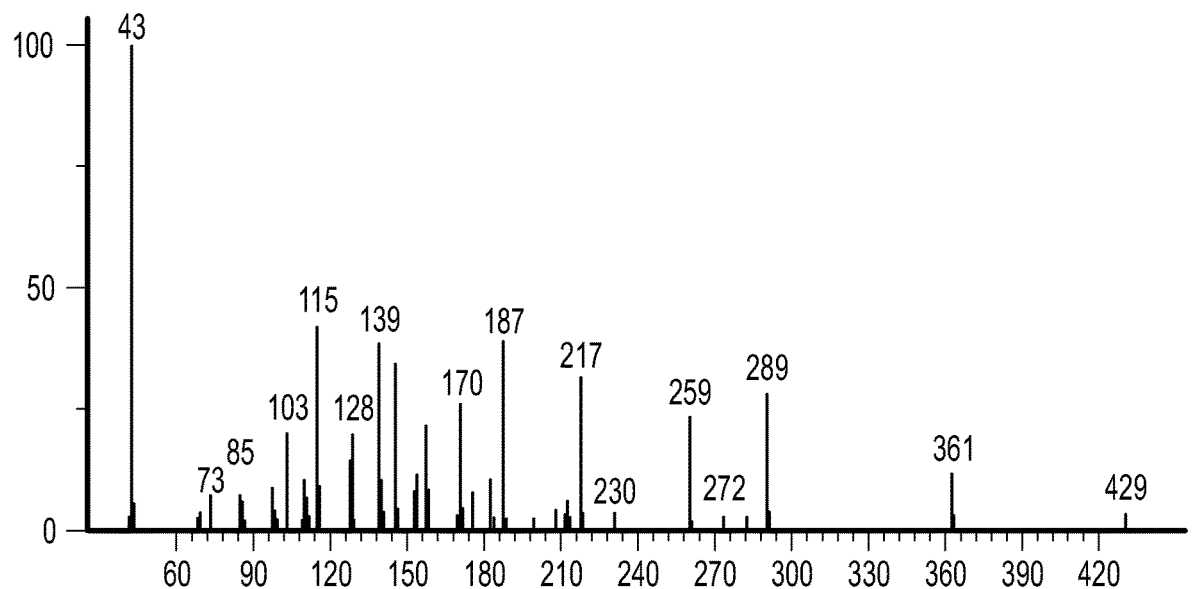
FIG. 22 is a fragmentation pattern of D-mannitol hexaacetate. The peak fragmentation pattern is in the top panel, the compound library fragmentation match is in the bottom panel, and an overlay of the two is in the center panel.
Figure 22:
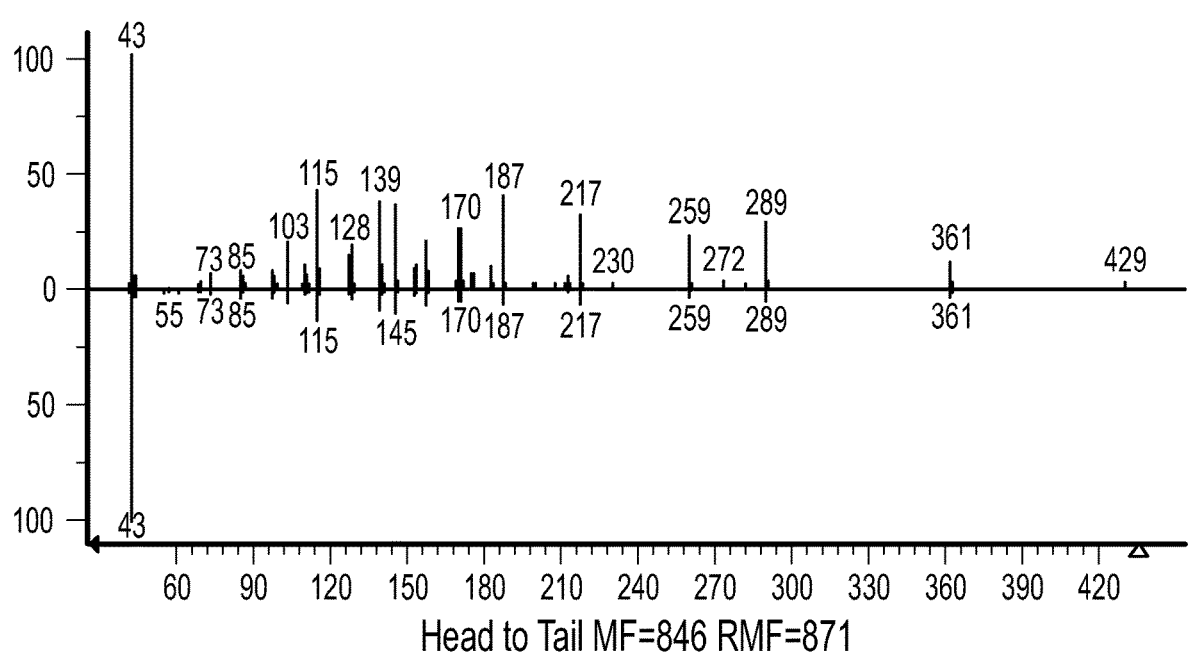
Figure 22:
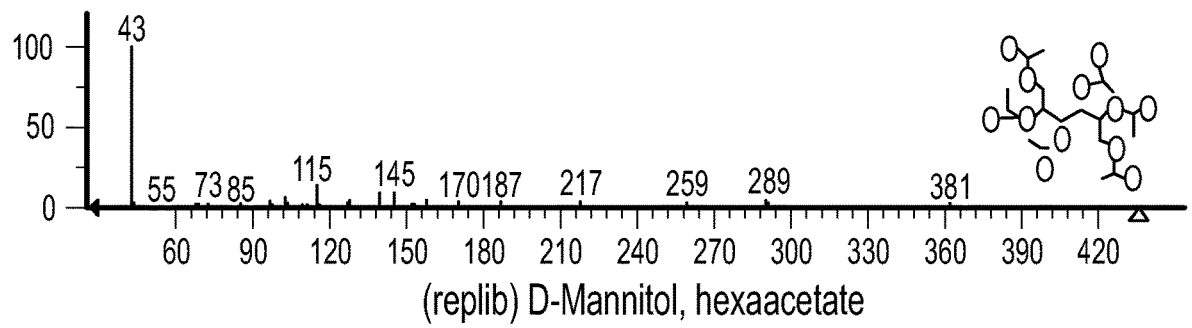
Figure 23:
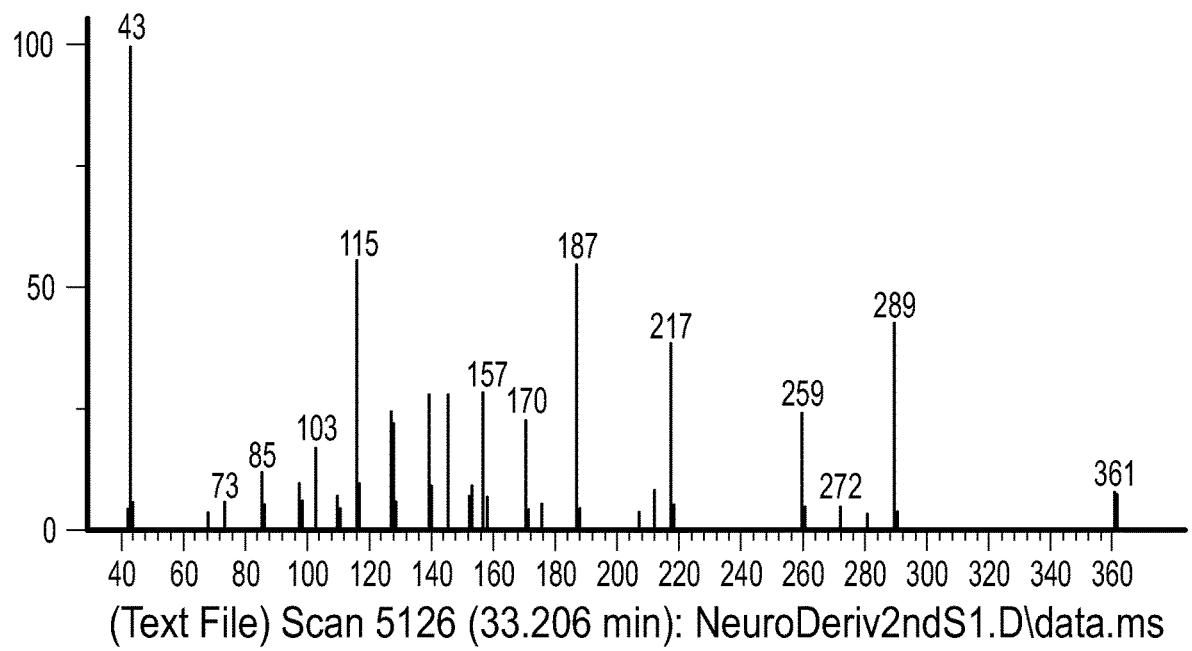
FIG. 23 is a fragmentation pattern of galacticol, hexaacetate. The peak fragmentation pattern is in the top panel, the compound library fragmentation match is in the bottom panel, and an overlay of the two is in the center panel.
Figure 23:
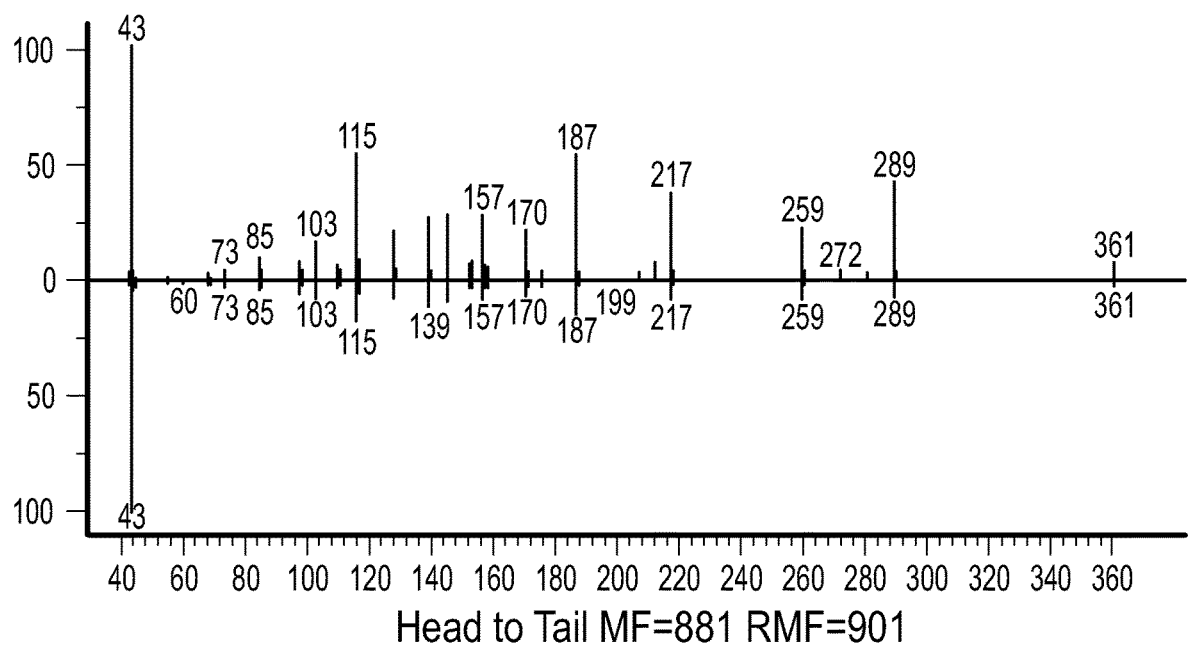
Figure 23:
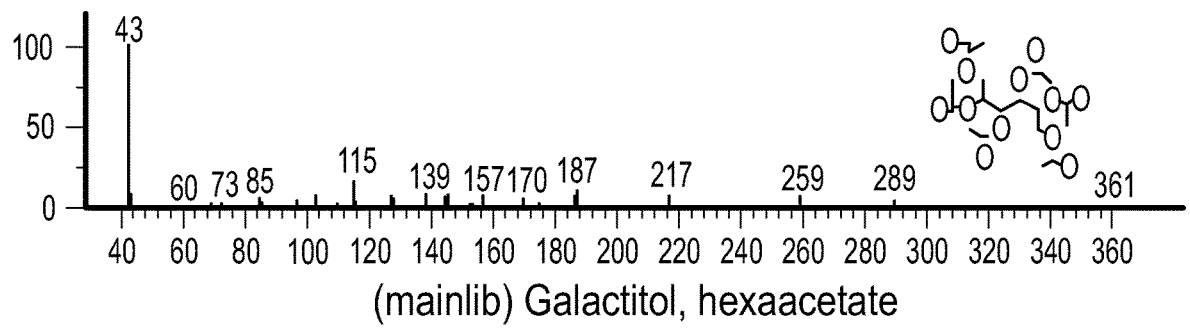
Figure 24:
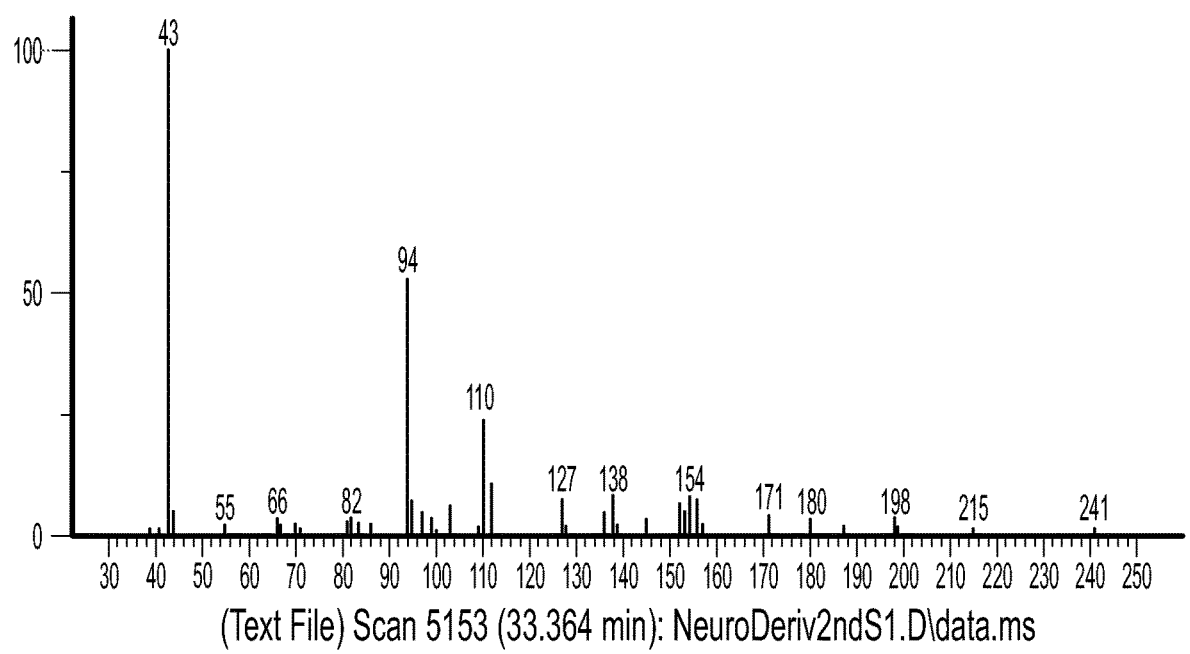
FIG. 24 is a fragmentation pattern of cyclohexane carboxylic acid, 1,2,4,5-tetrakis(acetoxy), (1α,3α,4α,5β)-(−). The peak fragmentation pattern is in the top panel, the compound library fragmentation match is in the bottom panel, and an overlay of the two is in the center panel.
Figure 24:
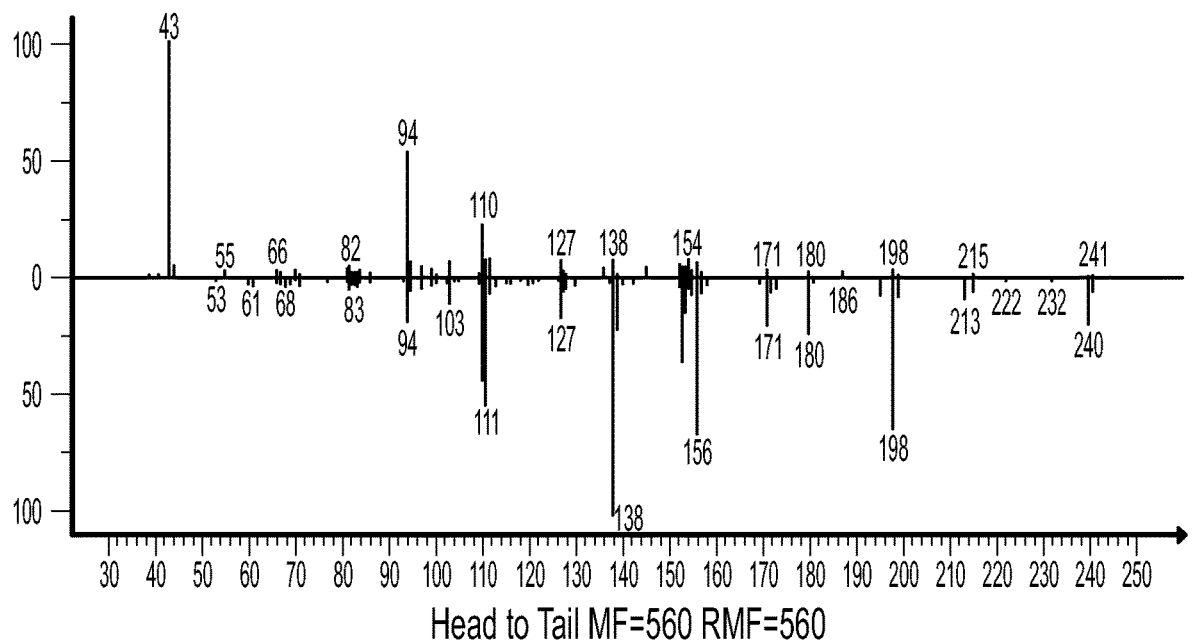
Figure 24:
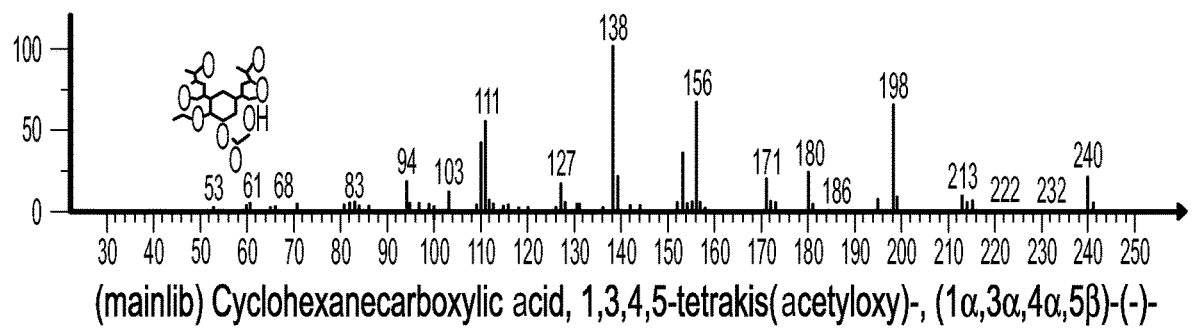
Figure 25:
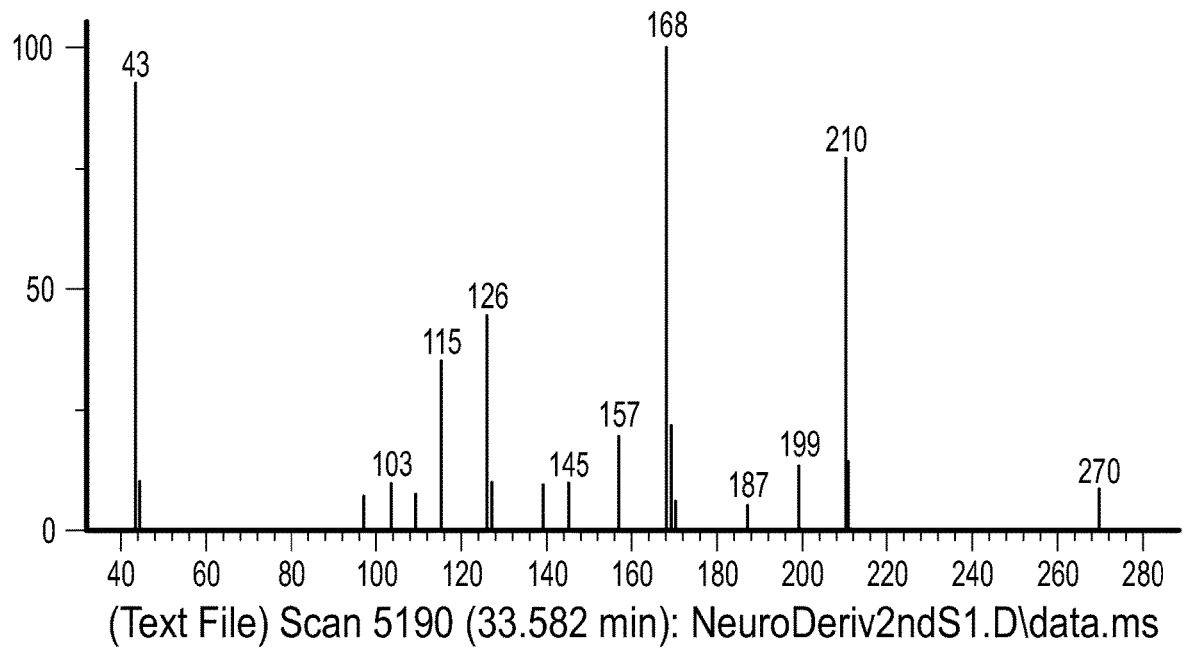
FIG. 25 is a fragmentation pattern of muco-inositol, hexaacetate. The peak fragmentation pattern is in the top panel, the compound library fragmentation match is in the bottom panel, and an overlay of the two is in the center panel.
Figure 25:
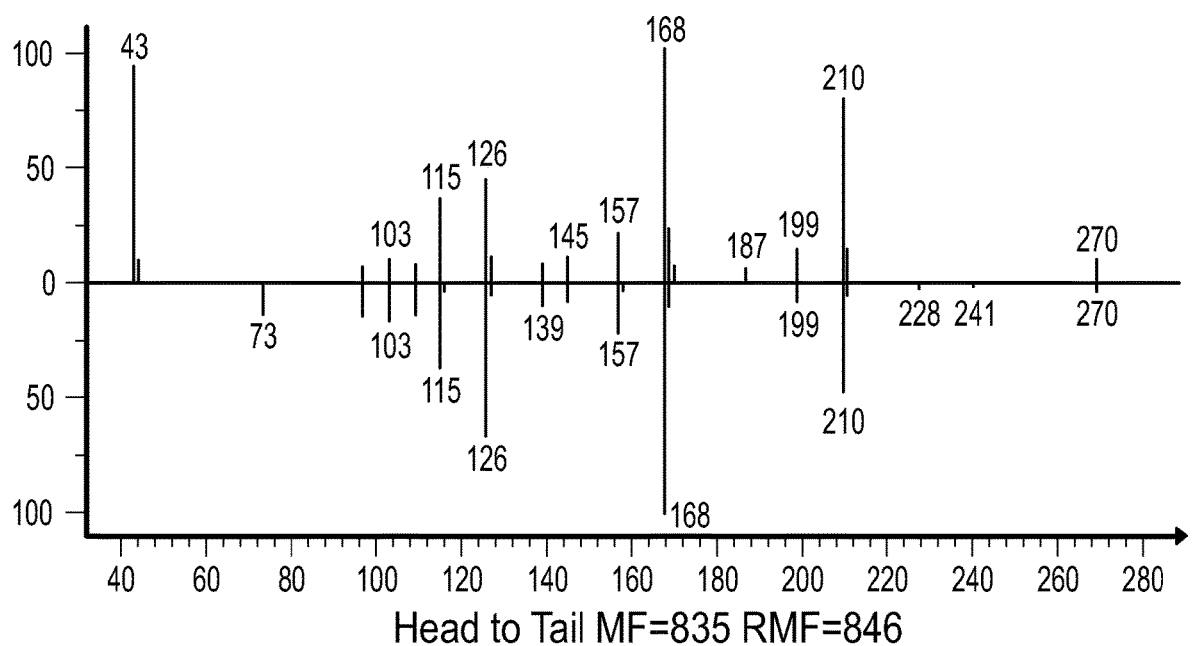
Figure 25:
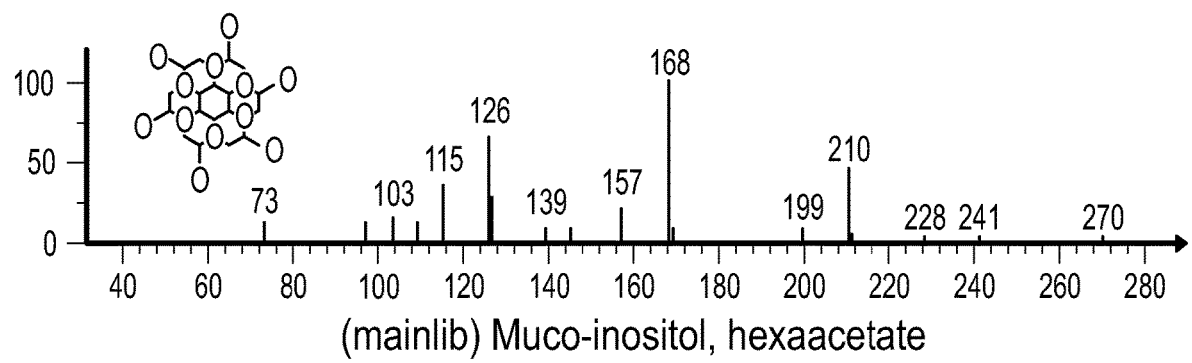
Figure 26:
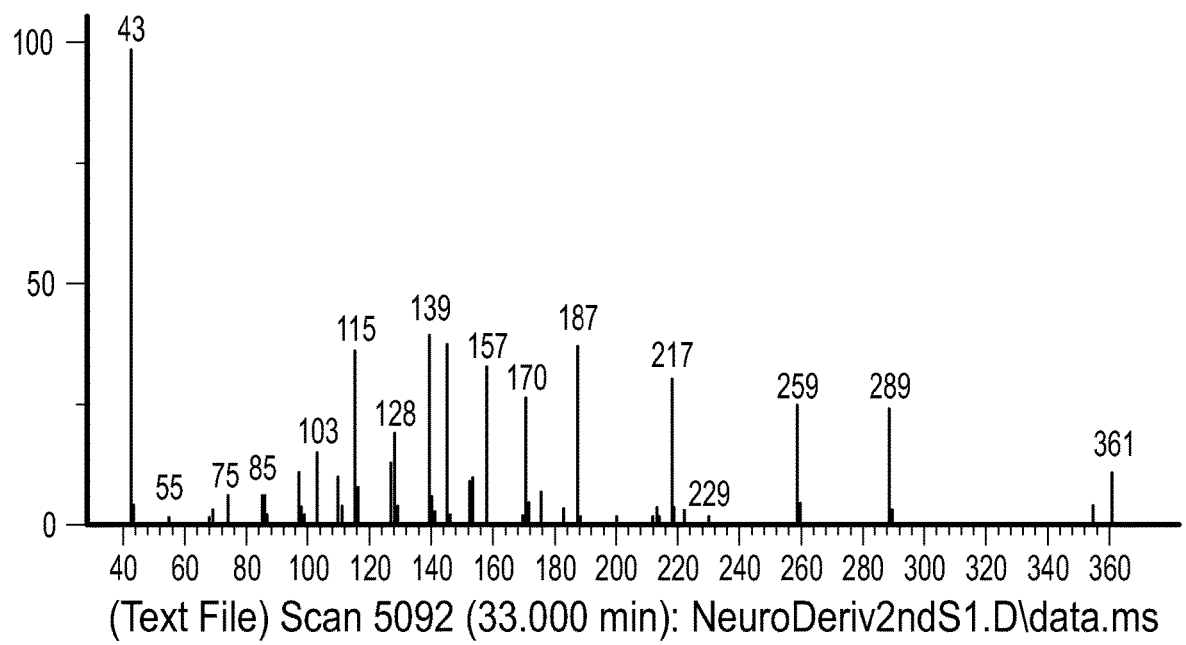
FIG. 26 is a fragmentation pattern of D-glucitol-hexaacetate. The peak fragmentation pattern is in the top panel, the compound library fragmentation match is in the bottom panel, and an overlay of the two is in the center panel.
Figure 26:
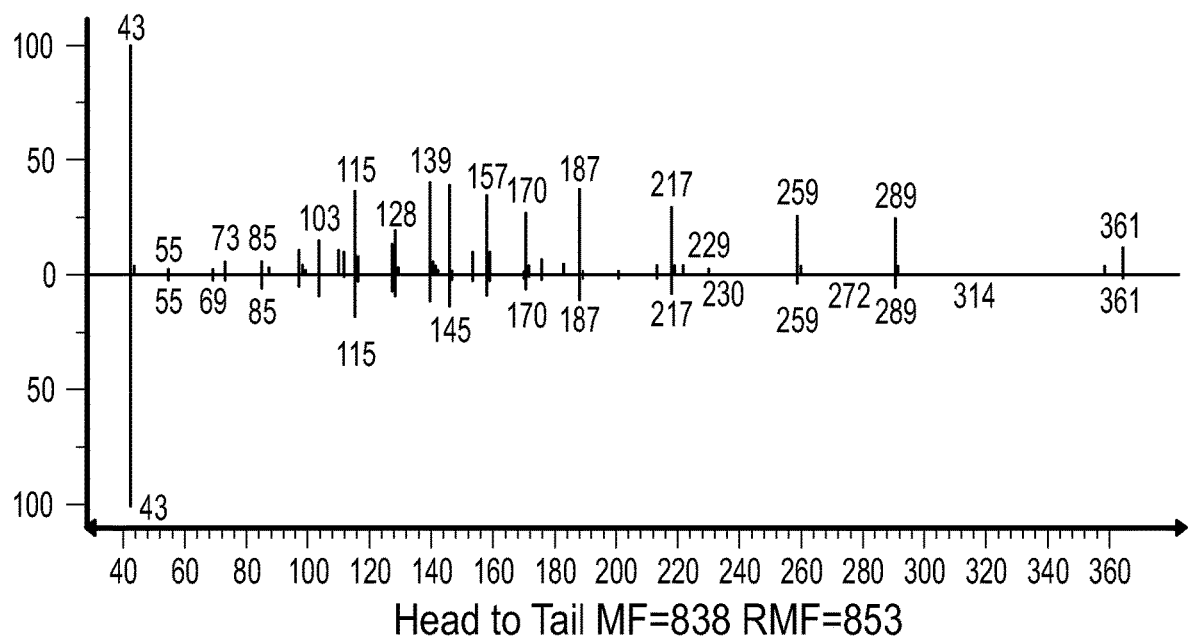
Figure 26:
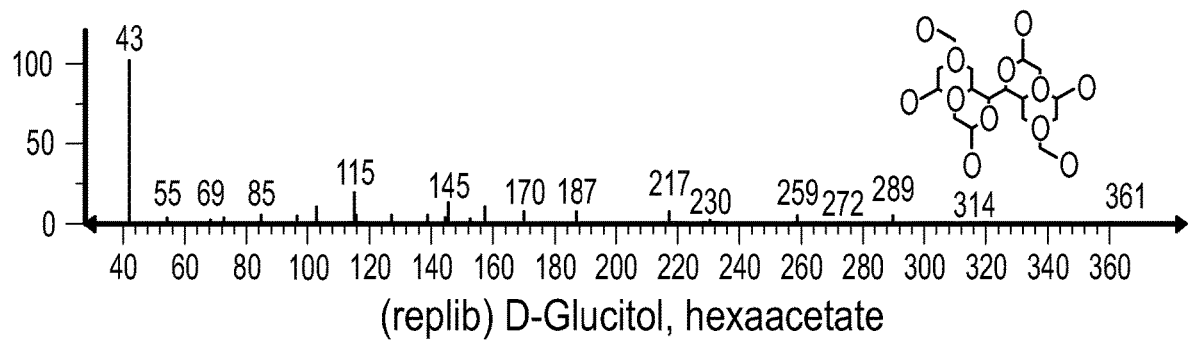
Figure 27:
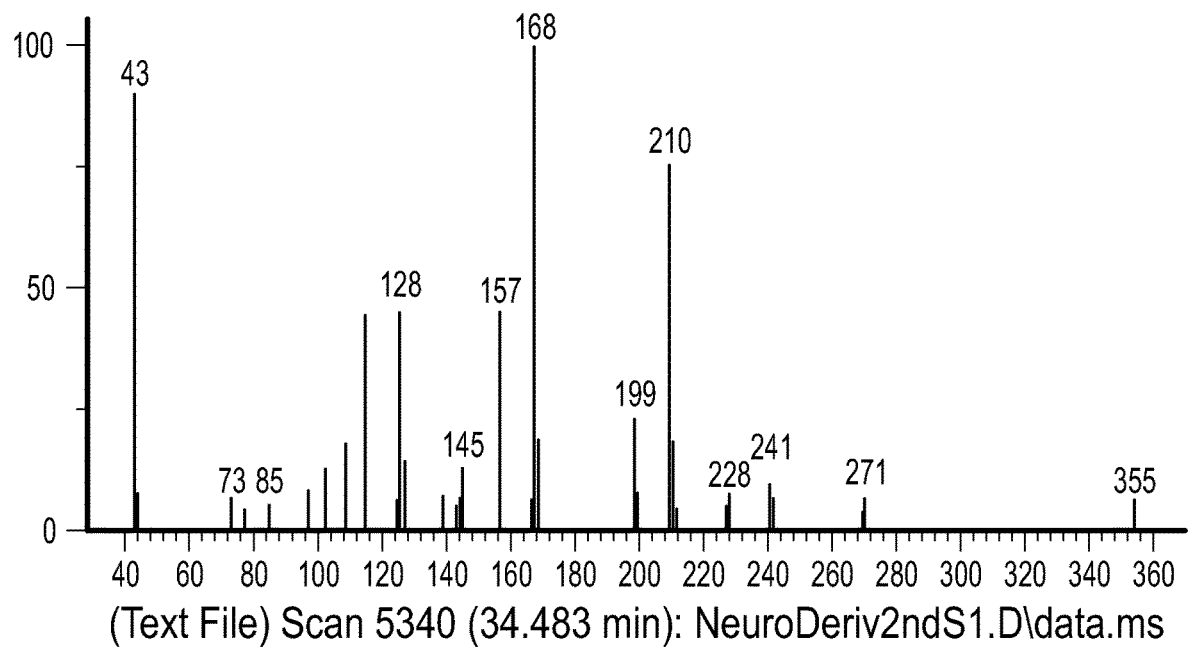
FIG. 27 is a fragmentation pattern of myo-inositol, hexaacetate. The peak fragmentation pattern is in the top panel, the compound library fragmentation match is in the bottom panel, and an overlay of the two is in the center panel.
Figure 27:
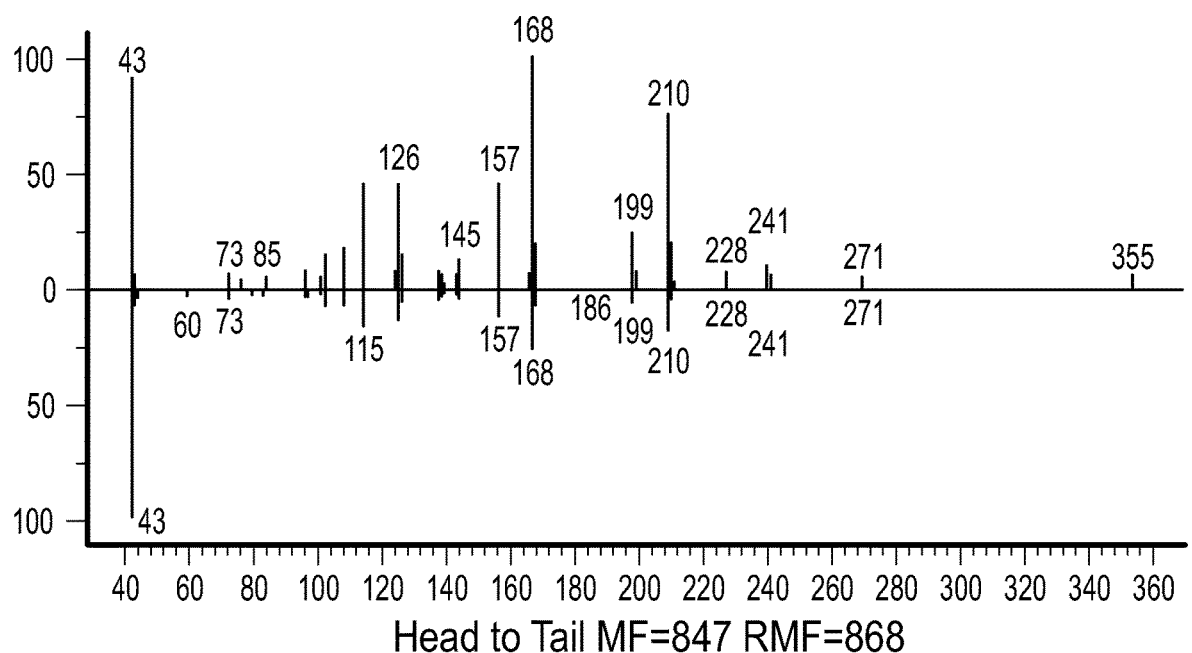
Figure 27:
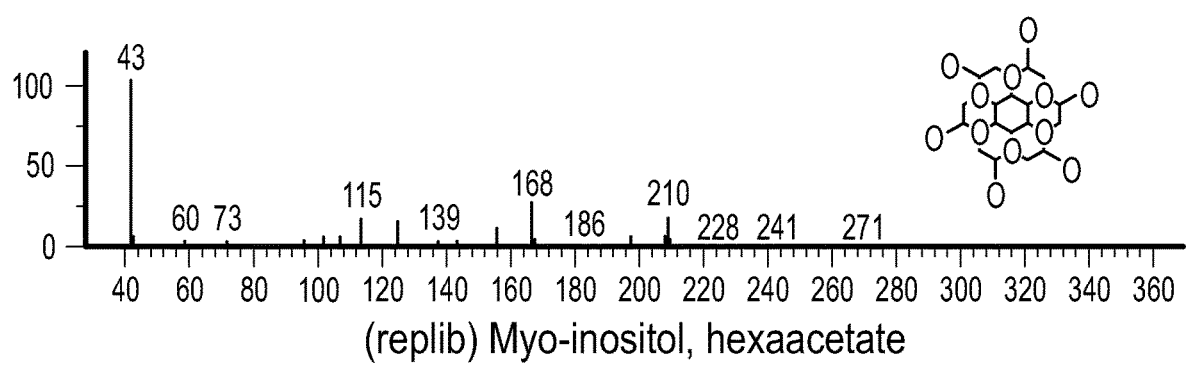
Figure 28:
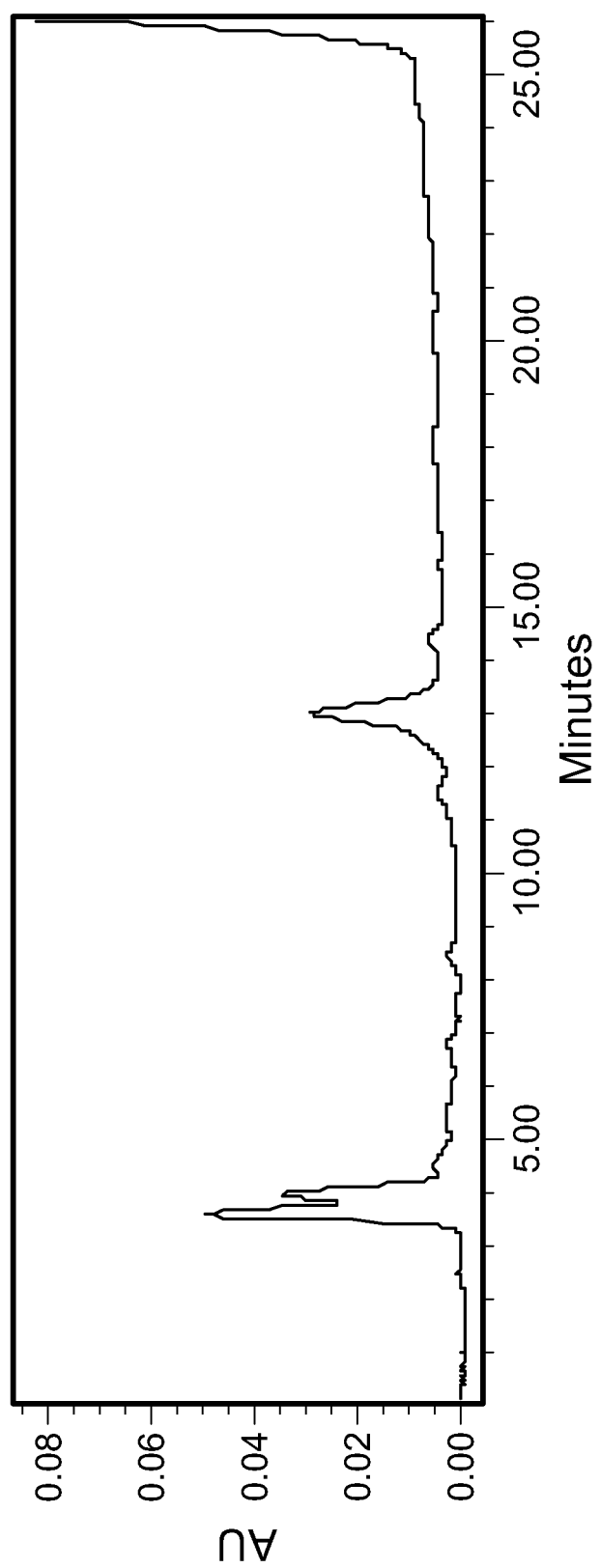
FIG. 28 is an HPLC chromatogram of a 10% ACN extract of raw Organic Yellow potato.
Figure 29:
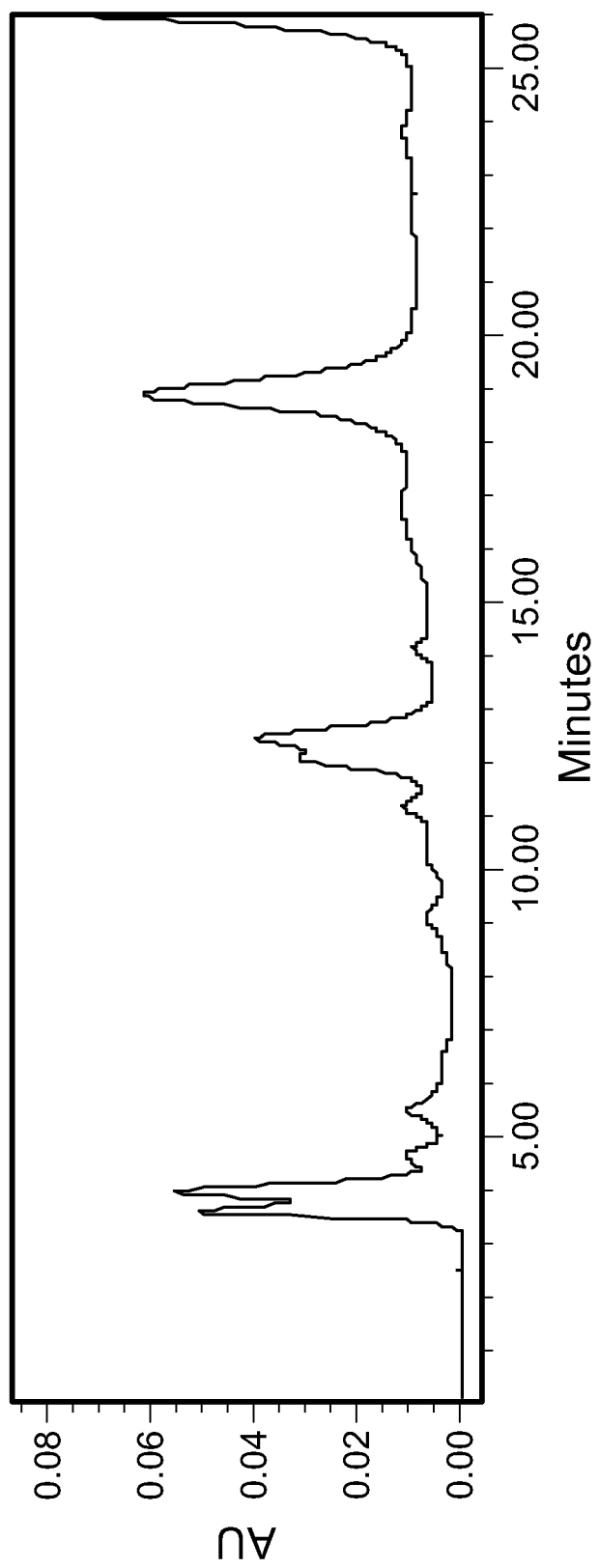
FIG. 29 is an HPLC chromatogram of a 10% ACN extract of raw Purple potato.
Figure 30:
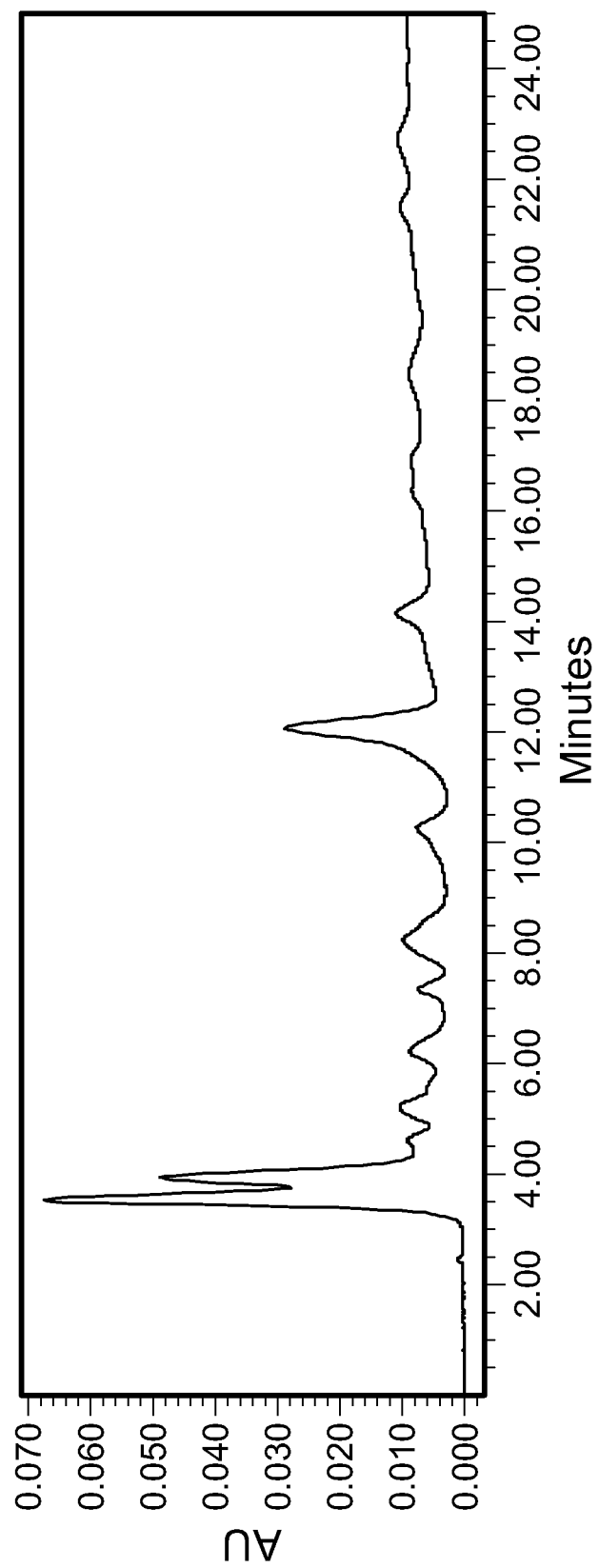
FIG. 30 is an HPLC chromatogram of a 10% ACN extract of raw Idaho Russet potato.
Figure 31:
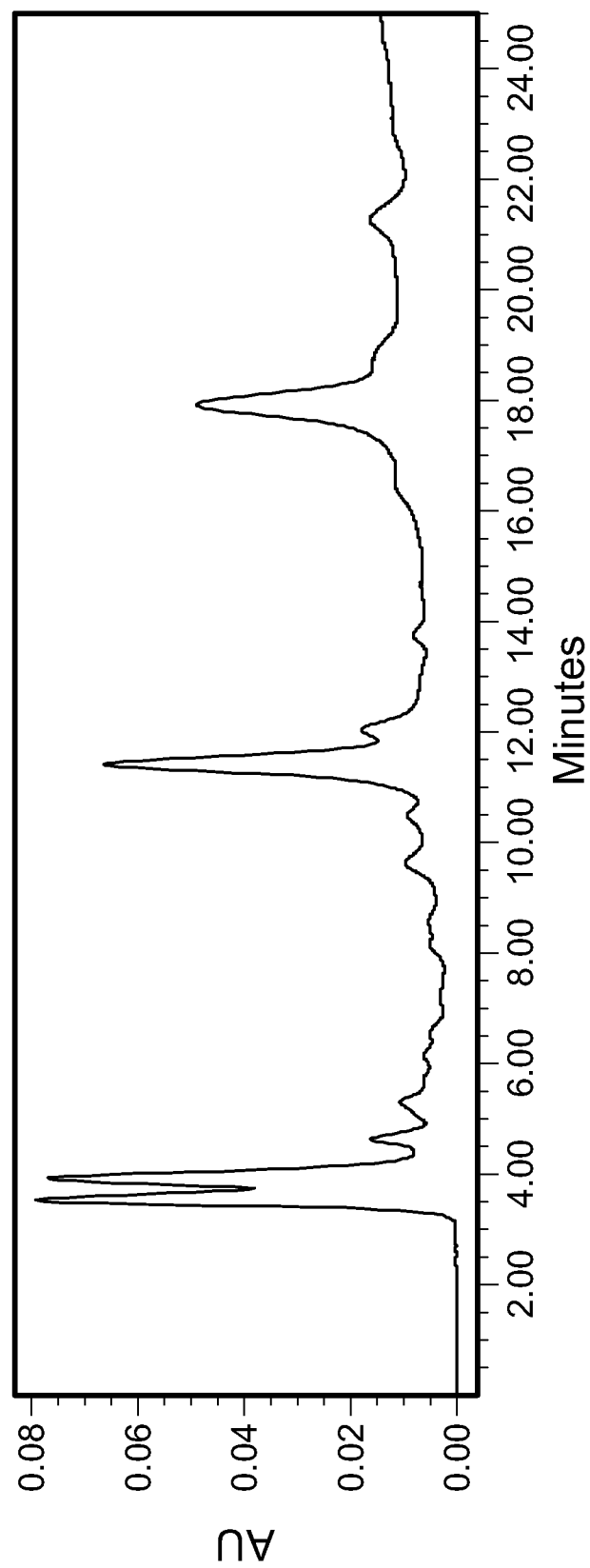
FIG. 31 is an HPLC chromatogram of a 10% ACN extract of raw Yukon Gold potato.
Figure 32:
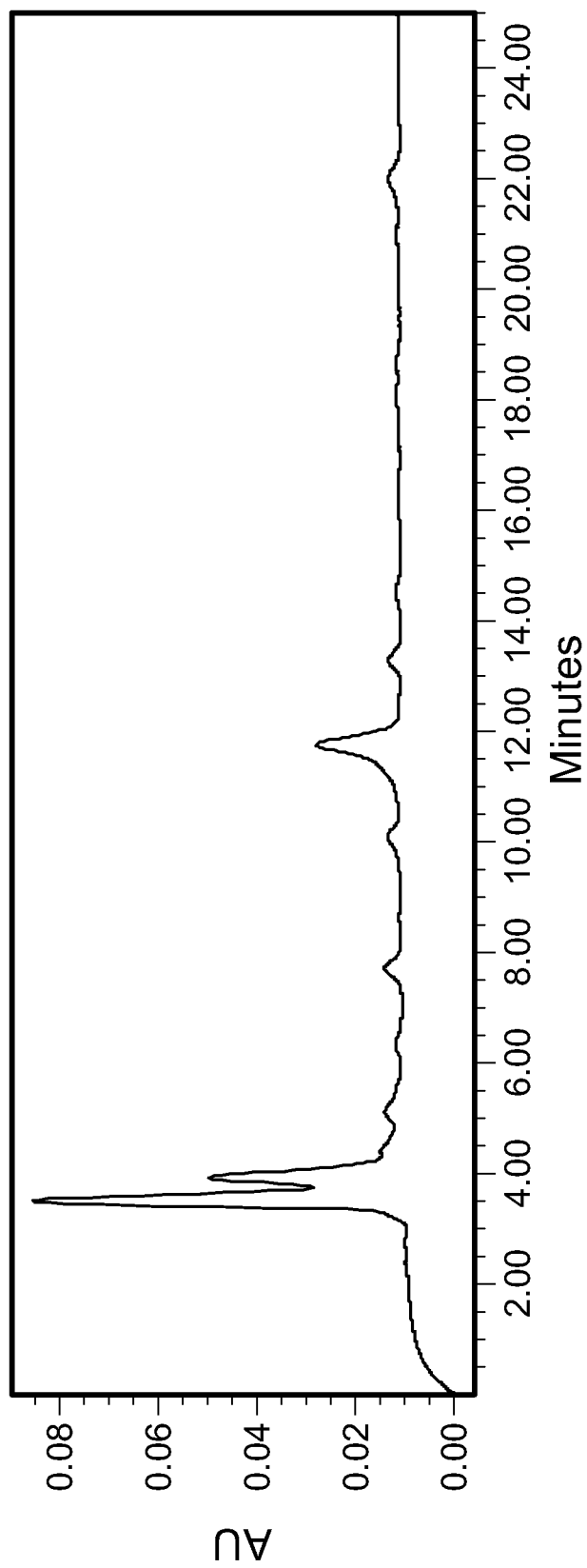
FIG. 32 is an HPLC chromatogram of a 10% ACN extract of raw sweet potato.

In some cases, a potato polysaccharide preparation can be a preparation that is obtained from potato and that contains polysaccharide material that, when derivatized and assessed using GC/MS, results in at least four major components (3,4-furan dimethanol, diacetate; 1,2,3,4,5-penta-o-acetyl-D-xylitol (isomer 1); 3,5-diacetoxy-benzyl alcohol; and D-glucitol-hexaacetate). See, e.g., Example 1. In some cases, a potato polysaccharide preparation can be a preparation that is obtained from potato and that contains polysaccharide material that, when derivatized and assessed using GC/MS, results in the compounds listed in Table 3 or results in the profile shown in FIG. 7.

In some cases, a potato polysaccharide preparation provided herein can be a substantially pure potato polysaccharide preparation. Typically, a substantially pure potato polysaccharide preparation is a preparation that contains a single peak of material (e.g., a single peak of polysaccharide material) when assessed using, for example, HPLC (see, e.g., FIGS. 2 and 34). In some cases, greater than 60, 70, 75, 80, 85, 90, 95, or 99 percent of a potato polysaccharide preparation provided herein can be polysaccharide material obtained from a potato.

Any appropriate potato species or variety can be used to obtain a potato polysaccharide preparation provided herein. For example, Solanum tuberosum, Ipomoea batatas, S. acaule, S. bukasovii, S. leptophyes, S. megistacrolobum, S. commersonii, or S. infundibuliforme can be used to obtain a potato polysaccharide preparation provided herein. In some cases, potato varieties of S. tunerosum such as Organic Yellow, Purple or blue varieties, Cream of the Crop, Adirondack Blue, Adirondack Red, Agata, Almond, Andes Gold, Andes Sun, Apline, Alturas, Amandine, Annabelle, Anya, Arran Victory, Atlantic, Avalanche, Bamberg, Bannock Russet, Belle de Fontenay, BF-15, Bildtstar, Bintje, Blazer Russet, Blue Congo, Bonnotte, British Queens, Cabritas, Camota, Canela Russet, Cara, Carola, Chelina, Chiloé, Cielo, Clavela Blanca, Désirée, Estima, Fianna, Fingerling, Flava, German Butterball, Golden Wonder, Goldrush, Home Guard, Innovator, Irish Cobbler, Jersey Royal, Kennebec, Kerr's Pink, Kestrel, Keuka Gold, King Edward, Kipfler, Lady Balfour, Langlade, Linda, Marcy, Marfona, Maris Piper, Marquis, Megachip, Monalisa, Nicola, Pachacoña, Pike, Pink Eye, Pink Fir Apple, Primura, Ranger Russet, Ratte, Record, Red LaSoda, Red Norland, Red Pontiac, Rooster, Russet Burbank, Russet Norkotah, Selma, Shepody, Sieglinde, Silverton Russet, Sirco, Snowden, Spunta, Up to date, Stobrawa, Superior, Vivaldi, Vitelotte, Yellow Finn, or Yukon Gold can be used to obtain a potato polysaccharide preparation provided herein.

Any appropriate method can be used to obtain a potato polysaccharide preparation provided herein. For example, raw potato material can be homogenized (e.g., homogenized with a Polytron homogenizer) in water and maintained at room temperature for a period of time (e.g., about 1 hour) with occasional shaking. The homogenate can be centrifuged (e.g., centrifuged at 4000 g for 10 minutes) to remove any larger solid material. The resulting supernatant can be loaded onto a Solid Phase Extraction cartridge (e.g., a C18 cartridge such as a Sep-Pak Plus C-18 cartridge), and the polysaccharide material eluted with 10 percent acetonitrile. Once eluted, the polysaccharide material can be dried and stored (e.g., stored at about 4° C.).

This document also provides nutritional supplement compositions containing one or more potato polysaccharide preparations provided herein. For example, a potato polysaccharide preparation provided herein obtained from Idaho Russet potatoes can be formulated into a nutritional supplement composition.

Any appropriate dose of a potato polysaccharide preparation provided herein can be used to formulate a composition provided herein (e.g., a nutritional supplement composition or potato polysaccharide preparation provided herein). For example, a potato polysaccharide preparation provided herein can be used to formulate a composition for treating diabetes and/or liver steatosis such that the composition contains between about 1 mg and about 750 mg (e.g., between about 1 mg and about 500 mg, between about 1 mg and about 250 mg, between about 5 mg and about 40 mg, between about 5 mg and about 30 mg, between about 5 mg and about 20 mg, between about 6 mg and about 50 mg, between about 6 mg and about 20 mg, between about 10 mg and about 25 mg, or between about 15 mg and about 20 mg) of the potato polysaccharide component of the potato polysaccharide preparation. In some cases, a composition (e.g., a nutritional supplement composition) can be formulated to deliver about 0.05 mg of the potato polysaccharide component per kg of body weight to about 0.5 mg of the potato polysaccharide component per kg of body weight to a mammal (e.g., a human) per day. For example, a nutritional supplement composition can be formulated into a single oral composition that a human can swallow once a day to provide between about 0.05 mg of the potato polysaccharide component per kg of body weight to about 0.5 mg of the potato polysaccharide component per kg of body weight.

Any appropriate method can be used to formulate a composition provided herein (e.g., a nutritional supplement composition or potato polysaccharide preparation provided herein). For example, common formulation mixing and preparation techniques can be used to make a composition (e.g., a nutritional supplement composition) having the components described herein. In addition, a composition provided herein (e.g., a nutritional supplement composition or potato polysaccharide preparation provided herein) can be in any form. For example, a composition provided herein (e.g., a nutritional supplement composition or potato polysaccharide preparation provided herein) can be formulated into a pill, capsule, tablet, gelcap, nutritional shake, nutritional bar, rectal supository, sublingual suppository, nasal spray, inhalant, or injectable ampule. In some cases, a composition provided herein (e.g., a nutritional supplement composition) can include one or more potato polysaccharide preparations provided herein alone or in combination with other ingredients including, without limitation, gelatin, cellulose, starch, sugar, bentonite, lactic acid, mannitol, alpha lipoic acid, alpha tocopherol, L-ascorbate, or combinations thereof.

This document also provides methods for increasing or decreasing expression of polypeptides involved with mitochondria activity or function. For example, a potato polysaccharide preparation provided herein or a nutritional supplement composition provided herein can be used to increase or decrease expression of polypeptides involved with mitochondria activity or function. In some cases, a potato polysaccharide preparation provided herein or a nutritional supplement composition provided herein can be used to increase expression of a TFAM polypeptide, an ATP5A1 polypeptide, a PDHA1 polypeptide, a PDHA2 polypeptide, a THOP1 polypeptide, or a combination thereof. In some cases, a potato polysaccharide preparation provided herein or a nutritional supplement composition provided herein can be used to decrease expression of a FOX01A polypeptide, a NFKB1 polypeptide, a PDK2 polypeptide, a PDK4 polypeptide, a HMGCR polypeptide, or a combination thereof. In some case, a potato polysaccharide preparation provided herein or a nutritional supplement composition provided herein can be used to increase one or more polypeptides (e.g., one or more of a TFAM polypeptide, an ATP5A1 polypeptide, a PDHA1 polypeptide, a PDHA2 polypeptide, or a THOP1 polypeptide) and decrease one or more polypeptides (e.g., one or more of a FOX01A polypeptide, a NFKB1 polypeptide, a PDK2 polypeptide, a PDK4 polypeptide, or a HMGCR polypeptide).

In humans, a potato polysaccharide preparation provided herein or a nutritional supplement composition provided herein can be used to increase one or more human polypeptides (e.g., one or more of a human TFAM polypeptide, a human ATP5A1 polypeptide, a human PDHA1 polypeptide, a human PDHA2 polypeptide, a human THOP1 polypeptide, a human LIPE polypeptide (in adipocytes), a human PCK2 polypeptide, a human MOGAT1 polypeptide, a human PPARGC1a polypeptide, a vPPARGC1b polypeptide, an human SOD2 polypeptide, a human NR4A1 polypeptide (in adipocytes), a human ACAT2 polypeptide, or a human HMGCR polypeptide (in muscle cells)) and/or decrease one or more human polypeptides (e.g., one or more of a human FOX01A polypeptide, a human NFKB1 polypeptide, a human PDK2 polypeptide, a human PDK4 polypeptide, a human HMGCR polypeptide (in adipocytes), a human AGPAT1 polypeptide, a human OLR1 polypeptide, a human BCAT2 polypeptide, a human SH2B1 polypeptide, a human LPL polypeptide, a human HMGCR polypeptide (in adipocytes), a human LIPE polypeptide (in muscle cells), a human NR4A1 polypeptide (in muscle cells), a human PTEN polypeptide, or a human CASP8 polypeptide).

A human TFAM polypeptide can have the amino acid sequence set forth in GenBank® Accession No. CAG28581.1 (GI No. 47115243) and can be encoded by the nucleic acid sequence set forth in GenBank® Accession No. NM_003201.1 (GI No. 4507400). A human ATP5A1 polypeptide can have the amino acid sequence set forth in GenBank® Accession No. AAH08028.2 (GI No. 34782901) and can be encoded by the nucleic acid sequence set forth in GenBank® Accession No. NM_001001937.1 (GI No. 50345983). A human PDHA1 polypeptide can have the amino acid sequence set forth in GenBank® Accession No. ABQ58815.1 (GI No. 148300624) and can be encoded by the nucleic acid sequence set forth in GenBank® Accession No. NM_001173454.1 (GI No. 291084741). A human PDHA2 polypeptide can have the amino acid sequence set forth in GenBank® Accession No. AAH94760.1 (GI No. 66267554) and can be encoded by the nucleic acid sequence set forth in GenBank® Accession No. NM_005390.4 (GI No. 134031963). A human THOP1 polypeptide can have the amino acid sequence set forth in GenBank® Accession No. AAH00583.2 (GI No. 38014202) and can be encoded by the nucleic acid sequence set forth in GenBank® Accession No. NM_003249.3 (GI No. 34222291). A human LIPE polypeptide can have the amino acid sequence set forth in GenBank® Accession No. AAH70041.1 (GI No. 47124456) and can be encoded by the nucleic acid sequence set forth in GenBank® Accession No. NM_005357.2 (GI No. 21328445). A human PCK2 polypeptide can have the amino acid sequence set forth in GenBank® Accession No. CAG33194.1 (GI No. 48145943) and can be encoded by the nucleic acid sequence set forth in GenBank® Accession No. NM_004563.1 (GI No. 66346720). A human MOGAT1 polypeptide can have the amino acid sequence set forth in GenBank® Accession No. NP_477513.2 (GI No. 148746191) and can be encoded by the nucleic acid sequence set forth in GenBank® Accession No. NM_058165.1 (GI No. 148746190). A human PPARGC1a polypeptide can have the amino acid sequence set forth in GenBank® Accession No. NP_037393.1 (GI No. 7019499) and can be encoded by the nucleic acid sequence set forth in GenBank® Accession No. NM_013261.2 (GI No. 116284374). A human PPARGC1b polypeptide can have the amino acid sequence set forth in GenBank® Accession No. AAI44252.1 (GI No. 219518198) and can be encoded by the nucleic acid sequence set forth in GenBank® Accession No. NM_133263.2 (GI No. 289577087). A human SOD2 polypeptide can have the amino acid sequence set forth in GenBank® Accession No. AAH16934.1 (GI No. 16877367) and can be encoded by the nucleic acid sequence set forth in GenBank® Accession No. NM_000636.1 (GI No. 67782304). A human NR4A1 polypeptide can have the amino acid sequence set forth in GenBank® Accession No. CAG32985.1 (GI No. 48145525) and can be encoded by the nucleic acid sequence set forth in GenBank® Accession No. NM_173158.1 (GI No. 320202954). A human ACAT2 polypeptide can have the amino acid sequence set forth in GenBank® Accession No. AAH00408.1 (GI No. 12653279) and can be encoded by the nucleic acid sequence set forth in GenBank® Accession No. NM_005891.1 (GI No. 148539871). A human FOX01A polypeptide can have the amino acid sequence set forth in GenBank® Accession No. NP_002006.2 (GI No. 9257222) and can be encoded by the nucleic acid sequence set forth in GenBank® Accession No. NM_002015.3 (GI No. 133930787). A human NFKB1 polypeptide can have the amino acid sequence set forth in GenBank® Accession No. CAB94757.1 (GI No. 8574070) and can be encoded by the nucleic acid sequence set forth in GenBank® Accession No. NM_001165412.1 (GI No. 25955301). A human PDK2 polypeptide can have the amino acid sequence set forth in GenBank® Accession No. NP_002602.2 (GI No. 19923736) and can be encoded by the nucleic acid sequence set forth in GenBank® Accession No. NM_00211.4 (GI No. 315630394). A human PDK4 polypeptide can have the amino acid sequence set forth in GenBank® Accession No. AAH40239.1 (GI No. 25955471) and can be encoded by the nucleic acid sequence set forth in GenBank® Accession No. NM_002612.2 (GI No. 94421466). A human HMGCR polypeptide can have the amino acid sequence set forth in GenBank® Accession No. AAH33692.1 (GI No. 21707182) and can be encoded by the nucleic acid sequence set forth in GenBank® Accession No. NM_000859.2 (GI No. 196049378). A human AGPAT1 polypeptide can have the amino acid sequence set forth in GenBank® Accession No. NP_116130.2 (GI No. 15100175) and can be encoded by the nucleic acid sequence set forth in GenBank® Accession No. NM_006411.3 (GI No. 301336168). A human OLR1 polypeptide can have the amino acid sequence set forth in GenBank® Accession No. NP_002534.1 (GI No. 4505501) and can be encoded by the nucleic acid sequence set forth in GenBank® Accession No. NM_002543.2 (GI No. 119392084). A human BCAT2 polypeptide can have the amino acid sequence set forth in GenBank® Accession No. AAH04243.2 (GI No. 48257075) and can be encoded by the nucleic acid sequence set forth in GenBank® Accession No. NM_001190.1 (GI No. 258614013). A human SH2B1 polypeptide can have the amino acid sequence set forth in GenBank® Accession No. AAH10704.1 (GI No. 14715079) and can be encoded by the nucleic acid sequence set forth in GenBank® Accession No. NM_001145797.1 (GI No. 224926829). A human LPL polypeptide can have the amino acid sequence set forth in GenBank® Accession No. CAG33335.1 (GI No. 4814622) and can be encoded by the nucleic acid sequence set forth in GenBank® Accession No. NM_000237.1 (GI No. 145275217). A human HMGCR polypeptide can have the amino acid sequence set forth in GenBank® Accession No. AAH33692.1 (GI No. 21707182) and can be encoded by the nucleic acid sequence set forth in GenBank® Accession No. NM_001130996.1 (GI No. 196049379). A human PTEN polypeptide can have the amino acid sequence set forth in GenBank® Accession No. AAD13528.1 (GI No. 4240387) and can be encoded by the nucleic acid sequence set forth in GenBank® Accession No. NM_000314.2 (GI No. 110224474). A human CASP8 polypeptide can have the amino acid sequence set forth in GenBank® Accession No. AAH68050.1 (GI No. 45751586) and can be encoded by the nucleic acid sequence set forth in GenBank® Accession No. NM_001228.4 (GI No. 122056470).

In addition, this document provides methods for increasing expression of polypeptides involved in mitochondrial biogenesis linked to enhanced protein and nucleic acid biosynthesis. For example, a potato polysaccharide preparation provided herein or a nutritional supplement composition provided herein can be used to increase expression of polypeptides involved with mitochondrial biogenesis linked to enhanced protein and nucleic acid biosynthesis. In some cases, a potato polysaccharide preparation provided herein or a nutritional supplement composition provided herein can be used to increase expression of a Slc25a33 polypeptide, an Tomm40 polypeptide, a Mrp13 polypeptide, a Mrps18b polypeptide, a Mrps9 polypeptide, a Fars2 polypeptide, a Mrpl15 polypeptide, a Mrps23 polypeptide, a Mrps2 polypeptide, a Mrpl17 polypeptide, a TFAM polypeptide, or a combination thereof.

This document also provides methods for increasing expression of polypeptides involved in mitochondrial energy production. For example, a potato polysaccharide preparation provided herein or a nutritional supplement composition provided herein can be used to increase expression of polypeptides involved with mitochondrial energy production. In some cases, a potato polysaccharide preparation provided herein or a nutritional supplement composition provided herein can be used to increase expression of a Prodh polypeptide, an Slc25a1 polypeptide, a Hmgc1 polypeptide, a Cps1 polypeptide, a Aldh4a1 polypeptide, a Mdh2 polypeptide, a Atp5b polypeptide, a Slc25a22 polypeptide, a Slc25a19 polypeptide, a Uqcrc2 polypeptide, a Abcf2 polypeptide, or a combination thereof.

This document also provides methods for increasing or decreasing expression of polypeptides involved with lipogenesis, triglyceride assembly, and mitochondrial lipolysis. For example, a potato polysaccharide preparation provided herein or a nutritional supplement composition provided herein can be used to increase or decrease expression of polypeptides involved with lipogenesis, triglyceride assembly, and mitochondrial lipolysis. In some cases, a potato polysaccharide preparation provided herein or a nutritional supplement composition provided herein can be used to increase expression of an Acbd4 polypeptide, a Fads1 polypeptide, a Gnpat polypeptide, a Lypla1 polypeptide, a Cpt2 polypeptide, or a combination thereof. In some cases, a potato polysaccharide preparation provided herein or a nutritional supplement composition provided herein can be used to decrease expression of a Pck2 polypeptide, an Agpat4 polypeptide, an Acaca polypeptide, or a combination thereof. In some case, a potato polysaccharide preparation provided herein or a nutritional supplement composition provided herein can be used to increase one or more polypeptides (e.g., one or more of an Acbd4 polypeptide, a Fads1 polypeptide, a Gnpat polypeptide, a Lypla1 polypeptide, a Cpt2 polypeptide) and decrease one or more polypeptides (e.g., one or more of a Pck2 polypeptide, an Agpat4 polypeptide, an Acaca polypeptide).

In humans, a potato polysaccharide preparation provided herein or a nutritional supplement composition provided herein can be used to increase one or more human polypeptides (e.g., one or more of a Slc25a33 polypeptide, an Tomm40 polypeptide, a Mrpl3 polypeptide, a Mrps18b polypeptide, a Mrps9 polypeptide, a Fars2 polypeptide, a Mrpl15 polypeptide, a Mrps23 polypeptide, a Mrps2 polypeptide, a Mrpl17 polypeptide, a TFAM polypeptide, a Prodh polypeptide, an Slc25a1 polypeptide, a Hmgcl polypeptide, a Cps1 polypeptide, a Aldh4a1 polypeptide, a Mdh2 polypeptide, an Atp5b polypeptide, a Slc25a22 polypeptide, a Slc25a19 polypeptide, a Uqcrc2 polypeptide, an Abcf2 polypeptide, an Acbd4 polypeptide, a Fads1 polypeptide, a Gnpat polypeptide, a Lypla1 polypeptide, and a Cpt2 polypeptide (in liver cells)) and/or decrease one or more human polypeptides (e.g., one or more of a Pck2 polypeptide, an Agpat4 polypeptide, and an Acaca polypeptide (in liver cells)).

A human Slc25a33 polypeptide can have the amino acid sequence set forth in GenBank® Accession No. XP_005263560.1 (GI No. 530360655) and can be encoded by the nucleic acid sequence set forth in GenBank® Accession No. XM_005263503.1 (GI No. 530360654). A human Tomm40 polypeptide can have the amino acid sequence set forth in GenBank® Accession No. AAH47528.1 (GI No. 28839408) and can be encoded by the nucleic acid sequence set forth in GenBank® Accession No. NM_001128916.1 (GI No. 193083119). A human Mrpl3 polypeptide can have the amino acid sequence set forth in GenBank® Accession No. CAG33001.1 (GI No. 48145557) and can be encoded by the nucleic acid sequence set forth in GenBank® Accession No. NM_007208.3 (GI No. 312147300). A human Mrps18b polypeptide can have the amino acid sequence set forth in GenBank® Accession No. BAD13700.1 (GI No. 46091143) and can be encoded by the nucleic acid sequence set forth in GenBank® Accession No. NM_014046.3 (GI No. 186928836). A human Mrps9 polypeptide can have the amino acid sequence set forth in GenBank® Accession No. AAH47784.1 (GI No. 29126836) and can be encoded by the nucleic acid sequence set forth in GenBank® Accession No. NM_182640.2 (GI No. 186910309). A human Fars2 polypeptide can have the amino acid sequence set forth in GenBank® Accession No. NP_006558.1 (GI No. 5729820) and can be encoded by the nucleic acid sequence set forth in GenBank® Accession No. NM_006567.3 (GI No. 126513133). A human Mrpl15 polypeptide can have the amino acid sequence set forth in GenBank® Accession No. CAG38562.1 (GI No. 49065488) and can be encoded by the nucleic acid sequence set forth in GenBank® Accession No. NM_014175.3 (GI No. 169403971). A human Mrps23 polypeptide can have the amino acid sequence set forth in GenBank® Accession No. NP_057154.2 (GI No. 16554604) and can be encoded by the nucleic acid sequence set forth in GenBank® Accession No. NM_016070.3 (GI No. 312222785). A human Mrps2 polypeptide can have the amino acid sequence set forth in GenBank® Accession No. AAH04905.2 (GI No. 33872889) and can be encoded by the nucleic acid sequence set forth in GenBank® Accession No. NM_016034.4 (GI No. 389565494). A human Mrpl17 polypeptide can have the amino acid sequence set forth in GenBank® Accession No. CAG33458.1 (GI No. 48146471) and can be encoded by the nucleic acid sequence set forth in GenBank® Accession No. NM_022061.3 (GI No. 169403966). A human Prodh polypeptide can have the amino acid sequence set forth in GenBank® Accession No. AAD24775.1 (GI No. 4581877) and can be encoded by the nucleic acid sequence set forth in GenBank® Accession No. NM_016335.4 (GI No. 304766735). A human Slc25a1 polypeptide can have the amino acid sequence set forth in GenBank® Accession No. NP_005975.1 (GI No. 21389315) and can be encoded by the nucleic acid sequence set forth in GenBank® Accession No. NM_005984.3 (GI No. 374713106). A human Hmgcl polypeptide can have the amino acid sequence set forth in GenBank® Accession No. CAG33165.1 (GI No. 48145885) and can be encoded by the nucleic acid sequence set forth in GenBank® Accession No. NM_000191.2 (GI No. 62198231). A human Cps1 polypeptide can have the amino acid sequence set forth in GenBank® Accession No. AAH20695.1 (GI No. 116283350) and can be encoded by the nucleic acid sequence set forth in GenBank® Accession No. NM_001122633.2 (GI No. 327532712). A human Aldh4a1 polypeptide can have the amino acid sequence set forth in GenBank® Accession No. ACN89883.1 (GI No. 225421341) and can be encoded by the nucleic acid sequence set forth in GenBank® Accession No. FJ462711.1 (GI No. 225421340). A human Mdh2 polypeptide can have the amino acid sequence set forth in GenBank® Accession No. CAG38785.1 (GI No. 49168580) and can be encoded by the nucleic acid sequence set forth in GenBank® Accession No. CR536548.1 (GI No. 49168579). A human Atp5b polypeptide can have the amino acid sequence set forth in GenBank® Accession No. ABD77240.1 (GI No. 89574029) and can be encoded by the nucleic acid sequence set forth in GenBank® Accession No. NM_001686.3 (GI No. 50345985). A human Slc25a22 polypeptide can have the amino acid sequence set forth in GenBank® Accession No. NP_001177990.1 (GI No. 300796991) and can be encoded by the nucleic acid sequence set forth in GenBank® Accession No. NM_001191060.1 (GI No. 300796969). A human Slc25a19 polypeptide can have the amino acid sequence set forth in GenBank® Accession No. NP_001119594.1 (GI No. 186928860) and can be encoded by the nucleic acid sequence set forth in GenBank® Accession No. NM_001126121.1 (GI No. 186928857). A human Uqcrc2 polypeptide can have the amino acid sequence set forth in GenBank® Accession No. AAH00484.1 (GI No. 12653427)

and can be encoded by the nucleic acid sequence set forth in GenBank® Accession No. NM_003366.2 (GI No. 50592987). A human Abcf2 polypeptide can have the amino acid sequence set forth in GenBank® Accession No. NP_009120.1 (GI No. 27881506) and can be encoded by the nucleic acid sequence set forth in GenBank® Accession No. NM_007189.2 (GI No. 525345247). A human Acbd4 polypeptide can have the amino acid sequence set forth in GenBank® Accession No. AAH41143.1 (GI No. 26996542) and can be encoded by the nucleic acid sequence set forth in GenBank® Accession No. NM_001135704.1 (GI No. 209364588). A human Fads1 polypeptide can have the amino acid sequence set forth in GenBank® Accession No. AFL91689.1 (GI No. 390432195) and can be encoded by the nucleic acid sequence set forth in GenBank® Accession No. AK314199.1 (GI No. 164697148). A human Gnpat polypeptide can have the amino acid sequence set forth in GenBank® Accession No. NP_055051.1 (GI No. 7657134) and can be encoded by the nucleic acid sequence set forth in GenBank® Accession No. NM_014236.3 (GI No. 170650722). A human Lypla1 polypeptide can have the amino acid sequence set forth in GenBank® Accession No. CAG33384.1 (GI No. 48146323) and can be encoded by the nucleic acid sequence set forth in GenBank® Accession No. CR457103.1 (GI No. 48146322). A human Cpt2 polypeptide can have the amino acid sequence set forth in GenBank® Accession No. NP_000089.1 (GI No. 4503023) and can be encoded by the nucleic acid sequence set forth in GenBank® Accession No. NM_000098.2 (GI No. 169790951). A human Agpat4 polypeptide can have the amino acid sequence set forth in GenBank® Accession No. AAH13410.1 (GI No. 38196950) and can be encoded by the nucleic acid sequence set forth in GenBank® Accession No. XM_005267052.1 (GI No. 530383869). A human Acaca polypeptide can have the amino acid sequence set forth in GenBank® Accession No. AAH31485.1 (GI No. 32425437) and can be encoded by the nucleic acid sequence set forth in GenBank® Accession No. XM_005257266.1 (GI No. 530412017).

The potato polysaccharide preparations provided herein or nutritional supplement compositions provided herein can be administered to any appropriate mammal (e.g., rat, mouse, dog, cat, horse, cow, goat, pig, chicken, duck, rabbit, sheep, monkey, or human). In addition, any appropriate route of administration (e.g., oral or parenteral administration) can be used to administer a potato polysaccharide preparation provided herein or a nutritional supplement composition provided herein to a mammal. For example, a potato polysaccharide preparation provided herein or a nutritional supplement composition provided herein can be administered orally.

The document will provide addition description in the following examples, which do not limit the scope of the invention described in the claims.

EXAMPLES

Example 1

Identification of a Potato Polysaccharide Preparation Having the Ability to Alter Expression of Polypeptides Involved with Mitochondria Activity and Function 6 grams of a Russet potato variety of the *Solanum tuberosum* species were homogenized with a Polytron homogenizer in 20 mL water in a 50 mL centrifuge tube and kept at room temperature for 1 hour. The homogenate was centrifuged at 4000 rpm for 10 minutes. A Sep-Pak Plus C-18 cartridge was activated with 10 mL 100% acetonitrile (ACN) and washed with 10 mL 0.05% trifluoroacetic acid in water (TFA water). 10 mL of the supernatant was loaded onto the cartridge, and all H$_2$O that passes through cartridge was collected in 1.5 mL Eppendorf tubes. Next, 10 mL of 2% ACN (in 0.05% TFA water) was passed through the column, and the elutriate was collected in 1.5 mL Eppendorf tubes. Next, 10 mL of 5% ACN (in 0.05% TFA water) was used to wash the column, and the elutriate was collected in 1.5 mL Eppendorf tubes. Finally, 10 mL of 10% ACN (in 0.05% TFA water) was collected in 1.5 mL Eppendorf tubes after passing through the column. All of the fractions were dried, and the dried fractions of the same ACN concentration were reconstituted into 1 tube in 1 mL of 0.05% TFA water for further purification via HPLC or reconstituted in 1 mL of phosphate buffered saline for use in cell treatments.

Figure 2:
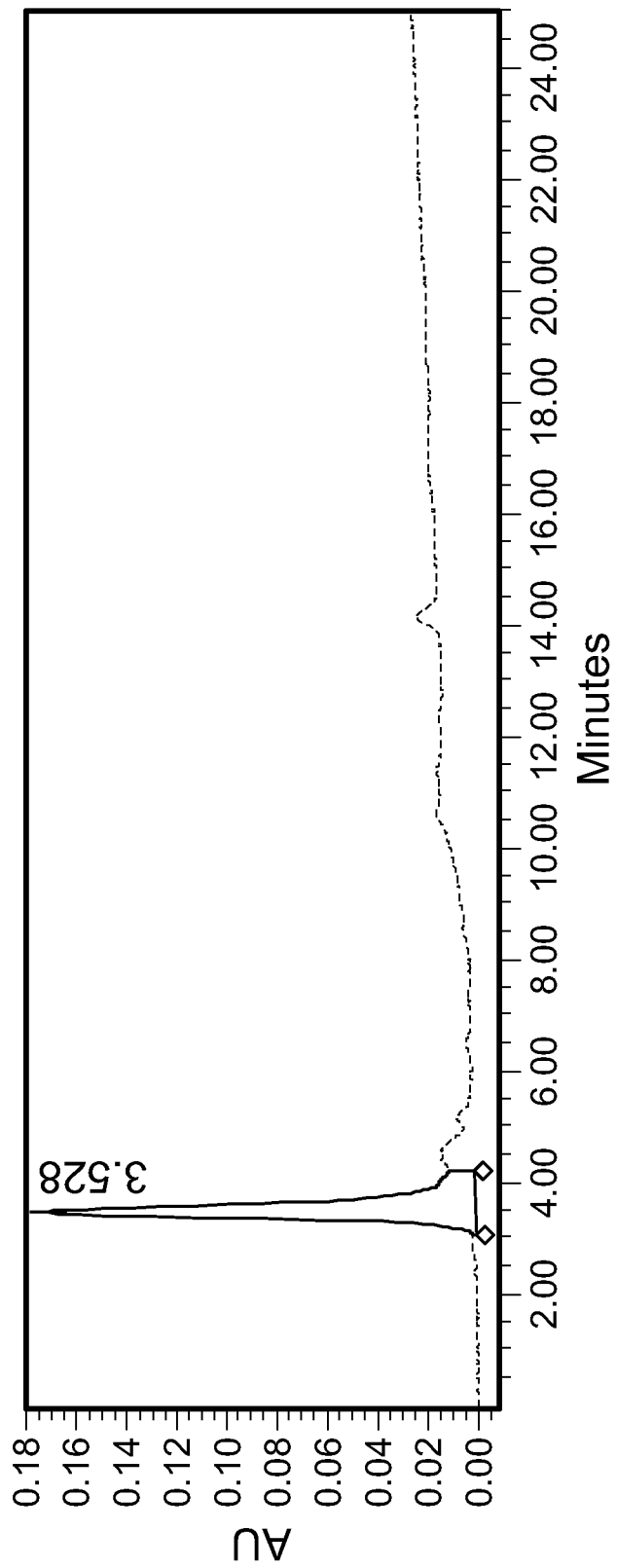
FIG. 2 is an HPLC chromatogram of collected and re-purified 3.5 minute peak material from a 10% ACN extract of raw potato shown in FIG. 1.

A Waters 2695 separations module with a photodiode array detector was used to purify the 10% ACN extract. An XterraRP C18 column (4.6×150 mm) was used for the separation with 0.05% TFA water as the mobile phase. Each HPLC run was a 20 minute gradient ranging from 0 to 2.5% ACN. The injection volume was 100 µL, and the flow rate was 0.5 mL/minute. HPLC fractionation of the 10% ACN extract yielded three major UV absorbing peaks eluted at 3.5, 3.9, and 12.1 minutes (FIG. 1). Collection and HPLC re-purification of the 3.5 minute fraction yielded a symmetrical peak displaying a maximum absorbance at 198.3 nm (FIG. 2).

The three peaks were evaluated to determine whether or not they obtained material having the ability to alter the expression levels of polypeptides involved in mitochondria activity and function. Briefly, 5×10$^5$ neuroblastoma cells obtained from American Type Culture Collection (ATCC) were plated into each well of 6-well plates with 2 mL of RPMI media and incubated for 4 hours in the presence or absence of different aliquots of the HPLC purified material. Following the incubation, total RNA was isolated and purified using the RNeasy mini kit (Qiagen, Valencia, Calif.). In particular, pelleted cells were resuspended in 600 µL of RLT lysis buffer (Qiagen) and homogenized by passing the lysate 20 times through a 1 mL pipette tip. The samples were then processed according to the manufacturer's instructions (Qiagen, Valencia, Ca). In the final step, the RNA was eluted with 40 µL of RNase-free water by centrifugation for 1 minute at 13,000 g. The RNA was analyzed on a model 2100 bioanalyzer (Agilent, Santa Clara, Calif.) using a total RNA nanochip according to the manufacturer's protocol. Afterwards, 2 µg of total RNA was reverse transcribed using Superscript III reverse transcriptase and random primers.

DNA microarray analyses also were performed using a system provided by Agilent. Arrays included four arrays per chip (Agilent 4X44K chips). Total RNA was reverse transcribed (400 ng) using T7 primers and labeled and transcribed using Cyanine-3 dye. Each array was hybridized with at least 1.65 µg of labeled cRNA at 65° C. for 18 hours. Arrays were scanned using an Agilent array scanner. A 10% or greater change in gene expression was capable of being determined using both microarray platforms.

Incubation of cultured cells with the HPLC purified fraction eluted at 3.5 minutes produced changes in the expression of mitochondrial and cellular metabolic genes (Table 1). The extracted potato material that eluted at 3.5 minutes is referred to herein as potato polysaccharide material, a potato polysaccharide preparation, or a potato polysaccharide since it was determined to be a polysaccharide as indicated below. The 3.5 minute fraction (a potato polysaccharide preparation) was the only fraction of the three determined to possess significant biological activity when tested using real time PCR for TFAM, NFKB, and HMGCR expression.

TABLE 1

Gene expression changes in HTB-11 cells as determined by microarray following a four-hour incubation with a potato polysaccharide preparation.

| Gene symbol | Gene name | % change |
| --- | --- | --- |
| TFAM | transcription factor A, mitochondrial | +15 |
| FOX01A | forkhead box O1 | −28 |
| NFKB1 | nuclear factor of kappa light polypeptide gene enhancer in B-cells 1 | −14 |
| ATP5A1 | ATP synthase, H+ transporting, mitochondrial F1 complex, alpha subunit 1 | +30 |
| PDHA1 | pyruvate dehydrogenase (lipoamide) alpha 1 | +8 |
| PDHA2 | pyruvate dehydrogenase (lipoamide) alpha 2 | +41 |
| PDK2 | pyruvate dehydrogenase kinase, isozyme 2 | −24 |
| PDK4 | pyruvate dehydrogenase kinase, isozyme 4 | −41 |
| HMGCR | 3-hydroxy-3-methylglutaryl-CoA reductase | −18 |
| THOP1 | thimet oligopeptidase 1 | +23 |

Figure 3:
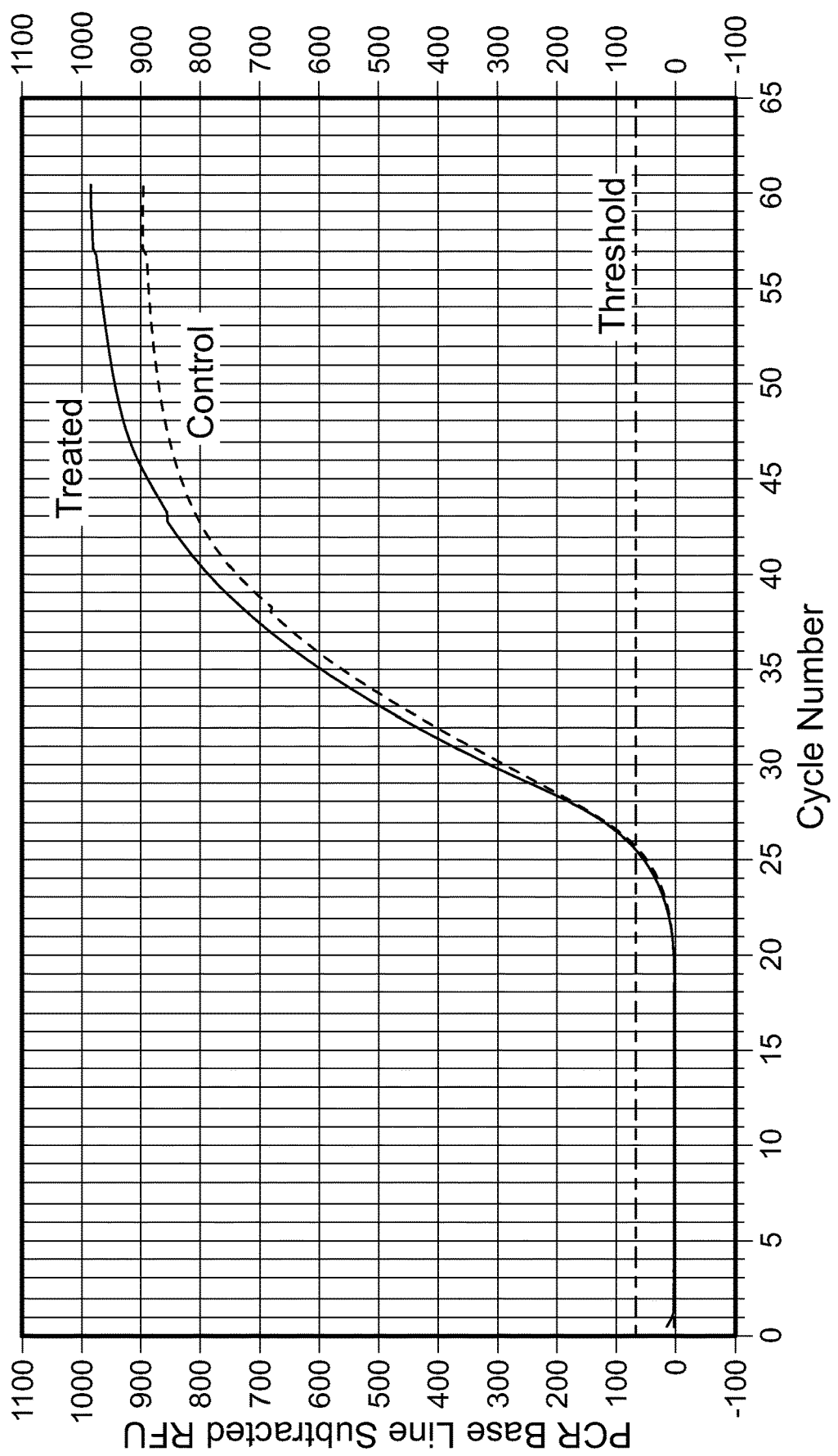
FIG. 3 is a representative real time PCR amplification plot for TFAM expression.

Real-time PCR was performed in triplicate with TFAM, HMGCR, and NFKB1 detector sets. Beta-actin or GAPDH was used as a reference gene. The real-time PCR master mix included 25 μL 2× universal master mix, 2.5 μL 20× detector set (with the primer and probe), and 21.5 μL of water. PCR was performed in an Applied Biosystems 7500 sequence detection system. The thermocycler conditions included denaturation at 95° C. for 15 seconds and annealing/extension at 60° C. for 60 seconds. Forty cycles of PCR were preceded by 95° C. for 10 minutes. Reactions were performed in triplicate. The relative quantities of TFAM were found using the formula $2^{-\Delta\Delta Ct}$ using the Applied Biosystems 7500 software. Validation of some of the microarray results by real time PCR used TFAM, HMGCR, and NFKB1 as candidate genes. A representative real time PCR amplification plot demonstrated that TFAM mRNA was present and was differentially expressed (FIG. 3). The potato polysaccharide preparation had a profound effect on TFAM expression and was able to upregulate it by 57% (Table 2). Both HMGCR and NFKB1 gene expression were reduced by approximately 20%, consistent with and validating the DNA microarray data (Table 2).

TABLE 2

Validation of gene expression changes by real time PCR. HTB-11 cells treated for 4 hours with a potato polysaccharide preparation.

| Gene Symbol | % change |
| --- | --- |
| TFAM | +57 ± 9 |
| NFKB1 | −20 ± 5 |
| HMGCR | −19 ± 4 |

Figure 4:
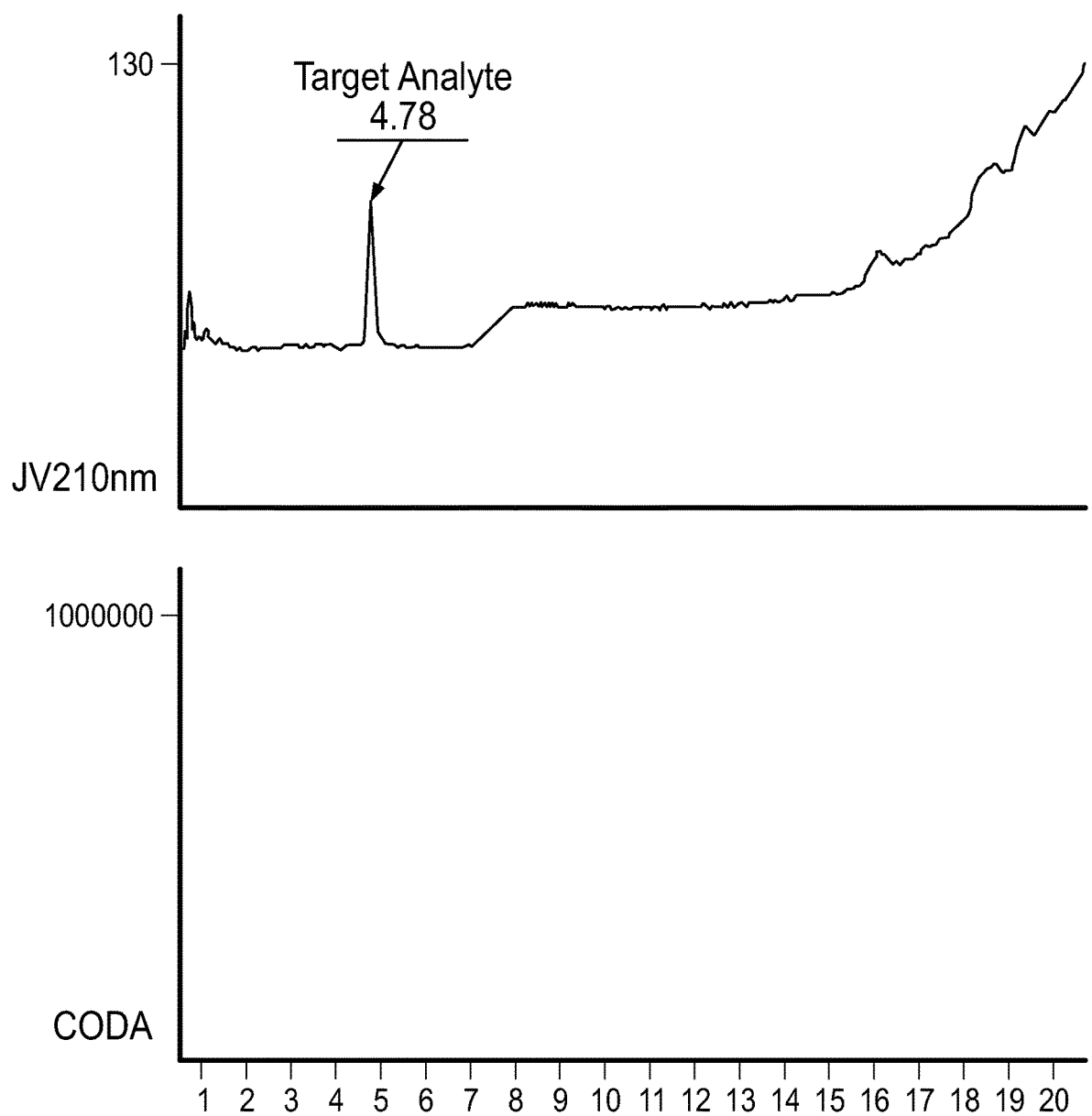
FIG. 4 is an LC/MS trace of 3.5 minute HPLC peak material.
Figure 5:
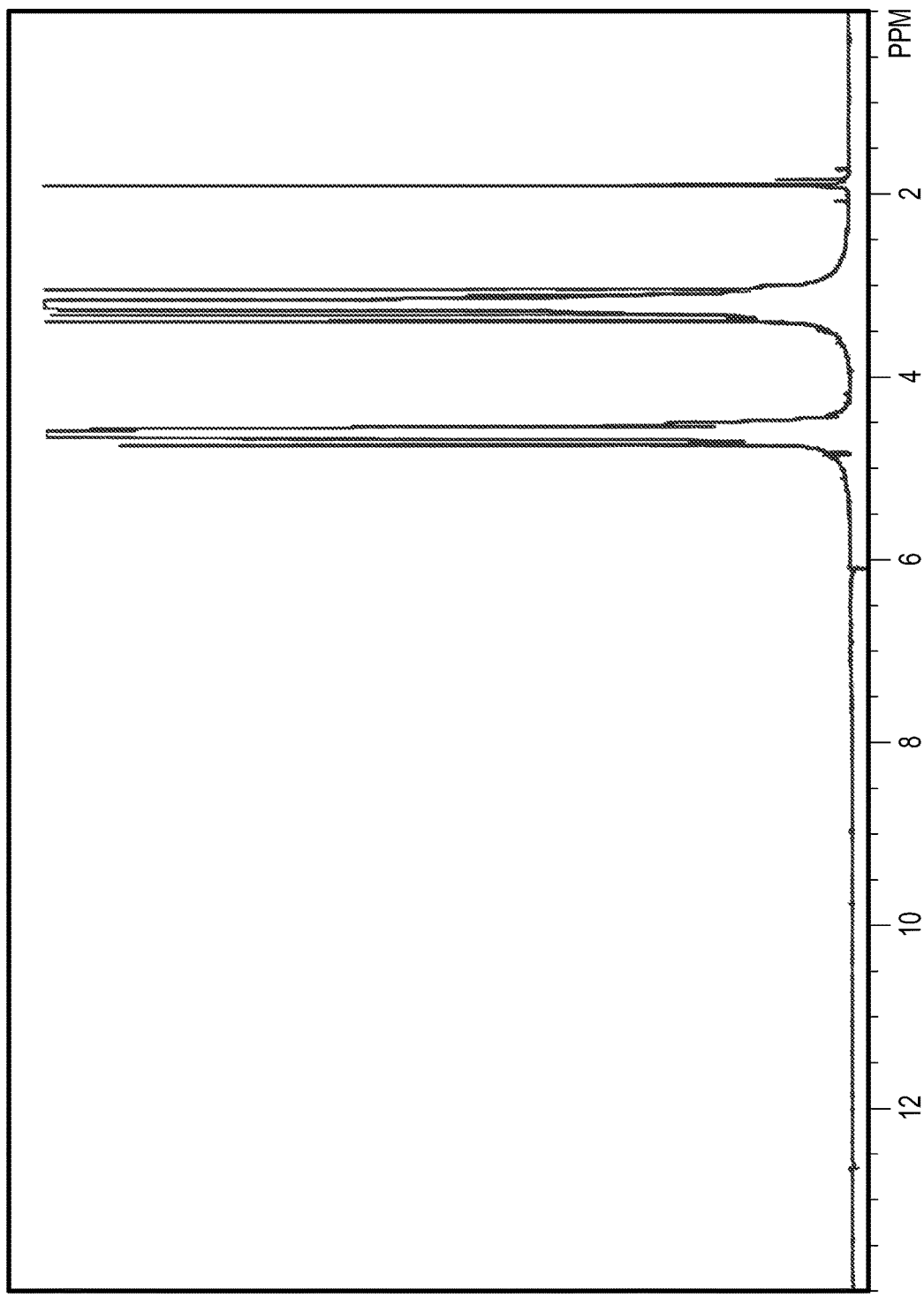
FIG. 5 is a full NMR spectrum of 3.5 minute HPLC peak material.
Figure 6:
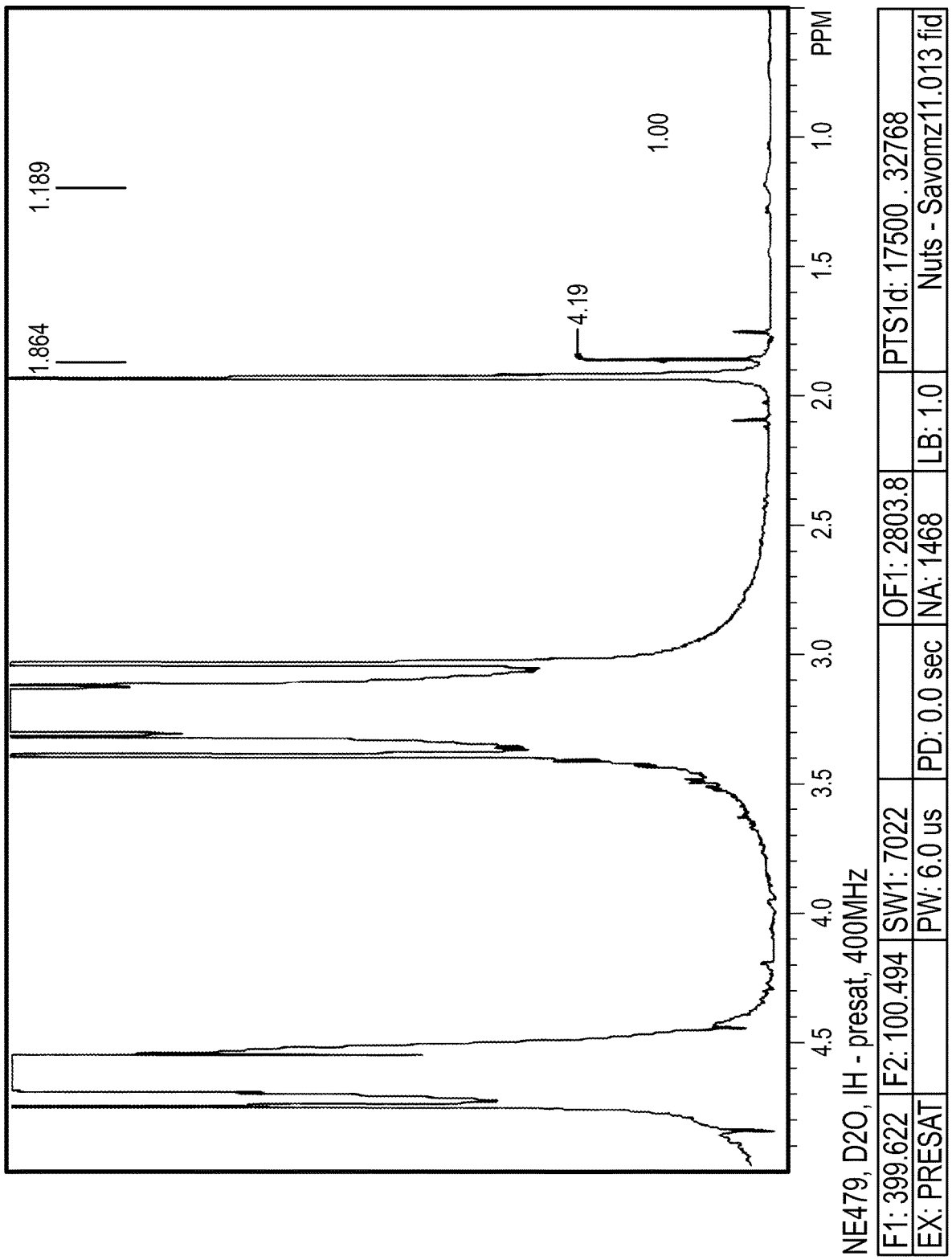
FIG. 6 is an expanded NMR spectrum of 3.5 minute HPLC peak material.

Further chemical characterization of the symmetrical 3.5 minute HPLC peak material was performed. Pooled 3.5 minute HPLC fractions were dried and reconstituted in 1 mL TFA water and subjected to tandem LC/MS/MS (FIG. 4) and NMR chemical analyses (FIGS. 5 and 6). For the NMR analysis, $^1$H-NMR was run on the sample using deuterium oxide (D20) as a solvent to further analyze the sample. The water peak at 4.65 PPM was solvent-suppressed, and the spectrum was acquired for several hours. Acetamide was detected at 3.2 PPM, along with acetonitrile at 1.9 PPM. Minor peaks were detected at 1.05 PPM, 1.17 PPM (broad peak), 1.189 PPM, and 1.864 PPM. One characteristic of polymeric materials in a proton NMR was the broadening of peaks such as the shift at 1.17 PPM. These shifts on the NMR could represent the peak at 4.8 PPM and suggested a polar, water-soluble polymer such as a polysaccharide. Taken together, these results confirmed the presence of high molecular weight polysaccharide material contained in HPLC purified fractions eluting at 3.5 minutes.

Further analysis confirmed that the HPLC purified fraction eluting at 3.5 minutes contains polysaccharide material (e.g., highly substituted complex xyloglucan material). To make the polysaccharide material analyzable by gas chromatography/mass spectroscopy (GC/MS), it was converted into its derivatized carbohydrate fragments. Briefly, the sample was concentrated to a dry residue that was hydrolyzed using trifluoroacetic acid. This was then reduced using sodium borohydride, and after borate removal, the end product was acylated using acetic anhydride and pyridine. The end products of the reaction were injected directly on GC/MS to identify any acylated carbohydrates. Based on the end analysis, a larger carbohydrate existed in the sample. The total ion chromatogram (TIC) is shown below in FIG. 7 with appropriate peak labels below in Table 3. The major components identified are indicated in bold (peaks 3, 12, 14, and 21). The corresponding fragmentation for each compound is provided in FIGS. 8-27. For each fragmentation, the peak fragmentation pattern is on the top, the compound library fragmentation match is on the bottom, and an overlay of the two is in the center. Finally, unlabeled peaks were either column bleed or did not have a sufficient match to the compound library.

TABLE 3

Summary of GC/MS results.

| Peak | Retention Time (min) | Compound Name | Structure |
| --- | --- | --- | --- |
| 1 | 10.731 | Diacetamide | (structure) |
| 2 | 13.669 | 3-Acetoxy pyridine | (structure) |

TABLE 3-continued

Summary of GC/MS results.

| Peak | Retention Time (min) | Compound Name | Structure |
|---|---|---|---|
| 3 | 19.568 | 3,4-Furan dimethanol, diacetate | 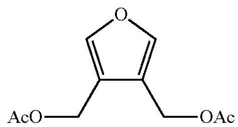 [SMILES: CC(=O)OCc1cocc1COC(C)=O] |
| 4 | 19.950 | 1,2,3-propanetriol diacetate | 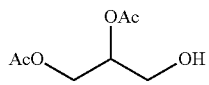 [SMILES: CC(=O)OCC(CO)OC(C)=O] |
| 5 | 23.387 | Imidazole, 2-acetamino-5-methyl | 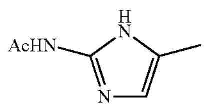 |
| 6 | 23.499 | 6,7-dihydro-5H-pyrrol[2,1-c][1,2,4]triazole-3-carboxylic acid | 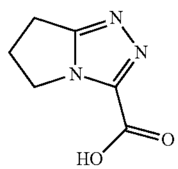 [SMILES: O=C(O)c1nnc2n1CCC2] |
| 7 | 24.304 | Acetic acid, 1-(2-methyltetrazol-5-yl) ethenyl ester | 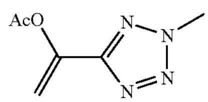 |
| 8 | 25.538 | 1,2,3,4-butanetriol, tetraacetate | 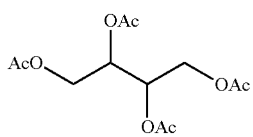 [SMILES: CC(=O)OCC(OC(C)=O)C(COC(C)=O)OC(C)=O] |
| 9 | 27.412 | (1,5)β(1,3)triacetyl D-galactosan (stereoisomer 1) | 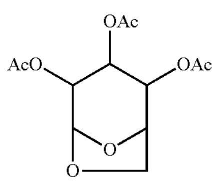 [SMILES: CC(=O)OC1C2COC(O2)C(OC(C)=O)C1OC(C)=O] |
| 10 | 28.188 | (1,5)β(1,3)triacetyl D-galactosan (stereoisomer 2) | 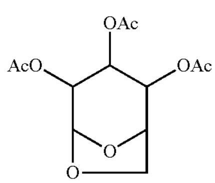 [SMILES: CC(=O)OC1C2COC(O2)C(OC(C)=O)C1OC(C)=O] |
| 11 | 29.210 | Pentaerythritol tetraacetate | 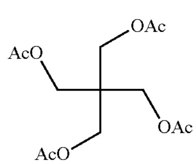 |
| 12 | 29.727 | 1,2,3,4,5-penta-o-acetyl-D-xylitol (isomer 1) | 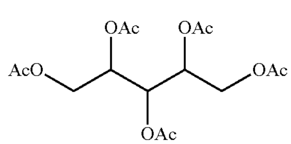 [SMILES: CC(=O)OCC(OC(C)=O)C(OC(C)=O)C(COC(C)=O)OC(C)=O] |

TABLE 3-continued

Summary of GC/MS results.

| Peak | Retention Time (min) | Compound Name | Structure |
|---|---|---|---|
| 13 | 30.697 | 1,2,345-penta-o-acetyl-D-xylitol (isomer 2) | 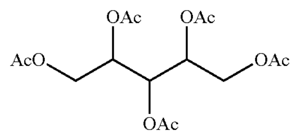 [SMILES: CC(=O)OCC(OC(C)=O)C(OC(C)=O)C(COC(C)=O)OC(C)=O] |
| 14 | 32.477 | 3,5-diacetoxy-benzyl alcohol | 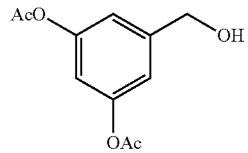 [SMILES: CC(=O)Oc1cc(CO)cc(OC(C)=O)c1] |
| 15 | 32.677 | β-D-glucopyranose, pentaacetate | 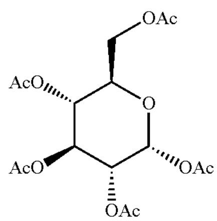 [SMILES: CC(=O)OC[C@H]1O[C@H](OC(C)=O)[C@H](OC(C)=O)[C@@H](OC(C)=O)[C@@H]1OC(C)=O] |
| 16 | 33.012 | D-mannitol hexaacetate | 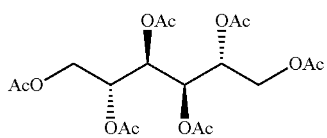 [SMILES: CC(=O)OC[C@@H](OC(C)=O)[C@@H](OC(C)=O)[C@H](OC(C)=O)[C@@H](COC(C)=O)OC(C)=O] |
| 17 | 33.106 | β-D-galactopyranose, pentaacetate | 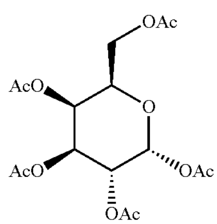 [SMILES: CC(=O)OC[C@H]1O[C@H](OC(C)=O)[C@H](OC(C)=O)[C@@H](OC(C)=O)[C@H]1OC(C)=O] |
| 18 | 33.206 | Galacticol, hexaacetate | 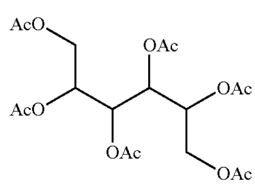 [SMILES: CC(=O)OCC(OC(C)=O)C(OC(C)=O)C(OC(C)=O)C(COC(C)=O)OC(C)=O] |
| 19 | 33.364 | Cyclohexane carboxylic acid, 1,2,45-tetrakis(acetoxy), (1α,3α,4α,5β)-(−) | 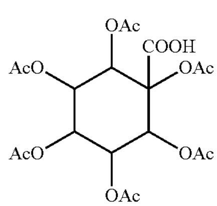 [SMILES: CC(=O)OC1C(OC(C)=O)C(OC(C)=O)C(OC(C)=O)(C(=O)O)C(OC(C)=O)C1OC(C)=O] |
| 20 | 33.582 | Muco-inositol, hexaacetate | 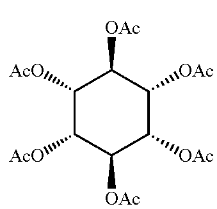 [SMILES: CC(=O)O[C@H]1[C@H](OC(C)=O)[C@@H](OC(C)=O)[C@@H](OC(C)=O)[C@H](OC(C)=O)[C@H]1OC(C)=O] |

TABLE 3-continued

Summary of GC/MS results.

| Peak | Retention Time (min) | Compound Name | Structure |
|---|---|---|---|
| 21 | 33.006 | D-glucitol-hexaacetate | (structure shown) |
| 22 | 34.463 | Myo-inositol, hexaacetate | (structure shown) |

These results demonstrate the presence of sugar monomers that serve as building blocks for a larger carbohydrate. It appeared from these multiple lines of analysis that the potato polysaccharide preparation is a highly substituted complex xyloglucan.

Example 2

Sweet Potatoes and Multiple Varieties of Potatoes Exhibit the Presence of Potato Polysaccharide Material Six grams of potato material from multiple varieties of *Solanum tuberosum* (Organic yellow, Purple, Idaho Russet, and Yukon Gold) and six grams of material from sweet potatoes (*Ipomoea batatas*) were extracted in 20 mL of water. 10 mL of that water was then loaded onto a sep-pak cartridge, and the cartridge was then eluted with 10 mL of 10% ACN. The ACN was then dried, and the residue was dissolved in 1 mL of water. A 100 µL injection of this water was assessed using HPLC.

The HPLC chromatograms demonstrated that the amount of the first peak (at 3.5 minutes at 210 nm) was the same for all five types of potatoes tested (FIGS. 28-32).

Figure 33:
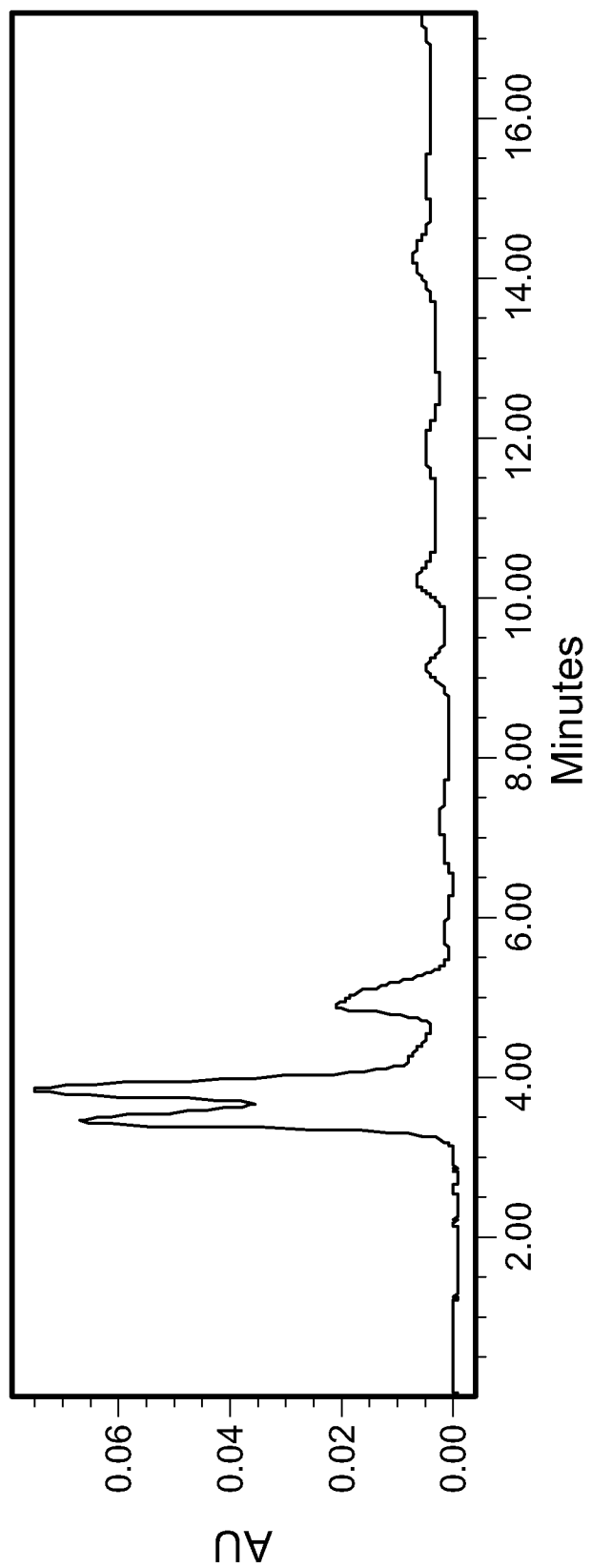
FIG. 33 is an HPLC chromatogram of a 10% ACN extract of boiled Purple potato.

In another experiment, material was extracted from a boiled Purple potato and analyzed. The peak at 3.5 minutes was not reduced in the boiled potato (FIG. 33).

Figure 34:
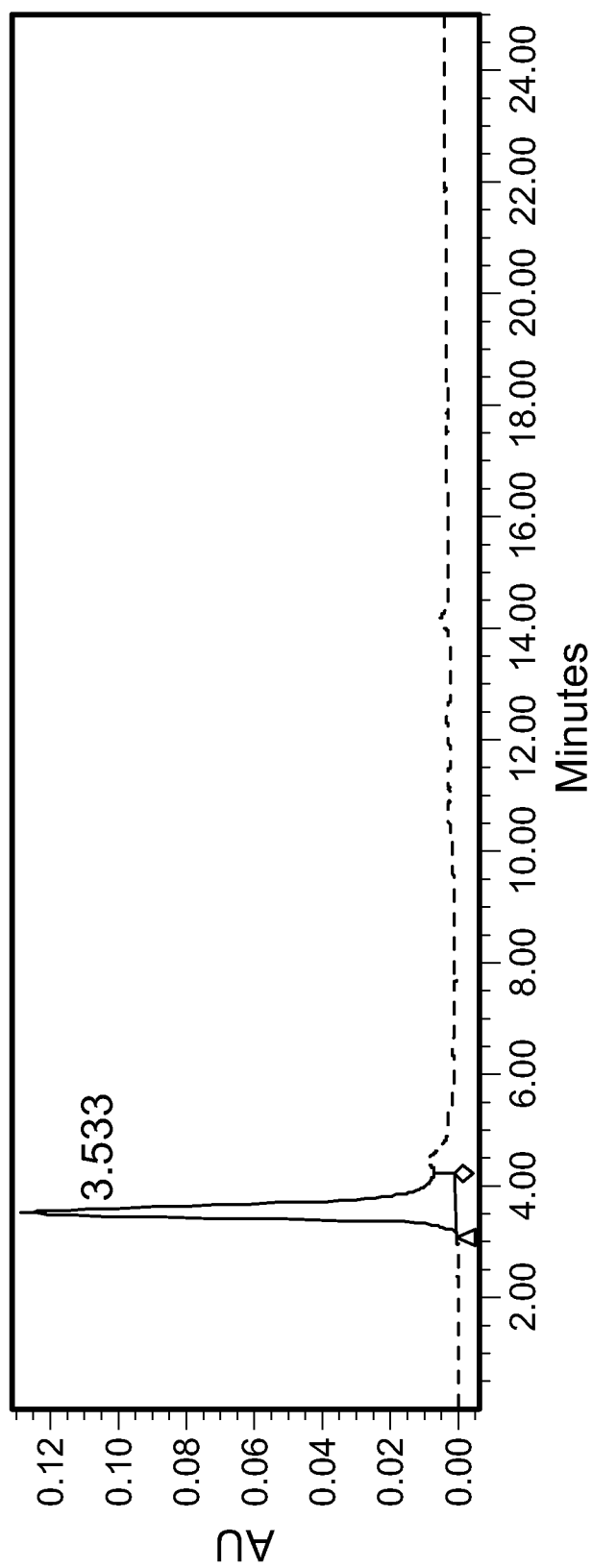
FIG. 34 is an HPLC chromatogram of two pooled fraction collections from Idaho Russet potatoes.

The 3.5 minute peak from two pooled fraction collections from Idaho Russet potatoes was collected, dried, and reconstituted in 100 µL of water. The material was then injected into the HPLC yielding a single peak at 3.5 minutes (FIG. 34). Taken together, these results demonstrate that potatoes within the *Solanum tuberosum* and *Ipomoea batatas* species contain potato polysaccharide material.

Example 3

Highly Substituted Complex Xyloglucan from Potato Material Alters Expression of Polypeptides in Human Omental Apidocytes Obtained from Diabetic Patients Human omental apidocytes obtained from normal and diabetic patients were purchased from Zen-Bio, Inc (Research Triangle Park, N.C.). The cells were either untreated or treated with 62.5 µg/mL of the 3.5 minute peak from purple potatoes for four hours. After the four hour incubations, the cells were harvested, and a microarray analysis was performed to measure changes in gene expression.

Incubation of human omental apidocytes from diabetic patients with the HPLC purified fraction eluted at 3.5 minutes produced changes in the expression of genes involved in obesity and/or diabetes (Table 4). Incubation of human omental apidocytes from normal humans produced minimal changes in the expression of the genes listed in Table 4 (Table 5).

TABLE 4

Gene expression changes as determined by microarray following a four-hour incubation of human omental apidocytes from diabetic patients with a potato polysaccharide preparation.

| Gene symbol | % change |
|---|---|
| AGPAT1 | −1 |
| OLR1 | −45 |
| BCAT2 | −9 |
| NFKB1 | −6 |
| SH2B1 | −17 |
| LPL | −24 |
| HMGCR | −9 |
| LIPE | +15 |
| PCK2 | +5 |
| MOGAT1 | +52 |
| PPARGC1a | +59 |
| PPARGC1b | +44 |
| SOD2 | +18 |
| NR4A1 | +12 |
| ACAT2 | +13 |

TABLE 5

Gene expression changes as determined by microarray following a four-hour incubation of human omental apidocytes from normal humans with a potato polysaccharide preparation.

| Gene symbol | % change |
|---|---|
| AGPAT1 | None detected |
| OLR1 | −18 |
| BCAT2 | None detected |
| NFKB1 | −56 |
| SH2B1 | −33 |
| LPL | +18 |

TABLE 5-continued

Gene expression changes as determined by microarray following a four-hour incubation of human omental apidocytes from normal humans with a potato polysaccharide preparation.

| Gene symbol | % change |
|---|---|
| HMGCR | +16 |
| LIPE | +32 |
| PCK2 | +30 |
| MOGAT1 | +22 |
| PPARGC1a | +26 |
| PPARGC1b | +26 |
| SOD2 | +23 |
| NR4A1 | +45 |
| ACAT2 | +17 |

Real-time PCR was performed in triplicate with AGPAT1, OLR1, BCAT2, NR4A1, and ACAT2 detector sets. Beta-actin or GAPDH was used as a reference gene. The real-time PCR master mix included 25 µL 2× universal master mix, 2.5 µL 20× detector set (with the primer and probe), and 21.5 µL of water. PCR was performed in an Applied Biosystems 7500 sequence detection system. The thermocycler conditions included denaturation at 95° C. for 15 seconds and annealing/extension at 60° C. for 60 seconds. Forty cycles of PCR were preceded by 95° C. for 10 minutes. Reactions were performed in triplicate. Validation of some of the microarray results by real time PCR used AGPAT1, OLR1, BCAT2, NR4A1, and ACAT2 as candidate genes. Real time PCR amplification plots demonstrated that AGPAT1, OLR1, BCAT2, NR4A1, and ACAT2 mRNAs were present and were differentially expressed (Table 6).

TABLE 6

Validation of gene expression changes by real time PCR. Human omental apidocytes from diabetic patients treated for 4 hours with a potato polysaccharide preparation.

| Gene Symbol | % change |
|---|---|
| AGPAT1 | −13 ± 1 |
| OLR1 | −9 ± 1 |
| BCAT2 | −4 ± 1 |
| NR4A1 | +34 ± 3 |
| ACAT2 | +12 ± 2 |

Example 4

Highly Substituted Complex Xyloglucan from Potato Material Alters Expression of Polypeptides in Mouse Myocytes Mouse myoblasts were seeded in 2 mL aliquots into two 75 cm$^2$ tissue culture flasks. Cells were left to differentiate into myocytes for 4 days in 5% $CO_2$ at 37° C.

Myocytes were detached from flask walls using gentle agitation. Suspended cells were transferred to a 15 mL conical tube and centrifuged at 500 g for 3 minutes. 2 mL aliquots were seeded into 75 cm$^2$ tissue culture flasks for both control and diabetic model cells. The mouse cells were obtained from normal mice and from mice treated with low dose alloxan. The diabetic mice had high blood glucose compared to the normal mice. A potato polysaccharide preparation (62.5 µg/mL of the 3.5 minute peak from purple potatoes) was added to one control and one diabetic flask, and the cells were incubated for 24 hours.

After the 24 hour incubation, the cells were harvested, and a microarray analysis was performed to measure changes in gene expression. In addition, images were taken of the cells after treatment using a Nikon EclipseTE300 (Morell) inverted microscope coupled with an Optronics digital cameraware at 20×. The images were analyzed on ImageJ software for cell mortality and fiber size. Cell mortality was calculated using a ratio of the number of inactive cells to the number of active cells. Fiber size was calculated using a polygonal lasso tracer and measured in pixel area.

Incubation of mouse myocytes from the diabetic model with the HPLC purified fraction eluted at 3.5 minutes produced changes in the expression of genes involved in obesity and/or diabetes (Table 7). Incubation of mouse myocytes from normal mice produced minimal changes in the expression of the genes listed in Table 7 (Table 8).

TABLE 7

Gene expression changes as determined by microarray following a 24-hour incubation of mouse myocytes from the diabetic model with a potato polysaccharide preparation.

| Gene symbol | % change |
|---|---|
| NFKB1 | −46 |
| SH2B1 | −35 |
| LPL | −16 |
| HMGCR | +25 |
| LIPE | −46 |
| PCK2 | none |
| SOD2 | +74 |
| NR4A1 | −33 |
| ACAT2 | none |
| PTEN | −22 |
| CASP8 | not detected |

TABLE 8

Gene expression changes as determined by microarray following a 24-hour incubation of mouse myocytes from normal mice with a potato polysaccharide preparation.

| Gene symbol | % change |
|---|---|
| NFKB1 | 37 |
| SH2B1 | 202 |
| LPL | 139 |
| HMGCR | 105 |
| LIPE | 147 |
| PCK2 | 118 |
| SOD2 | None detected |
| NR4A1 | 200 |
| ACAT2 | 75 |
| PTEN | 96 |
| CASP8 | 104 |

Real-time PCR was performed in triplicate with PTEN and CASP8 detector sets. Beta-actin or GAPDH was used as a reference gene. The real-time PCR master mix included 25 µL 2× universal master mix, 2.5 µL 20× detector set (with the primer and probe), and 21.5 µL of water. PCR was performed in an Applied Biosystems 7500 sequence detection system. The thermocycler conditions included denaturation at 95° C. for 15 seconds and annealing/extension at 60° C. for 60 seconds. Forty cycles of PCR were preceded by 95° C. for 10 minutes. Reactions were performed in triplicate. Validation of some of the microarray results by real time PCR used PTEN and CASP8 as candidate genes. Real time PCR amplification plots demonstrated that PTEN and CASP8 mRNAs were present and were differentially expressed (Table 9).

TABLE 9

Validation of gene expression changes by real time PCR. Mouse myocytes from the diabetic model treated for 24 hours with a potato polysaccharide preparation.

| Gene Symbol | % change |
| --- | --- |
| PTEN | −31 ± 4 |
| CASP8 | −72 ± 8 |

Example 5

Analysis of a Potato Polysaccharide Preparation

Figure 35:
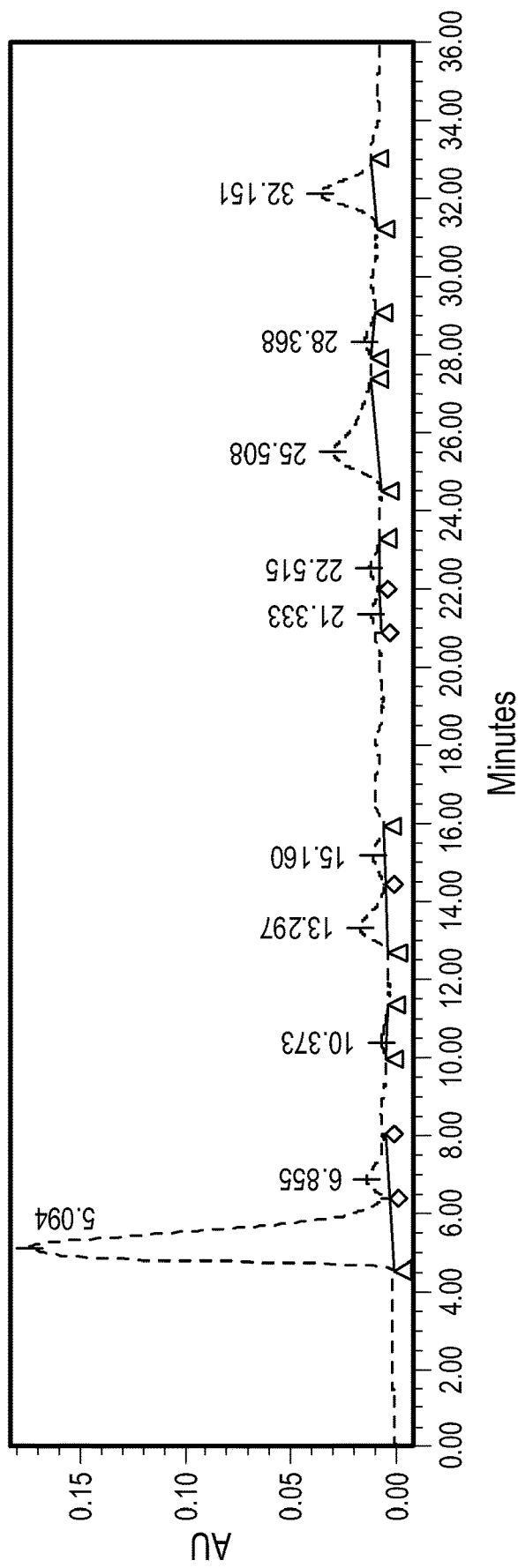
FIG. 35 is an HPLC chromatogram of fractions collections from 3 g of purple potatoes.
Figure 36:
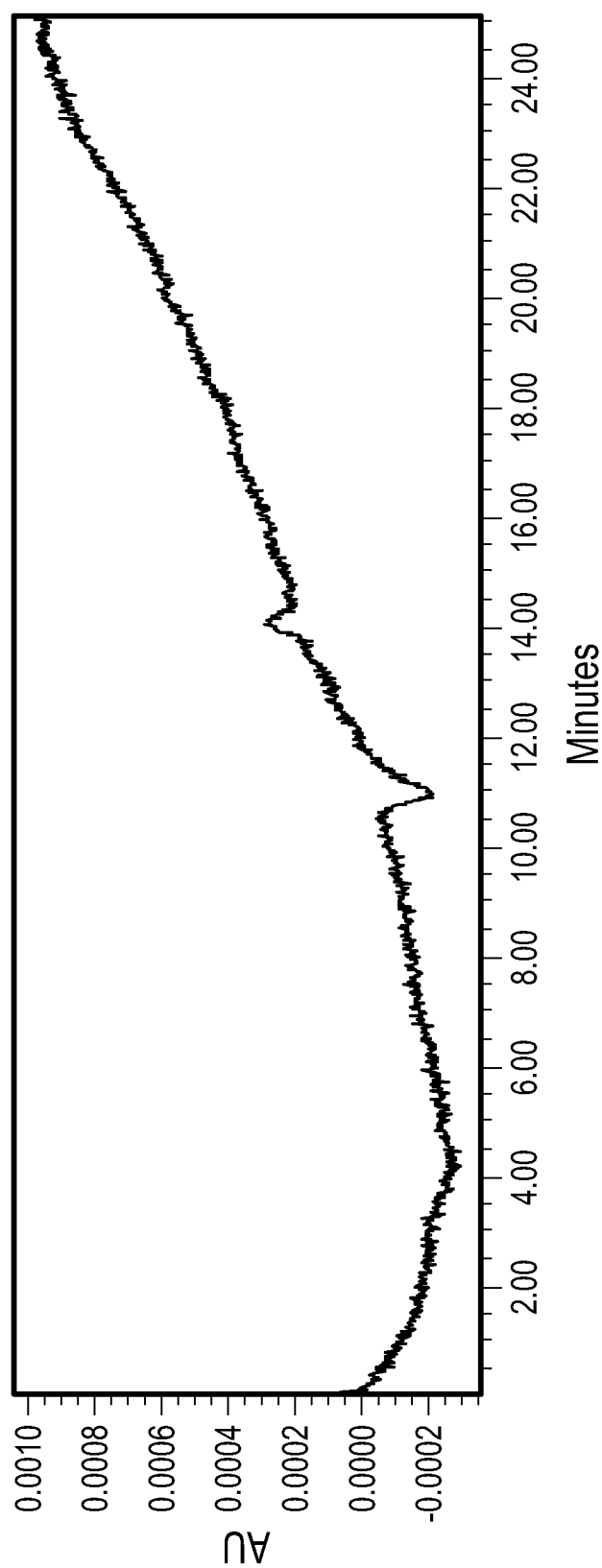
FIG. 36 is an HPLC chromatogram of media collected from cells exposed to a potato polysaccharide preparation for 4 hours.

A potato polysaccharide preparation was purified using HPLC from 3 g of purple potato. The potato polysaccharide peak was eluted at about 5 minutes (FIG. 35). This peak was obtained using a different chromatographic column (10 mm×150 mm) as compared to the column used to obtain the 3.5 minute peak. Since the column was a larger preparative column and the flow rate was 1.5 mL/minute, the elution time of the potato polysaccharide was 5 minutes.

The obtained peak was collected, dried, and reconstituted in 60 µL of water. The reconstituted potato polysaccharide material was then added to HTB-11 cells in culture flasks for 4 hours. The post treatment media was collected and added to another flask of HTB-11 cells. Each group of cells was analyzed for gene expression changes. The initially treated cells exhibited the expected changes in mitochondrial gene expression. No changes were detected in the cells exposed to the post treatment media for 4 hours.

In a separate experiment, the post treatment media was extracted using the techniques used to originally purify the potato polysaccharide. A chromatogram of the extracted post treatment media demonstrated the absence of a peak at 5 minutes.

Example 6

Using a Potato Polysaccharide Preparation to Treat Obesity

Class I-III obese humans are identified based on the criteria of Table 10.

TABLE 10

Classification of Overweight and Obesity by BMI, Waist Circumference, and Associated Disease Risks.

| | | | Disease Risk* Relative to Normal Weight and Waist Circumference | |
| --- | --- | --- | --- | --- |
| | BMI (kg/m$^2$) | Obesity Class | Men 102 cm (40 in) or less Women 88 cm (35 in) or less | Men > 102 cm (40 in) Women > 88 cm (35 in) |
| Underweight | <18.5 | | — | — |
| Normal | 18.5-24.9 | | — | — |
| Overweight | 25.0-29.9 | | Increased | High |
| Obesity | 30.0-34.9 | I | High | Very High |
| | 35.0-39.9 | II | Very High | Very High |
| Extreme Obesity | 40.0+ | III | Extremely High | Extremely High |

Once identified, a Class I-III obese patient is treated as follows. Potato polysaccharide is formulated in the presence of alpha lipoic acid or alpha tocopherol or both. Formulated potato polysaccharide is added to 90% by weight inert binder material and is administered by the oral parenteral route in the form of a tablet, capsule, or liquid, twice daily (bid). Maximal concentrations of potato polysaccharide are initially administered bid over the course of one month. Positive outcome measures include: (1) significant reduction of BMI, (2) augmentation of serum LDL/HDL ratio, (3) lowering serum triglyceride concentration, (4) lowering systolic and diastolic blood pressure, and (5) lowering fasting blood glucose.

Example 7

Using a Potato Polysaccharide Preparation to Treat Type II Diabetes

Once a type II diabetes patient is identified, the patient is treated as follows. Potato polysaccharide is formulated in the presence of alpha lipoic acid or alpha tocopherol or both. Formulated potato polysaccharide is added to 90% by weight inert binder material and is administered by the oral parenteral route in the form of a tablet, capsule, or liquid, twice daily (bid). Maximal concentrations of potato polysaccharide are initially administered bid over the course of one month. Positive outcome measures include: (1) restoration of normal fasting blood glucose, (2) significant weight loss and lowering of BMI, (3) augmentation of serum LDL/HDL ratio, (4) lowering serum triglyceride concentration, (5) lowering serum concentration of free fatty acids, (6) lowering systolic and diastolic blood pressure, (7) enhancement of insulin sensitivity, and (8) lowering insulin requirement in Type II diabetes patients.

Example 8

Using a Potato Polysaccharide Preparation to Treat a Polycystic Ovary Syndrome

Once a polycystic ovary syndrome (POS) patient is identified, the patient is treated as follows. Potato polysaccharide is formulated in the presence of alpha lipoic acid or alpha tocopherol or both. Formulated potato polysaccharide is added to 90% by weight inert binder material and is administered by the oral parenteral route in the form of a tablet, capsule, or liquid, twice daily (bid). Maximal concentrations of potato polysaccharide are initially administered bid over the course of one month. Positive outcome measures include: (1) restoration of normal reproductive function, (2) restoration of normal ovarian follicle maturation, (3) restoration of normal fasting blood glucose levels, (4) significant weight loss and lowering of BMI, (5) augmentation of serum LDL/HDL ratio, (6) lowering serum triglyceride concentration, (7) lowering serum concentration of free fatty acids, (8) lowering systolic and diastolic blood pressure, (9) enhancement of insulin sensitivity, and (10) lowering insulin requirement in comorbid POS patients with type II diabetes.

Example 9

Maintaining and Restoring Insulin Sensitivity and Glucose Homeostasis in Living Mammals In Vivo Animal Model The Zucker Diabetic Fatty (ZDF) rat model was used (Carley and Severson, *Biochim. Biophys. Acta,* 1734:112-26 (2005)). Positive results in the ZDF rat model can indicate a potential for positive treatment outcomes in human Type II diabetics. In particular, circulating plasma triglyceride concentrations, circulating plasma glucose concentrations, abdominal fat, water utilization, urine secretion, and organ weights were examined in cohorts of ZRF rats treated with a potato polysaccharide preparation or with vehicle.

Dosing and Grouping

Two types of rats were used for the study (ZDF/ZDF rats (n=20) and heterozygous lean rats (n=20)). The rats within the groups were then chosen at random and divided into groups of 10. Group 1 included the ZDF vehicle fed rats, group 2 included the ZDF potato polysaccharide fed rats, group 3 included the lean vehicle fed rats, and group 4 included the lean potato polysaccharide fed rats. The vehicle was distilled water, and the potato polysaccharide was given daily each morning via oral gavage at a dosage of 0.05 mg per animal. The dose was usually given in 1 mL of water. Rats were caged in groups and maintained in 12 hour light/12 hour dark (7 am to 7 pm). The study lasted for 28 days.

Data Collection

Body weights were recorded weekly. Whole blood, serum, and plasma were collected at day 0 for baseline analysis. Plasma and serum was collected from fasting rats at day 14. Water consumption was monitored starting at day 24 and continued until termination. Urine collection for measurement of volume and protein content was on day 27. Whole blood, serum, and plasma were collected at day 28 (termination). Fasted blood glucose was measured at day 28, and liver and abdominal fat were collected and snap frozen in liquid nitrogen.

Total cholesterol (HDL, LDL, and triglycerides) and serum glucose were measured at days 0, 14, and 28. Serum creatinine was measured at termination. Whole blood was preserved in PAX RNA blood tubes for possible gene expression analysis. Abdominal fat, liver, and kidneys were weighed and used in calculating organ to body mass ratios. Plasma collected was stored from days 0, 14, and 28 for possible future analysis.

Experimental Animals

Twenty-two 7-week old, male Zucker Diabetic Fatty rats (ZDF, Code: 370) and twenty-two 7-8 week old, male ZDF Lean rats (Code: 371) were purchased from Charles Rivers Laboratories (Wilmington, Mass.). The study animals were allowed an acclimation period of 4 days prior to baseline blood collections, at which time two extra animals from each strain were dropped from the study based on baseline body weight. The rats were housed two rats per cage and maintained in the Innovive caging system (San Diego, Calif.) upon arrival. Cages were monitored daily to ensure the Innovive system maintained 80 air changes per hour and positive pressure. Rat rooms were maintained at temperatures of 66-75° F. and a relative humidity between 30 percent and 70 percent. The rooms were lit by artificial light for 12 hours each day (7:00 am to 7:00 pm). Animals had free access to water and Purina 5008 rodent food (Waldschimdt's, Madison, Wis.) for the duration of the study except during fasted experiments.

Drug Formulation

A potato polysaccharide preparation for animal testing was prepared as follows. Ten gram portions of raw potato material were homogenized with a Polytron homogenizer in ten volumes of distilled water and maintained at room temperature for 1 hour with occasional shaking. The raw potato homogenate was subsequently centrifuged at 4000 g for 10 minute in order to remove insoluble material. The resulting supernatant was purified by Solid Phase Extraction utilizing a Sep-Pak Plus C-18 cartridge. Semipurified polysaccharide material contained in 10 percent acetonitrile and 0.05% trifluoroacetic acid was dried and purified to homogeneity by reverse phase HPLC.

The eluted 3.5 minute HPLC fraction containing pure potato polysaccharide preparation was dried and used in animal testing.

The purified potato polysaccharide preparation (10 mL stock solution at 5 mg/mL concentration) was stored at 4° C. The vehicle for the study was sterile water (Catalog number 002488, Butler Schein). Each week, the stock solution was diluted 1:100 in sterile water (0.05 mg/mL) and dispensed into daily aliquots. All vehicle and drug solutions were stored at 4° C. and administered at room temperature daily by oral gavage (PO) in a volume of 1 mL/animal (0.15 mg/kg dose based on estimated body weight of 350 g).

Body Weights

Animals were weighed weekly with a calibrated digital balance to monitor animal health. Body weights were taken in a fed state, except for the terminal body weight measurement.

Blood Collection

Blood was collected on Day 0 for baseline, Day 14 for Week 2, and Day 28 during termination for Week 4. Animals were fasted for 11.5 hours (10:00 pm-9:30 am) prior to each blood collection, and if applicable, dosed 1 hour prior to the blood collection. Whole blood was collected into blood collection tubes for baseline pooled blood analysis (1.0 mL of blood from each animal) and terminal blood analysis (2.5 mL of blood from each animal). For Baseline and Days 14 and 28, 850 μL of whole blood was collected into pre-chilled K2EDTA tubes with DPP4i (1:100 P8340, Sigma Aldrich) added and processed to plasma. For Baseline and Days 14 and 28, 250 μL whole blood was collected into a SST tube and processed to serum.

Blood Analyses

Whole blood collected into blood tubes was frozen at −20° C. and shipped on ice packs for analyses. Plasma with DPP4i added were frozen at −20° C. and shipped on dry ice for analyses. Serum was frozen at −20° C. and shipped for analysis. Baseline and Day 14 sera were analyzed for the standard lipid panel (cholesterol, triglycerides, HDL, and LDL) as well as glucose. Terminal serum samples were analyzed for the standard lipid panel, glucose, and creatinine content.

Water Consumption

Beginning on Day 23, water consumption monitoring began and was continued for the remainder of the study. The difference in water weight (beginning weight of water in grams minus the end weight of water in grams) was divided by the number of animals per cage to determine the average amount of water in grams consumed per animal per day. Water added was accounted for in the measurements, and calculations were converted to mL/animal/day. On Day 26, animals were placed into individual metabolic cages; therefore, water consumption was monitored per animal instead of per cage.

Urine Collection

Urine was collected at room temperature for 24 hours from Day 26 to Day 27. Animals had free access to food and water throughout the procedure. Urine volumes were measured, and urine protein and creatinine were analyzed.

Fasted Glucose

Fasted blood glucose was measured at 9:30 am on Day 28, about 1 hour post-dose with 11.5 hours of fasting. Blood glucose was measured with a Bayer Contour glucometer. Termination immediately followed the blood glucose measurements.

Necropsy

All animals were euthanized by isoflurane overdose and thoracotomy following the collection of fasted blood glucose data on Day 28 of the study. Blood was collected via descending vena cava. Liver and abdominal fat were collected and weighed, and a portion of the left lateral liver lobe and abdominal fat were placed into individual histology cassettes and snap frozen in liquid nitrogen. General pathological observations were recorded.

Study Design

Animals were recruited into treatment groups based on body weights collected on Day −1. Animals were fasted for 11.5 hours (10:00 pm-9:30 am) prior to collection of blood on Day 0 for baseline parameter analyses. Each animal was anesthetized using isoflurane inhalant anesthetic with subsequent retro-orbital blood collection technique, followed by subcutaneous fluid replacement. Study animals received vehicle (sterile water) or a potato polysaccharide via oral gavage beginning on Day 1 and for the duration of the experiment. Animals were administered 1.0 mL of a 0.05 mg/mL solution to achieve a target dose of 0.15 mg/kg/day.

At the end of Week 2, animals were fasted and dosed prior to collection of blood on Day 14 for mid-study parameter analyses. Each animal was anesthetized using isoflurane inhalant anesthetic with subsequent retro-orbital blood collection technique. Water consumption monitoring began on Day 23 and continued for the duration of the study. On Day 26, study animals were placed into individual metabolic cages for a 24-hour collection of urinary output. Urine volume was measured, and two clean, processed aliquots were retained for analysis.

Figure 37:
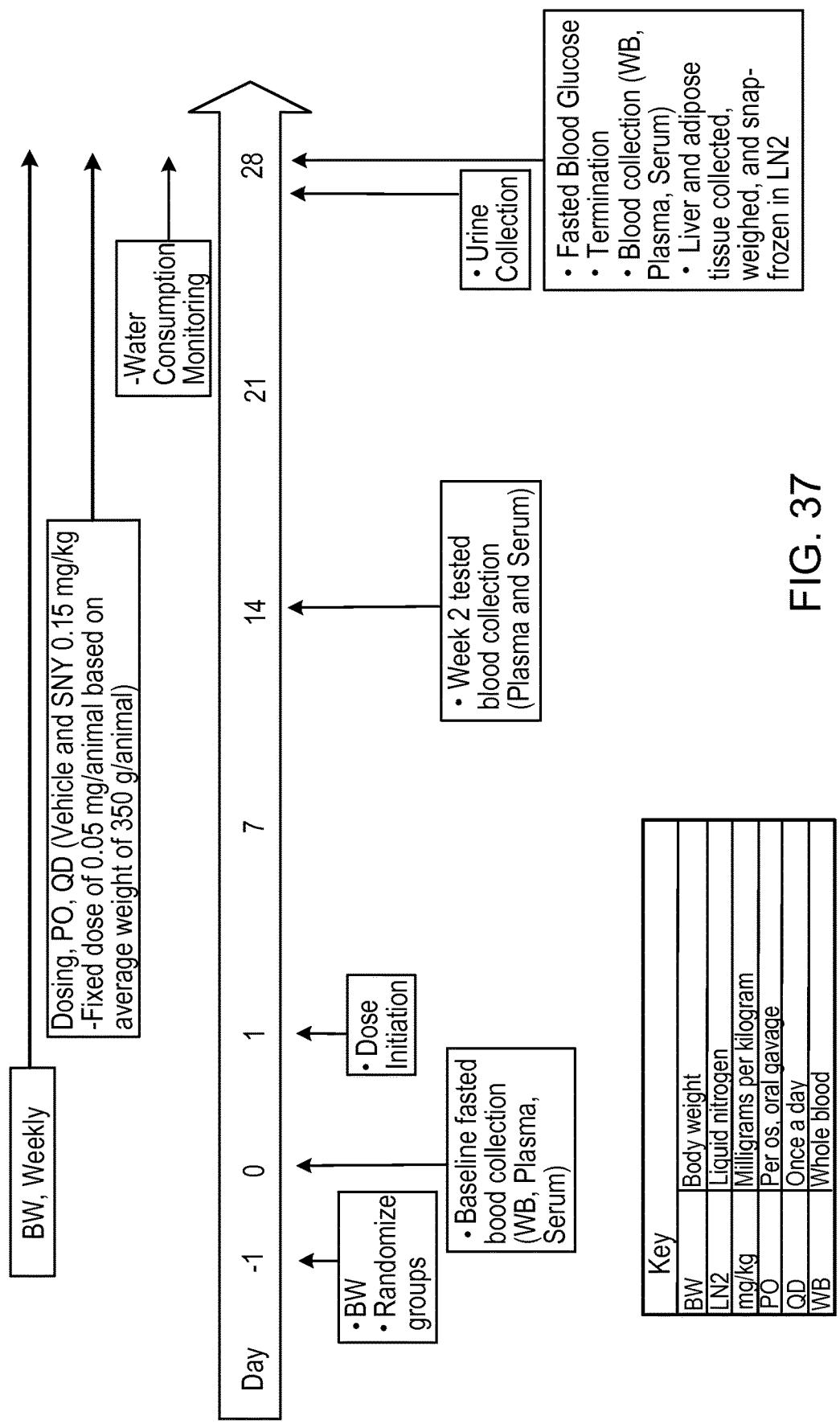
FIG. 37 is a schematic of the study design used to test the use of a potato polysaccharide preparation to reduce diabetes and obesity parameters within living mammals.

At the end of Week 4, animals were fasted and dosed prior to measurement of blood glucose on Day 28. Fasted blood glucose was measured via tail clip blood collection, and termination began directly thereafter Animals were euthanized using isoflurane inhalant anesthetic followed with a thoracotomy. Blood was collected via the descending vena cava and distributed into the appropriate tubes. The liver and abdominal fat were collected and weighed, and portions snap frozen in liquid nitrogen. The study design and treatments in the groups for the rats are presented in FIG. 37 and Table 11.

TABLE 11

Treatment Groups.

Group 1: Fa/Fa Vehicle (Sterile Water), n = 10
Group 2: Fa/Fa potato polysaccharide 0.05 mg/day, n = 10
Group 3: Lean +/? Vehicle (Sterile Water), n = 10
Group 4: Lean +/? potato polysaccharide 0.05 mg/day, n = 10

+/? represents the ZDF lean rats that are heterozygotic with a normal leptin receptor allele and that display no abnormal metabolic symptoms.

Statistical Analysis

Data were reported in mean+SEM. Statistical analysis was performed using the Prism 5.0d program by GraphPad Software. Analysis of variation for body weight, lipid panel parameters (cholesterol, triglycerides, HDL, and LDL), serum glucose, and water consumption were performed through a two-way ANOVA. Bonferroni post-tests were used to compare replicate means by row. Analysis of variation for blood glucose, urine parameters (urine volume, proteinuria, and creatinine clearance), liver-to-body weight ratio, and abdominal fat-to-body weight ratio were performed through a one-way ANOVA with a Bonferroni post-test to compare all pairs of columns. Significance was determined when the p-value was less than an alpha of 0.05 with a confidence interval of 95%. Outliers were screened by testing the group's mean versus the standard error of the mean (SEM) for said time point. If the relationship of SEM to mean was in excess of 10%, then the data points of that group at that time point were carried through an outlier test. Data points outside a z-score variation of 3.0 were listed as outliers and not included in the mean or SEM for the group. In Group 1 for Day 6 body weight, one animal's value was considered an outlier and was removed from the graphs and statistical analysis.

Results

Figure 38:
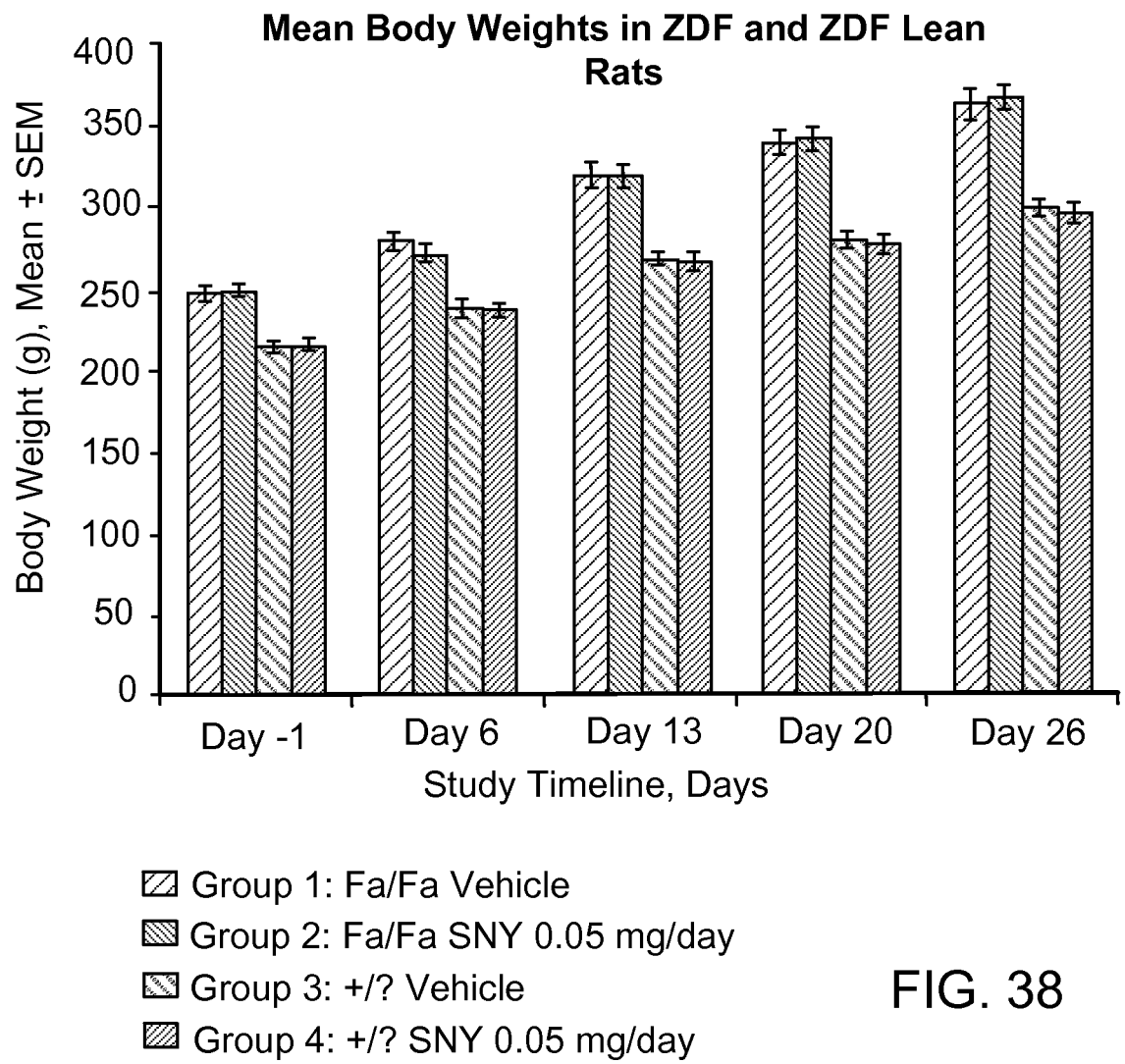
FIG. 38 is a graph plotting mean body weights for ZDF rats (Fa/Fa) and lean ZDF rats (+/?) treated with vehicle or a potato polysaccharide preparation (SNY).
Figure 39:
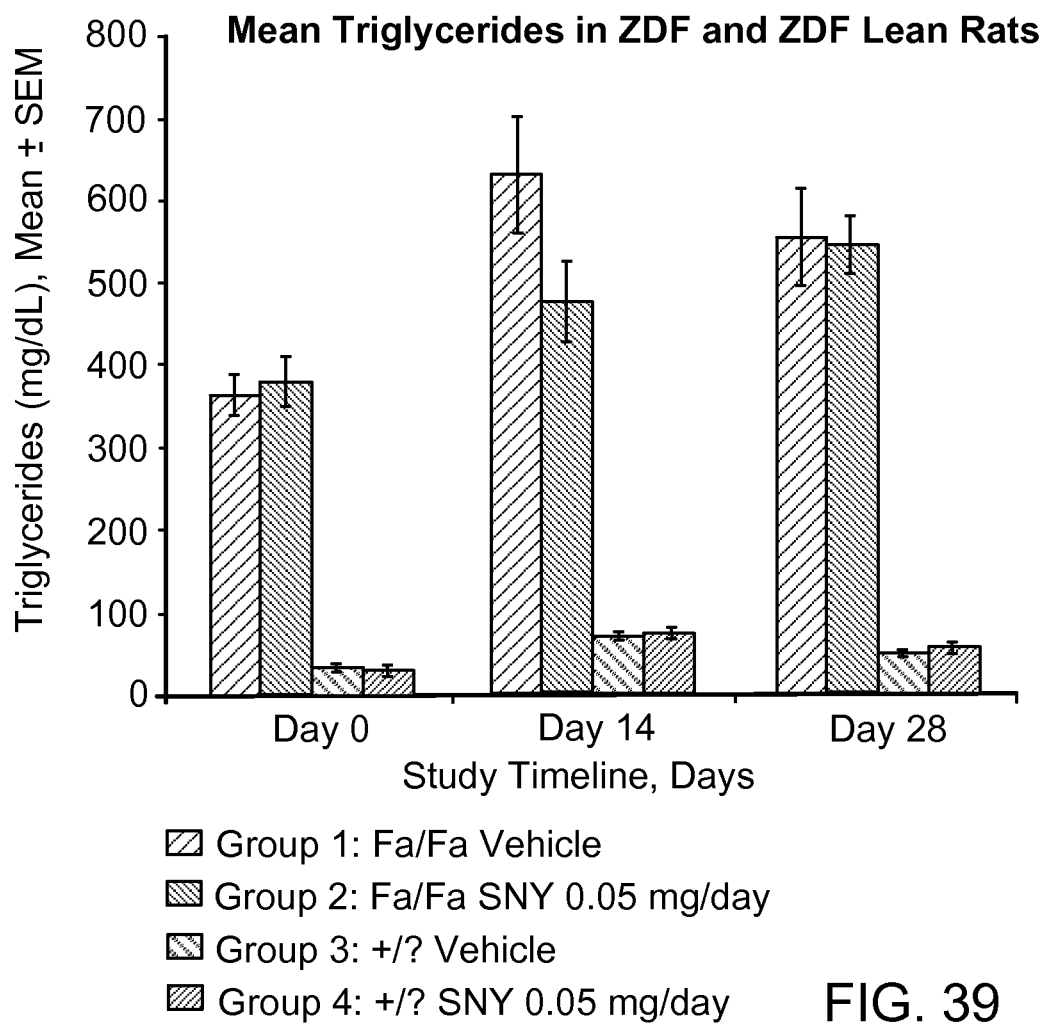
FIG. 39 is a graph plotting mean triglyceride levels for ZDF rats (Fa/Fa) and lean ZDF rats (+/?) treated with vehicle or a potato polysaccharide preparation (SNY).
Figure 40:
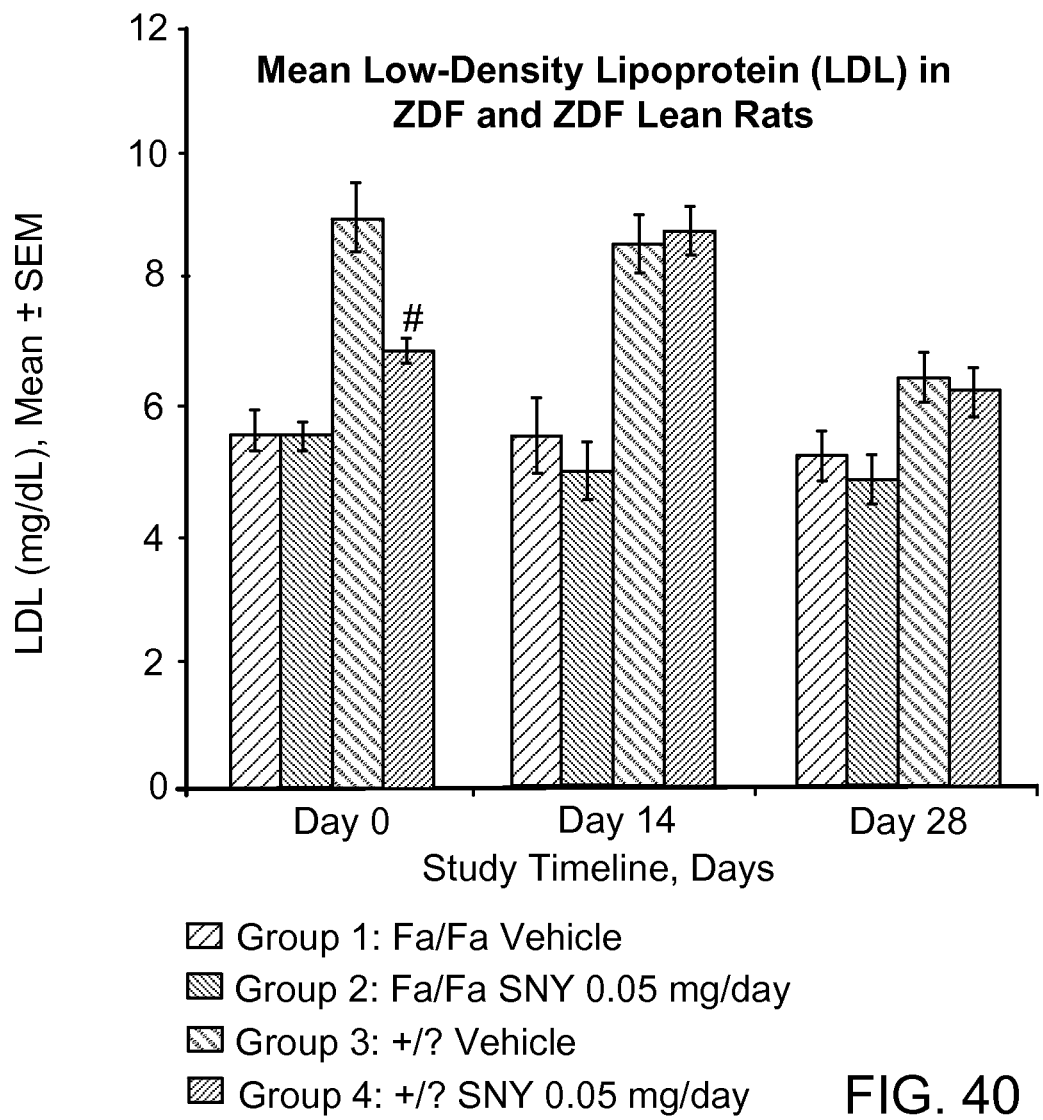
FIG. 40 is a graph plotting mean LDL levels for ZDF rats (Fa/Fa) and lean ZDF rats (+/?) treated with vehicle or a potato polysaccharide preparation (SNY).
Figure 41:
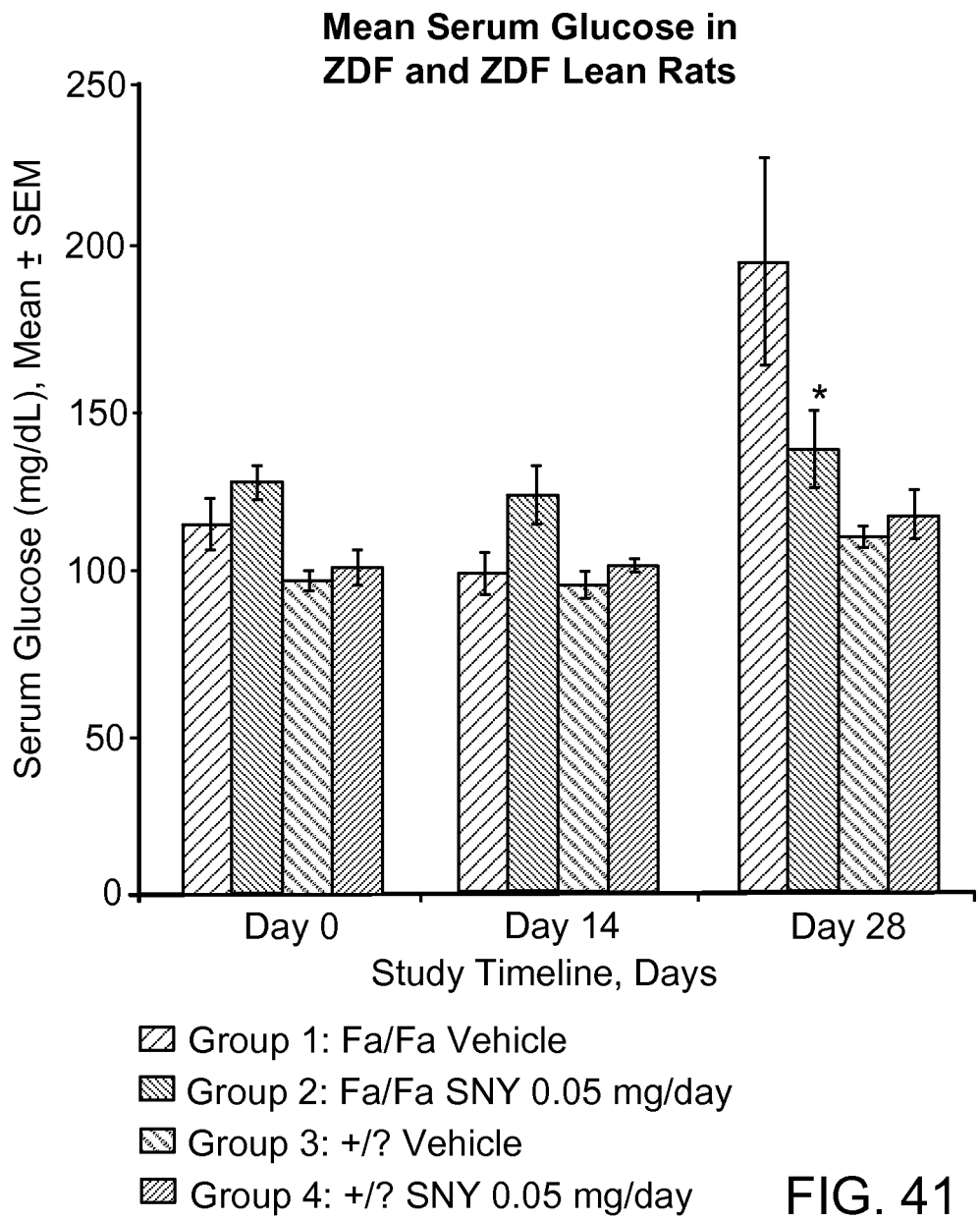
FIG. 41 is a graph plotting mean serum glucose levels for ZDF rats (Fa/Fa) and lean ZDF rats (+/?) treated with vehicle or a potato polysaccharide preparation (SNY).
Figure 42:
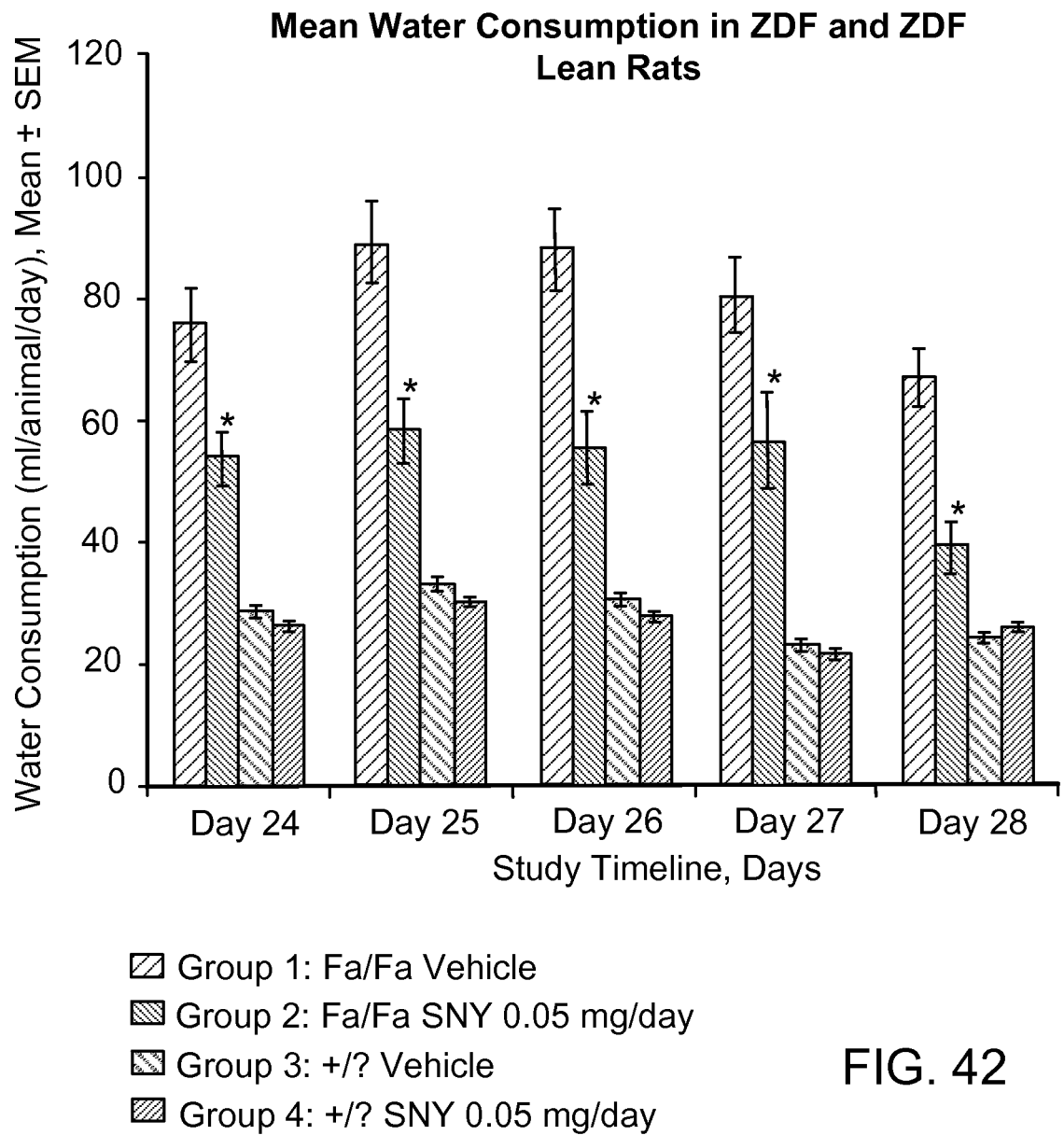
FIG. 42 is a graph plotting mean water consumption levels for ZDF rats (Fa/Fa) and lean ZDF rats (+/?) treated with vehicle or a potato polysaccharide preparation (SNY).
Figure 43:
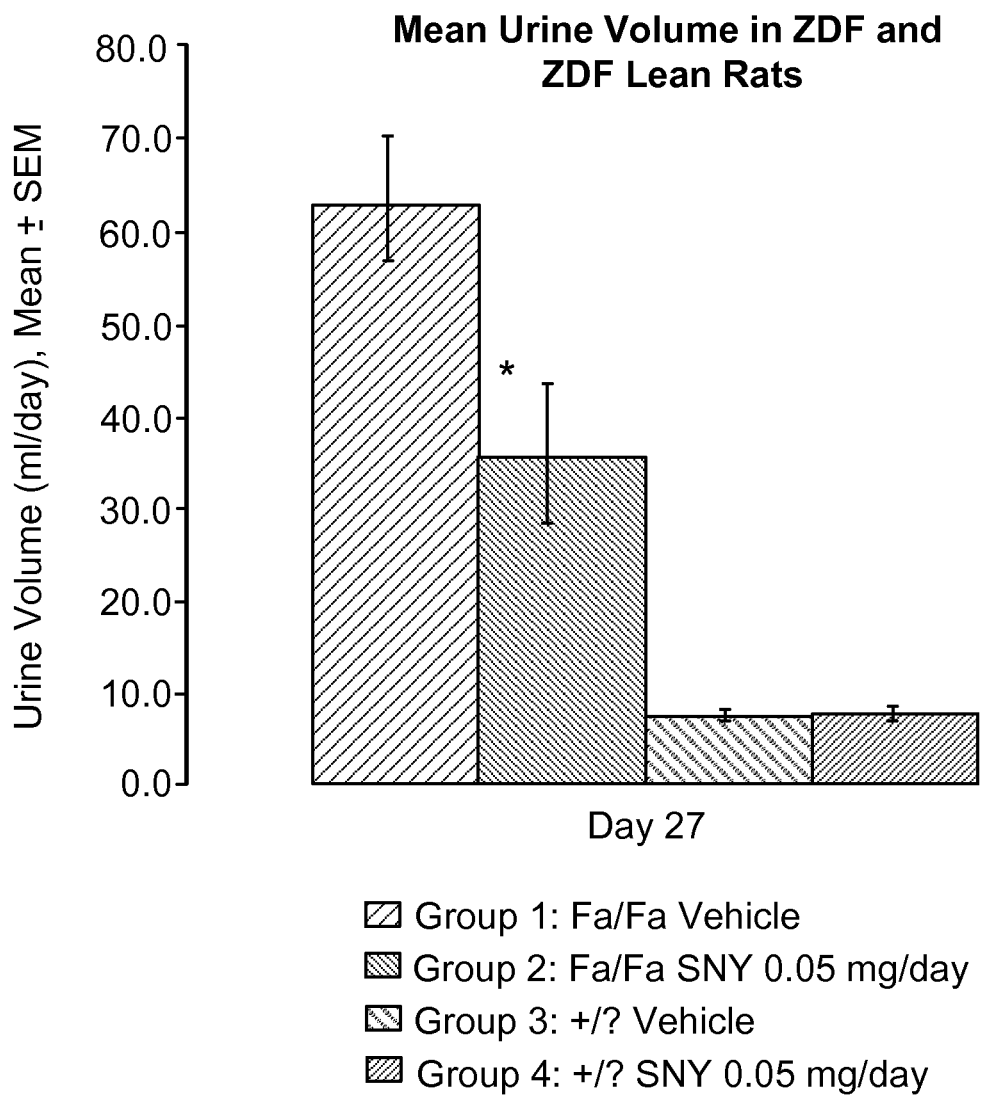
FIG. 43 is a graph plotting mean urine volumes for ZDF rats (Fa/Fa) and lean ZDF rats (+/?) treated with vehicle or a potato polysaccharide preparation (SNY).
Figure 44:
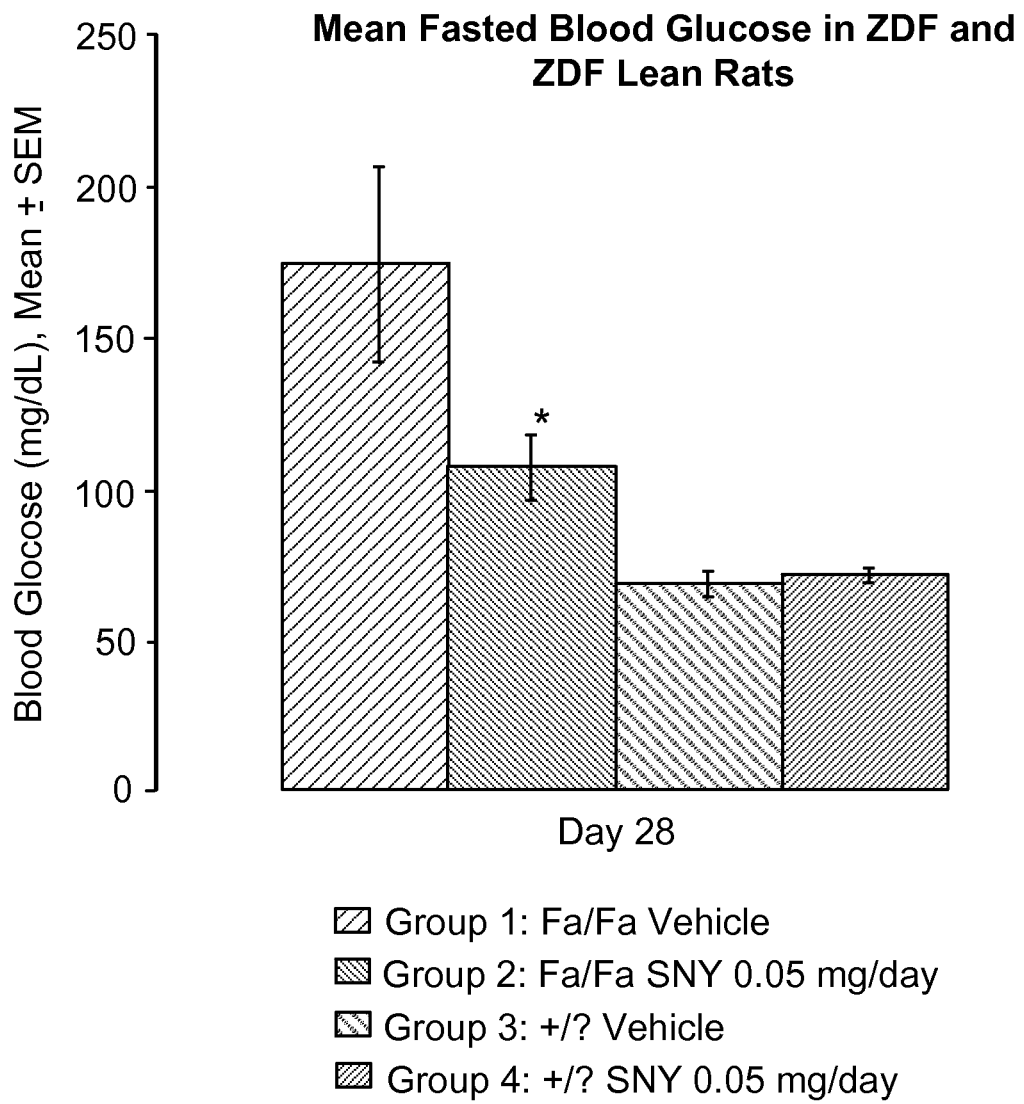
FIG. 44 is a graph plotting mean blood glucose levels for fasted ZDF rats (Fa/Fa) and fasted, lean ZDF rats (+/?) treated with vehicle or a potato polysaccharide preparation (SNY).
Figure 45:
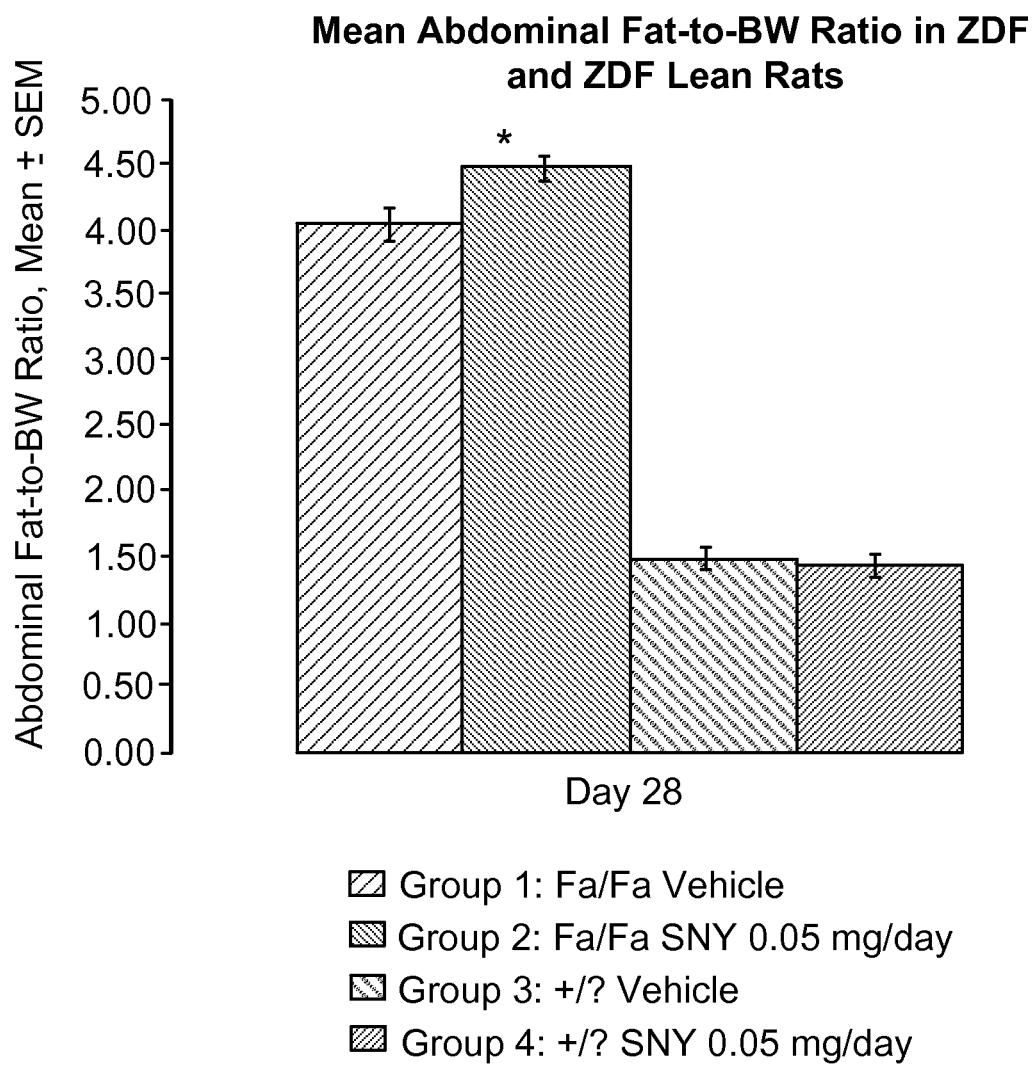
FIG. 45 is a graph plotting mean abdonminal fat weight to body weight ratios for ZDF rats (Fa/Fa) and lean ZDF rats (+/?) treated with vehicle or a potato polysaccharide preparation (SNY).
Figure 46:
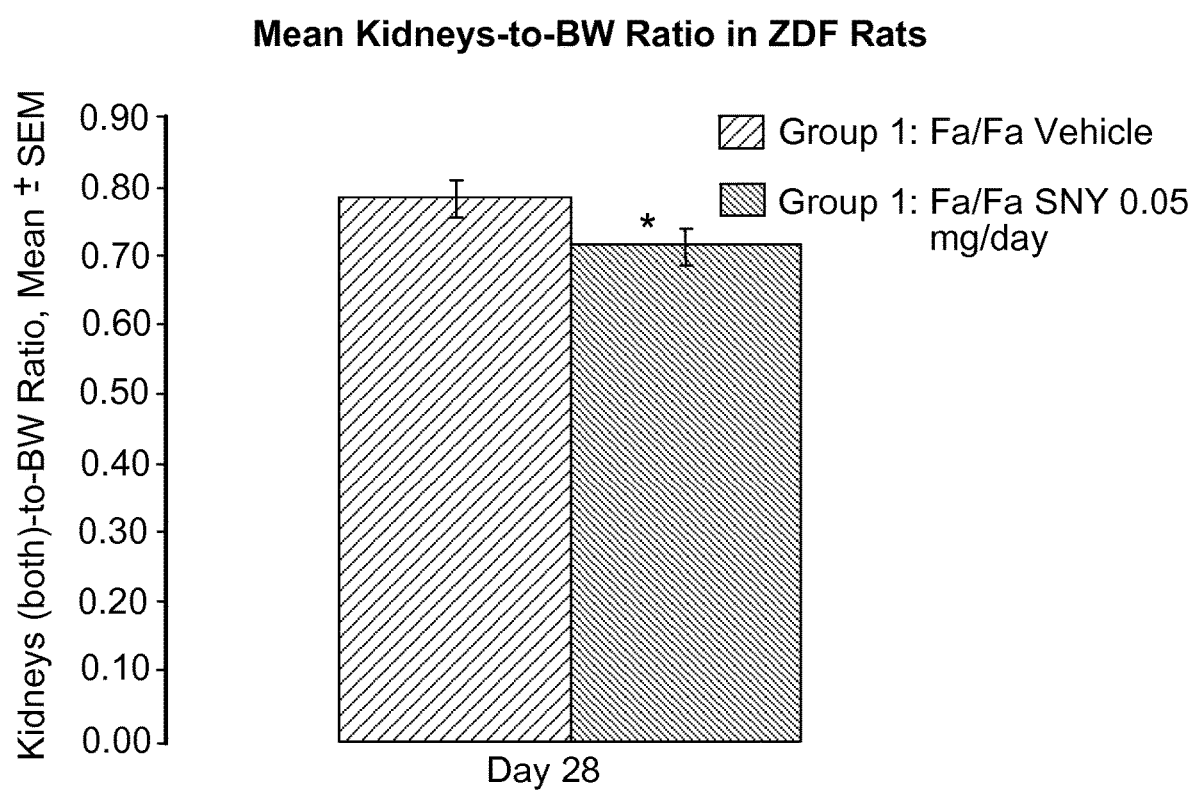
FIG. 46 is a graph plotting mean kidney weight to body weight ratios for ZDF rats (Fa/Fa) treated with vehicle or a potato polysaccharide preparation (SNY).
Figure 47:
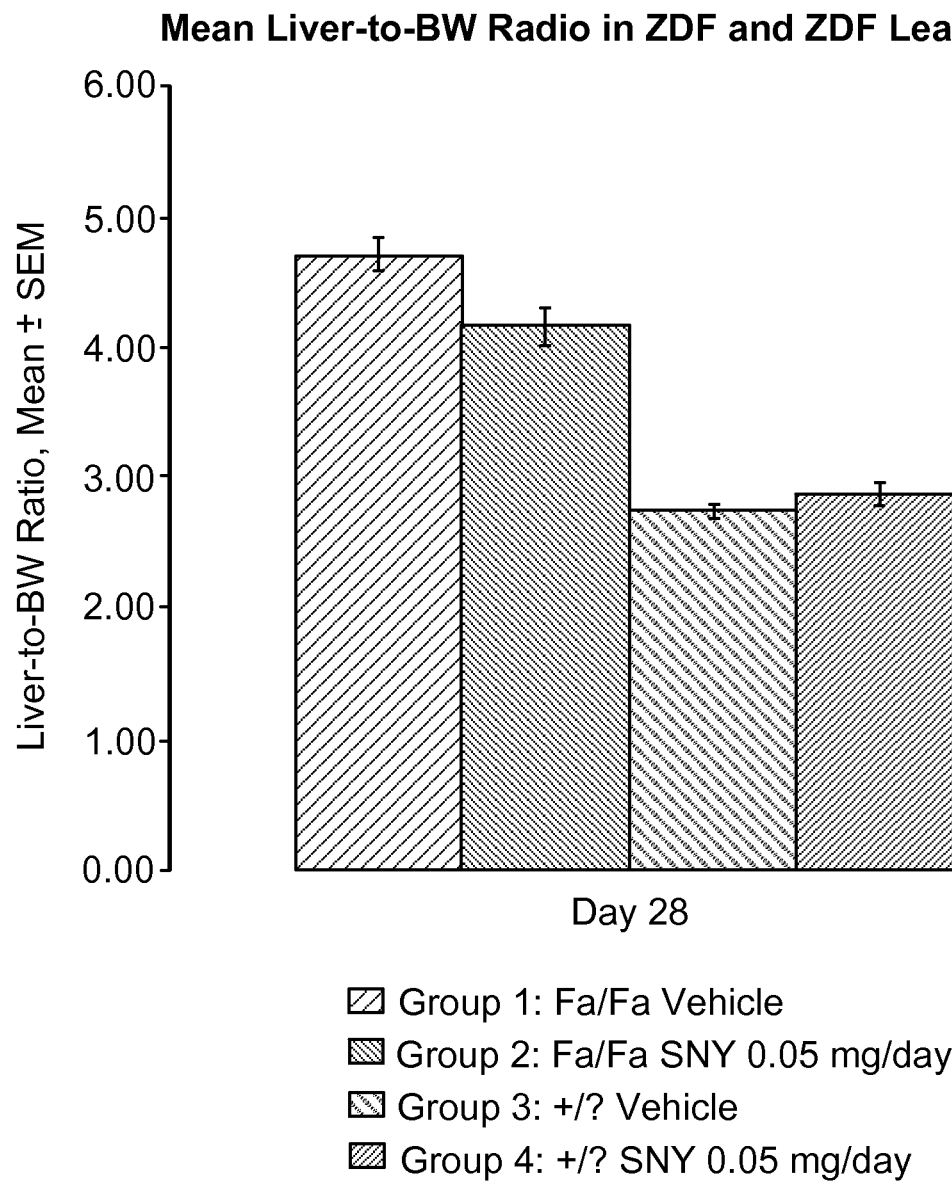
FIG. 47 is a graph plotting mean liver weight to body weight ratios for ZDF rats (Fa/Fa) and lean ZDF rats (+/?) treated with vehicle or a potato polysaccharide preparation (SNY).

Mean body weight between the four groups did not change (FIG. 38). Comparing groups 1 and 2, the rats treated with a potato polysaccharide preparation exhibited a significant drop in triglyceride levels at day 14 ($P<0.05$; FIG. 39). On day 0, mean LDL was lower in Group 4 as compared to Group 3 (FIG. 40). Mean serum glucose was statistically lower on day 28 for rats of Group 2 treated with the potato polysaccharide preparation (FIG. 41). Rats of Group 2, which were treated with a potato polysaccharide preparation, exhibited a statistically significant reduction in water consumption and urine production (FIGS. 42 and 43) as compared to the rats of Group 1. Rats of Group 2 exhibited mean fasted glucose levels that were statistically lower than the levels observed for rats of Group 1 (FIG. 44). Abdominal fat in the potato polysaccharide preparation treated group was statistically elevated (FIG. 45). In addition, the kidney weight to body weight ratio was lower for the rats of Group 2 as compared to those for the rats of Group 1 (FIG. 46).

These results demonstrate that administration of a potato polysaccharide preparation can maintain the metabolic integrity of adipocytes during a critical developmental period of insulin desensitivity observed in vehicle-treated ZDF controls. In the vehicle-treated cohort, a developmental period highlighted by markedly increased plasma triglyceride concentrations is functionally linked to temporal development of insulin desensitization and diabetic levels of plasma glucose. In the cohort treated with a potato polysaccharide preparation, a statistically significant reduction of plasma triglyceride concentrations was observed at the 14 day time point, which is critically linked to significantly lower levels of fasting and non-fasting "true" glucose. Lower levels of plasma glucose were associated with significantly reduced water intake and urine output, indicating a marked inhibition of the development of multiple type II diabetic symptoms.

These positive outcomes are directly translatable to inhibition of type II diabetes development in humans. Interestingly, levels of true glucose in vehicle-treated ZDF controls were lower than those observed in treated ZDF rats at early time points. This was consistent with temporal development of insulin insensitivity in humans via presentation of prediabetic lowered plasma glucose levels. Administration of a potato polysaccharide preparation was observed to inhibit temporal development of prediabetic lowered levels of plasma glucose. In effect, administration of a potato polysaccharide preparation maintained normal levels of plasma glucose via maintenance of insulin sensitivity. Maintenance of normal levels of plasma glucose was statistically linked to diminished circulating plasma triglycerides at the 14 day time point, which was functionally linked to higher levels of abdominal fat in treated animals that were normally observed in obese non-diabetic humans. In summary, administration of a potato polysaccharide preparation as described herein maintained metabolic integrity of abdominal fat storage that is linked to temporal development of insulin insensitivity. This also indicates that a potato polysaccharide preparation can be used to stabilize metabolic processes in obese human populations, thereby permitting programmed dietary regimens to combat obesity disorders effectively.

Example 10

Use of Potato Polysaccharide Preparations to Treat Fatty Liver Diseases

To assess the ability of potato polysaccharide preparations to treat fatty liver diseases, the livers from the rats of the four groups of Example 9 were collected, weighed, and examined as described in this Example.

DNA Microarray

Total RNA extracted from liver samples was isolated and purified using the RNeasy mini kit (Qiagen, Valencia, Calif.). In particular, 100 mg of tissue was resuspended in 1.8 mL of RLT lysis buffer (Qiagen) and homogenized with a polytron homogenizer for 30 seconds. The samples were then processed according to the manufacturer's instructions (Qiagen, Valencia, Ca). In the final step, the RNA was eluted with 50 µL of RNase-free water by centrifugation for 1 minute at 13,000 g. The RNA was analyzed on a model 2100 bioanalyzer (Agilent, Santa Clara, Calif.) using a total RNA nanochip according to the manufacturer's protocol.

DNA microarray analyses were performed using a system provided by Agilent. Arrays included four arrays per chip (Agilent Rat gene expression 4X44K version 3 chips). Total RNA was reverse transcribed (700 ng) using T7 primers, labeled, and transcribed using Cyanine-3 dye. Each array was hybridized with 2 ng of labeled cRNA at 65° C. for 18 hours. Arrays were scanned using an Agilent array scanner.

Results

Oral administration of the potato polysaccharide preparation over a time course of 28 days produced a statistically significant reduction (about 40%) in the liver weight to body weight ratios in Zucker ZDF rats, as compared to control Zucker ZDF rats receiving vehicle (p=0.01, N=9).

In addition, daily oral administration of the potato polysaccharide preparation resulted in a coordinated enhancement of gene expression in liver tissue that is functionally linked to enhanced protein and nucleic acid biosynthesis (Table 12).

TABLE 12

Enhanced expression of genes driving mitochondrial biogenesis linked to enhanced protein and nucleic acid biosynthesis.

| Gene Symbol | Gene Name | Fold Change | P value |
|---|---|---|---|
| Slc25a33 | solute carrier family 25 (pyrimidine nucleotide carrier), member 33 | 3.6 | 0.00005 |
| Tomm40 | translocase of outer mitochondrial membrane 40 homolog (yeast) | 2.4 | 0.0005 |

TABLE 12-continued

Enhanced expression of genes driving mitochondrial biogenesis linked to enhanced protein and nucleic acid biosynthesis.

| Gene Symbol | Gene Name | Fold Change | P value |
|---|---|---|---|
| Mrpl3 | mitocriondrial ribosomal protein L3 | 2.4 | 0.000008 |
| Mrps18b | mitochondrial ribosomal protein S18B | 1.9 | 0.002 |
| Mrps9 | mitochondrial ribosomal protein S9 | 1.8 | 0.001 |
| Fars2 | phenylalanyl-tRNA synthetase 2, mitochondrial | 1.8 | 0.001 |
| Mrpl15 | mitochondrial ribosomal protein L15 | 1.7 | 0.004 |
| Mrps23 | mitochondrial ribosomal protein S23 | 1.6 | 0.0003 |
| Mrps2 | mitochondrial ribosomal protein S2 | 1.6 | 0.003 |
| Mrpl17 | mitochondrial ribosomal protein L17 | 1.5 | 0.0001 |
| TFAM | Transcription factor A | 1.5 | 0.05 |

Daily oral administration of the potato polysaccharide preparation also resulted in a coordinated enhancement of gene expression in liver tissue that is functionally linked to enhanced TCA cycle activity and ATP production (Table 13).

TABLE 13

Enhanced expression of genes driving mitochondrial energy production

| Gene Symbol | Gene Name | Fold Change | P value |
|---|---|---|---|
| Prodh | proline dehydrogenase (oxidase) 1 | 2.9 | 0.003 |
| Slc25a1 | solute carrier family 25 (mitochondrial carrier, citrate transporter), member 1 | 2.3 | 0.00004 |
| Hmgcl | 3-hydroxymethyl-3-methylglutaryl-CoA lyase | 2.2 | 0.0004 |
| Cps1 | carbamoyl-phosphate synthetase 1 | 2.0 | 0.0001 |
| Aldh4a1 | aldehyde dehydrogenase 4 family, member A1 | 1.9 | 0.0003 |
| Mdh2 | malate dehydrogenase 2, NAD (mitochondrial) | 1.9 | 0.0002 |
| Atp5b | ATP synthase, H+ transporting, mitochondrial F1 complex, beta polypeptide | 1.8 | 0.0002 |
| Slc25a22 | solute carrier family 25 (mitochondrial carrier, glutamate), member 22 | 1.6 | 0.0007 |
| Slc25a19 | solute carrier family 25 (mitochondrial thiamine pyrophosphate carrier), member 19 | 1.6 | 0.00009 |
| Uqcrc2 | ubiquinol cytochrome c reductase core protein 2 | 1.6 | 0.0001 |
| Abcf2 | ATP-binding cassette, subfamily F (GCN20), member 2 | 1.6 | 0.004 |

Daily oral administration of the potato polysaccharide preparation resulted in differential expression of genes functionally involved in lipogenesis, triglyceride assembly, and mitochondrial lipolysis (Table 14).

TABLE 14

Differential expression of genes involved in lipogenesis, triglyceride assembly, and mitochondrial lipolysis.

| Gene Symbol | Gene Name | Fold Change | P value |
|---|---|---|---|
| Acbd4 | acyl-CoA binding domain containing 4 | 3.0 | 0.00003 |
| Fads1 | fatty acid desaturase 1 | 1.9 | 0.003 |
| Gnpat | glyceronephosphate O-acyltransferase | 1.6 | 0.002 |
| Lypla1 | lysophospholipase I | 1.5 | 0.001 |
| Cpt2 | Carnitine palmitoyltransferase | 1.2 | 0.04 |
| Pck2 | phosphoenolpyruvate carboxykinase 2 (mitochondrial) | −1.4 | 0.003 |

TABLE 14-continued

Differential expression of genes involved in lipogenesis, triglyceride assembly, and mitochondrial lipolysis.

| Gene Symbol | Gene Name | Fold Change | P value |
|---|---|---|---|
| Agpat4 | 1-acylglycerol-3-phosphate O-acyltransferase 4 (lysophosphatidic acid acyltransferase, delta | −1.8 | 0.001 |
| Acaca | acetyl-CoA carboxylase alpha | −2.3 | 0.00007 |

Daily oral administration of the potato polysaccharide preparation did not result in any significant change in the expression of three hepatic reference or housekeeping genes (Congiu et al., Liver Int., 31:386-90 (2011); Table 15).

TABLE 15

Expression of hepatic reference or housekeeping genes.

| Gene Symbol | Gene Name | Mean signal difference |
|---|---|---|
| Gapdh | glucuronidase, beta | 0.1 |
| Hprt | hypoxanthine phosphoribosyltransferase 1 | 0.06 |
| Srsf4 | serine/arginine-rich splicing factor 4 | 0.004 |

Figure 48:
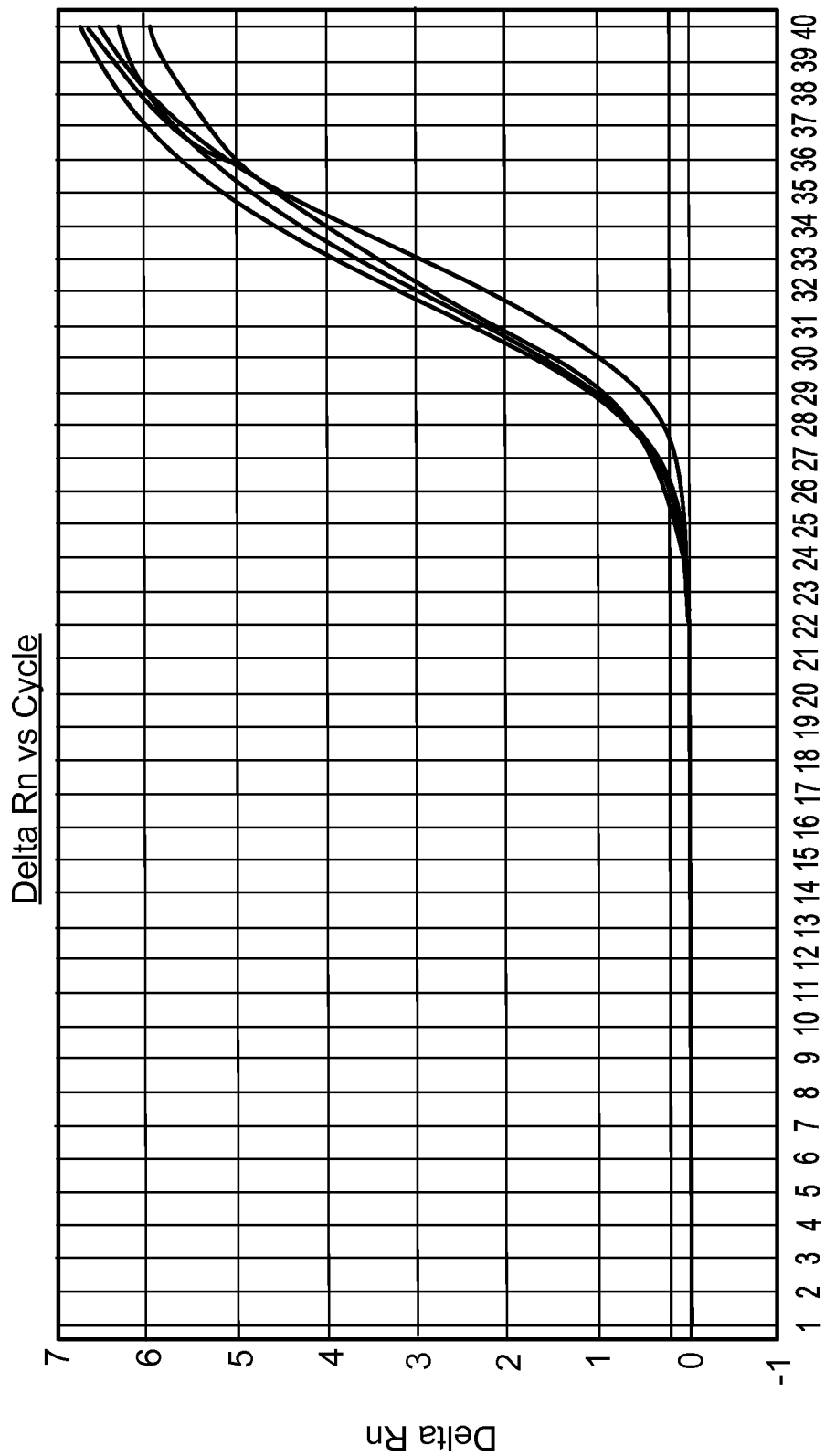
FIG. 48 is a real time PCR amplification plot for TFAM demonstrating differences in threshold cycle numbers between potato polysaccharide preparation-treated ZDF rats and untreated control ZDF rats. The lower cycle number for the treated rats equates to a higher gene expression.
Figure 49:
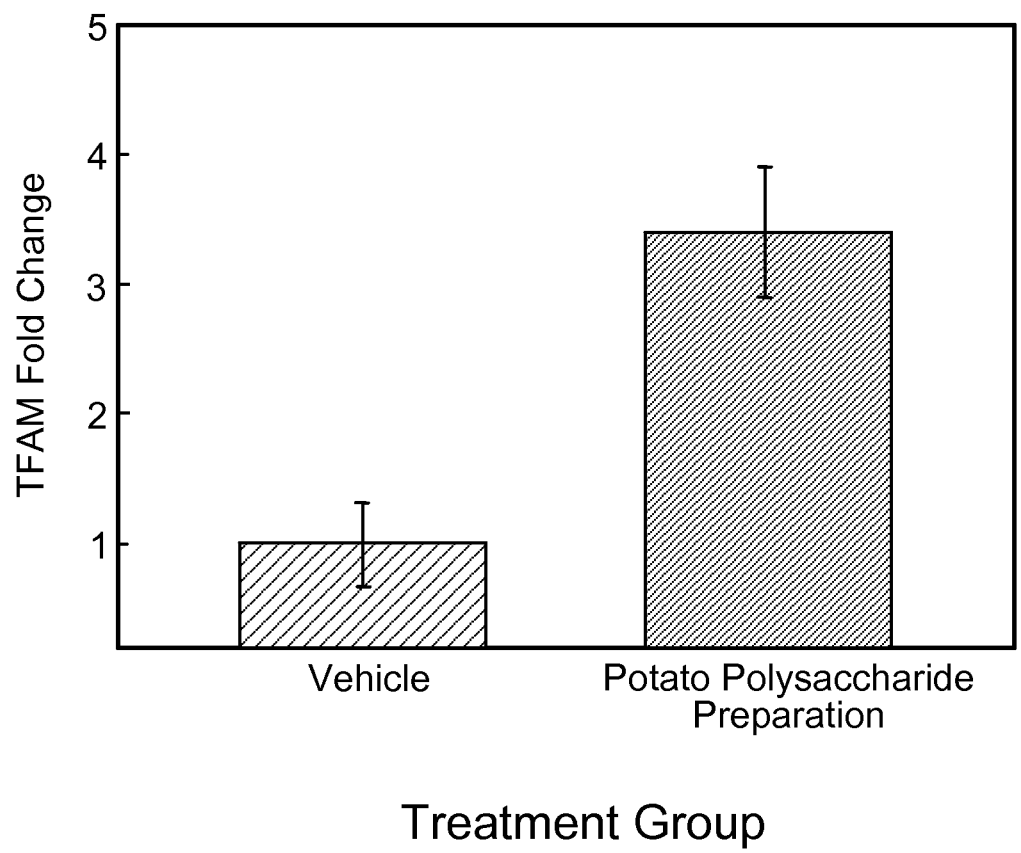
FIG. 49 is a graph plotting the fold change in expression of TFAM in treated versus untreated rats.

Real-time PCR analysis of TFAM expression was performed to validate the DNA microarray data sets. After rats were given the potato polysaccharide preparation for 28 days, real-time PCR was performed to measure changes in TFAM gene expression in ZDF rat livers. GAPDH was used as a reference gene. The real-time PCR master mix included 25 µL 2× universal master mix, 2.5 µL 20× detector set (with the primer and probe), and 21.5 µL of water. PCR was performed in an Applied Biosystems 7500 sequence detection system. The thermocycler conditions included denaturation at 95° C. for 15 seconds and annealing/extension at 60° C. for 60 seconds. Forty cycles of PCR were preceded by 95° C. for 10 minutes. Reactions were performed in triplicate. The relative quantities of TFAM were determined using the formula 2−ΔΔCt using the Applied Biosystems 7500 software. There was a 3.4±0.5 fold change increase relative to the untreated rats (FIGS. 48 and 49).

Taken together, these results demonstrate that potato polysaccharide preparations can be used as anti-steatotic agents to treat fatty liver diseases.

OTHER EMBODIMENTS

It is to be understood that while the invention has been described in conjunction with the detailed description thereof, the foregoing description is intended to illustrate and not limit the scope of the invention, which is defined by the scope of the appended claims. Other aspects, advantages, and modifications are within the scope of the following claims.

What is claimed is:

1. A method for treating a fatty liver disease, wherein said method comprises:
   (a) identifying a mammal with a fatty liver disease, and
   (b) administering to said mammal a composition comprising a potato polysaccharide preparation obtained from homogenized raw potatoes, wherein said potato polysaccharide preparation is eluted from said homogenized raw potatoes with 10% acetonitrile, and wherein said potato polysaccharide preparation is a potato polysaccharide preparation that, when derivatized, results in at least the following acylated carbohydrates as assessed using gas chromatography/mass spectography:
   (a) myo-inositol, set to 1× to serve as an internal standard,
   (b) glucose at about 40× to about 60× the myo-inositol content,
   (c) xylose at about 10× to about 20× the myo-inositol content,
   (d) mannose at about 5× to about 15× the myo-inositol content, and
   (e) galactose at about 3× to about 7× the myo-inositol content, wherein the severity of a symptom of said fatty liver disease is reduced.

2. The method of claim 1, wherein said composition comprises said potato polysaccharide preparation in an amount that results in between 0.05 mg and 50 mg of the potato polysaccharide component of said potato polysaccharide preparation being administered to said mammal per kg of body weight of said mammal.

3. The method of claim 1, wherein said composition comprises between 1 mg and 100 mg of said potato polysaccharide preparation.

4. The method of claim 1, wherein said composition comprises between 6 mg and 20 mg of said potato polysaccharide preparation.

5. The method of claim 1, wherein said composition comprises between 1 mg and 100 mg of the potato polysaccharide component of said potato polysaccharide preparation.

6. The method of claim 1, wherein said composition comprises between 6 mg and 20 mg of the potato polysaccharide component of said potato polysaccharide preparation.

7. The method of claim 1, wherein said composition is in the form of a tablet.

8. The method of claim 1, wherein said composition comprises alpha lipoic acid.

9. The method of claim 1, wherein said composition comprises alpha tocopherol.

10. The method of claim 1, wherein said potato polysaccharide preparation is in an amount that results in between 0.075 mg and 0.5 mg of the potato polysaccharide component of said potato polysaccharide preparation being administered to said mammal per kg of body weight of said mammal.

11. The method of claim 1, wherein at least about 80 percent of said potato polysaccharide preparation is potato polysaccharide.

12. The method of claim 1, wherein at least about 90 percent of said potato polysaccharide preparation is potato polysaccharide.

13. The method of claim 1, wherein at least about 95 percent of said potato polysaccharide preparation is potato polysaccharide.

14. The method of claim 1, wherein said mammal is a human.

15. The method of claim 1, wherein said potato polysaccharide preparation eluted from said homogenized raw potatoes with 10% acetonitrile is eluted from a C18 cartridge.

16. The method of claim 1, wherein said potato polysaccharide preparation eluted from said homogenized raw potatoes is eluted from an HPLC peak at 3.5 minutes.

\* \* \* \* \*